(12) United States Patent
Wang et al.

(10) Patent No.: US 11,254,696 B2
(45) Date of Patent: Feb. 22, 2022

(54) DIANILINOPYRIMIDINE COMPOUND FOR INHIBITING KINASE ACTIVITY

(71) Applicant: Shenzhen Targetrx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/954,246

(22) PCT Filed: Dec. 12, 2018

(86) PCT No.: PCT/CN2018/120618
§ 371 (c)(1),
(2) Date: Jun. 16, 2020

(87) PCT Pub. No.: WO2019/120121
PCT Pub. Date: Jun. 27, 2019

(65) Prior Publication Data
US 2021/0087213 A1  Mar. 25, 2021

(30) Foreign Application Priority Data
Dec. 21, 2017 (CN) .......................... 201711395072.0

(51) Int. Cl.
C07F 9/6512 (2006.01)
C07F 9/6558 (2006.01)

(52) U.S. Cl.
CPC ........ *C07F 9/65583* (2013.01); *C07F 9/6512* (2013.01)

(58) Field of Classification Search
CPC .................................................... C07F 9/6512
See application file for complete search history.

(56) References Cited

U.S. PATENT DOCUMENTS

| | | | |
|---|---|---|---|
| 7,067,522 | B2 | 6/2006 | Pease et al. |
| 8,901,120 | B2 | 12/2014 | Bearss et al. |
| 9,012,462 | B2 | 4/2015 | Wang et al. |
| 9,345,719 | B2 | 5/2016 | Cha et al. |
| 9,611,281 | B2 | 4/2017 | You et al. |
| 9,611,283 | B1 | 4/2017 | Zhang et al. |
| 9,834,518 | B2 | 12/2017 | Zhu et al. |
| 9,834,571 | B2 | 12/2017 | Dalgarno et al. |
| 10,053,477 | B2 | 8/2018 | Ding et al. |
| 2014/0024620 | A1 | 1/2014 | Dalgarno et al. |
| 2021/0009613 | A1 | 1/2021 | Wang et al. |

FOREIGN PATENT DOCUMENTS

| | | |
|---|---|---|
| CN | 102105150 A | 6/2011 |
| CN | 103153064 A | 6/2013 |
| CN | 103501612 A | 1/2014 |
| CN | 105330698 A | 2/2016 |
| CN | 106336382 A | 1/2017 |
| JP | 2011-523646 A | 8/2011 |
| JP | 2013-529630 A | 7/2013 |
| JP | 2013-539795 A | 10/2013 |
| JP | 2014-509661 A | 4/2014 |
| JP | 2014-514348 A | 6/2014 |
| JP | 2015-518490 A | 7/2015 |

(Continued)

OTHER PUBLICATIONS

PubChem CID 68165474, National Center for Biotechnology Information. "PubChem Compound Summary for CID 68165474" PubChem, https://pubchem.ncbi.nlm.nih.gov/compound/68165474. Accessed Mar. 26, 2021, create date Nov. 30, 2012. (Year: 2012).*
PubChem CID 89945229—National Center for Biotechnology Information. PubChem Compound Summary for CID 89945229. https://pubchem.ncbi.nlm.nih.gov/compound/89945229. Accessed Jun. 7, 2021, create date Feb. 13, 2015. (Year: 2015).*
Extended European search report for European Patent Application No. 18890509.5, dated Aug. 3, 2020.
International Search Report and Written Opinion for Application No. PCT/CN2018/120618, dated Mar. 11, 2019.
Chinese Office Action for Application No. 201811517270.4, dated Nov. 20, 2020.
Japanese Office Action for Application No. 2020-534864, dated Jul. 6, 2020.

*Primary Examiner* — Laura L Stockton
(74) *Attorney, Agent, or Firm* — Wolf, Greenfield & Sacks, P.C.

(57) ABSTRACT

Disclosed are a dianilino pyrimidine compound having an inhibitory effect on protein tyrosine kinase, pharmaceutically acceptable salts, crystal forms, prodrugs, metabolites, hydrates, solvates, stereoisomers or isotopic derivatives thereof, a pharmaceutical composition containing these compounds, as well as preparation and use of these compounds. The compound has a structure as represented by formula (I), and may be used for treating ALK-mediated cancer-related symptoms, such as non-small cell lung cancer, breast cancer, nerve tumors, esophagus cancer, soft tissue cancer, lymphoma, or leukemia.

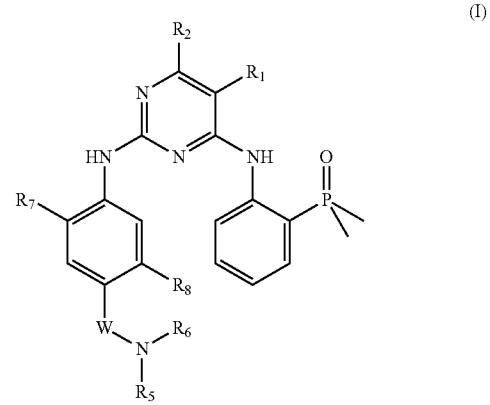

15 Claims, No Drawings

(56) References Cited

FOREIGN PATENT DOCUMENTS

| JP | 2017-521436 A | 8/2017 | |
|----|----|----|----|
| JP | 2021-506937 A | 2/2021 | |
| WO | WO 2009/143389 A1 | 11/2009 | |
| WO | WO-2012/051587 A1 * | 4/2012 | ............ A01N 43/54 |
| WO | WO 2013/169401 A1 | 11/2013 | |

* cited by examiner

DIANILINOPYRIMIDINE COMPOUND FOR INHIBITING KINASE ACTIVITY

CROSS REFERENCE TO RELATED APPLICATIONS

The present application is a national application of PCT/CN2018/120618 filed on Dec. 12, 2018, which claims the priority of the Chinese Patent Application No. 201711395072.0 filed on Dec. 21, 2017.

FIELD OF THE INVENTION

The present disclosure belongs to the technical filed of medicine. Specifically, the present disclosure relates to dianilinopyrimidine compound with inhibitory activity against the protein tyrosine kinase, pharmaceutical compositions containing the same as well as the preparation method and the use thereof.

BACKGROUND OF THE INVENTION

Anaplastic lymphoma kinase (ALK) is a receptor-type protein tyrosine kinase that belongs to the insulin receptor superfamily. It was discovered by Morris and Shiota et al. in 1994 as a product of chromosome rearrangement in anaplastic large cell lymphoma (ALCL). The most frequently found fusion is the one that the NPM (Nucleophosmin) gene on chromosome 5 fuses with the ALK gene on chromosome 2. NPM-ALK fusion protein was detected in nearly 75% of ALK-positive ALCL patients. It was found in subsequent studies that different forms of ALK fusion were present in various cancers, including inflammatory myofibroblastoma and diffuse large B-cell lymphoma. Nevertheless, the importance of ALK kinase as an effective target for anti-tumor drugs has not been fully recognized until in 2007 Soda et al. discovered that the occurrence rate of the EML4-ALK fusion protein in non-small-cell lung cancer (NSCLC) is 5%, and then the importance of ALK kinase as a target for anti-tumor drugs was highlighted. This is because among tremendous cancer patients worldwide, the lung cancer ranks the first. There are more than 8,000 new ALK-positive lung cancer cases each year in the United States, while the new cases each year in China are more than 65,000. The global 5-year survival rate for lung cancer is only 15%. It is interesting to note that EML4-ALK gene-positive patients generally do not carry epidermal growth factor receptor (EGFR) or Kirsten rat sarcoma vims (KRAS) mutations, which makes EML4-ALK fusion gene the unique molecular target for non-small cell lung cancer. In addition, amplification or point mutations of the ALK gene have been found in neuroblastomas, anaplastic thyroid cancer and ovarian cancer.

The first small molecule inhibitor Crizotinib (Xalkori), developed by Pfizer, targets the ALK fusion gene and is the first-generation ALK inhibitors. However, although Crizotinib achieved an objective response rate of 60-74% and a good median progression-free survival (8-11 months) in patients with ALK+NSCLC, most patients experienced disease relapse after 1 year of treatment, that is acquired resistance was generated. The mechanism of the acquired resistance to Crizotinib has also been identified, including the gene gain of the ALK fusion gene, activation of the signaling pathway, secondary mutations in the ALK kinase region, and other mechanisms. About 40% of ALK-positive patients have no objective response at the beginning of receiving Crizotinib therapy, and ⅓ of Crizotinib-resistant patients will undergo secondary mutations that induce secondary resistance.

There are several second-generation ALK inhibitors that may effectively overcome the shortcomings of resistance to Crizotinib therapy, such as Ceritinib (Zykadia, Novartis) and Alectinib (Alecensa, Roche). However, although these second-generation inhibitors may effectively overcome most of Crizotinib-resistant mutations, they are still not effective for some mutations, for example, Ceritinib still has no effect on F1174C/V, Alectinib has no effect on I1171N/T/S, and neither of them has effect on G1202R. So there is an urgent need for developing novel, more effective and safe ALK inhibitors.

SUMMARY OF THE INVENTION

The present disclosure provides a new dianilinopyrimidine compound and a pharmaceutical composition including the same as well as the preparation method and use thereof, which has better ALK kinase inhibitory activity, and high selectivity for drug resistance mutation L1196M, and thus is useful in treating, preventing and alleviating diseases mediated by ALK kinase.

In this regard, the technical solutions of the present disclosure are as follows:

In the first aspect of the present disclosure, a compound of formula (I) is provided:

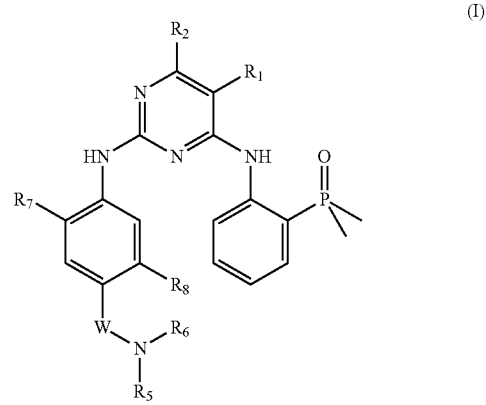

wherein, $R_1$ and $R_2$ are independently selected form H, halogen, —CN, —NO$_2$, —OH, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; or $R_1$ and $R_2$ together with the atoms to which they are attached may form a fused 5-7-membered ring;

Linker W is selected from:

1) $C_1$-$C_6$ alkylene, $C_1$-$C_6$ alkenylene, $C_1$-$C_6$ alkynylene, $C_3$-$C_8$ carbocyclylene, 3- to 10-membered heterocyclylene, $C_6$-$C_{14}$ arylene or 5 to 10-membered heteroarylene; wherein the atom that W connects to the benzene ring must be C; wherein the said group is optionally substituted with one or more $R_3$; or 2) —C(=O)—, —C(=O)O—, or —C(=O)N(R$_4$)—;

$R_3$ is selected from H, halogen, —CN, —NO$_2$, oxo, $C_1$-$C_6$ alkyl, $C_1$-$C_6$ haloalkyl or $C_1$-$C_6$ alkoxy;

$R_4$ is selected from H, $C_1$-$C_6$ alkyl or $C_1$-$C_6$ haloalkyl;

$R_5$ and $R_6$ are independently selected from H, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; or $R_5$ and $R_6$ together with the nitrogen atom to which they are attached form optionally substituted 3- to 10-membered heterocyclyl;

$R_7$ is selected from optionally substituted $C_1$-$C_6$ alkoxy, optionally substituted $C_1$-$C_6$ haloalkoxy, optionally substituted $C_2$-$C_6$ alkenyloxy or optionally substituted 3- to 7-membered cycloalkyloxy;

$R_8$ is selected from H, halogen, —R, —CN, —NO$_2$, —OH, —SH, —C(=O)R, —C(=O)OR, —C(=O)NRR, —NR$_2$, —NRC(=O)R, —NRC(=O)OR, —NRC(=O)NRR, —NRS(=O)R, —NRS(=O)NRR, —NRS(=O)$_2$R, —NRS(=O)$_2$NRR, —OR, —OC(=O)R, —OC(=O)NRR, —S(=O)R, —S(=O)OR, —S(=O)NRR, —S(=O)$_2$R, —S(=O)$_2$OR, —S(=O)$_2$NRR, —SC(=O)R, —SC(=O)OR or —SC(=O)NRR, as long as the chemistry permits; wherein R is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, $C_3$-$C_{10}$ carbocyclyl, 3- to 10-membered heterocyclyl, $C_6$-$C_{14}$ aryl or 5 to 10-membered heteroaryl; two adjacent R may be taken together to form optionally substituted $C_3$-$C_{10}$ carbocyclyl, optionally substituted 5- to 8-membered heterocyclyl, optionally substituted $C_6$-$C_{14}$ aryl or optionally substituted 5 to 10-membered heteroaryl;

or pharmaceutically acceptable salts, crystal forms, prodrugs, metabolites, hydrates, solvates, stereoisomers or isotopic derivatives thereof.

In another aspect, the present disclosure provides a pharmaceutical composition containing a compound of the present disclosure and pharmaceutically acceptable excipient(s). In a specific embodiment, the compound of the present disclosure is provided in the pharmaceutical composition in an effective amount. In a specific embodiment, the compound of the present disclosure is provided in a therapeutically effective amount. In specific embodiments, the compound of the present disclosure is provided in a prophylactically effective amount.

In another aspect, the present disclosure provides a method for preparing a pharmaceutical composition as described above, including the following steps: mixing pharmaceutically acceptable excipient(s) with the compound of the present disclosure to form a pharmaceutical composition.

In another aspect, the present disclosure provides a pharmaceutical composition containing a compound of the present disclosure and pharmaceutically acceptable excipient(s), and other therapeutic agent(s).

In another aspect, the present disclosure provides a method of treating cancer-related disorders caused by ALK mutations in a subject in need thereof, comprising administering to the subject an effective amount of a compound of the present disclosure. In a specific embodiment, the cancer is selected from the group consisting of non-small cell lung cancer, breast cancer, neural tumor (such as glioblastoma and neuroblastoma); esophageal cancer, soft tissue cancer (such as rhabdomyosarcoma and the like); various forms of lymphoma, such as non-Hodgkin's lymphoma (NHL) known as anaplastic large cell lymphoma (ALCL); various forms of leukemia. In an alternative embodiment, the non-small cell lung cancer is ALK positive non-small cell lung cancer. In a specific embodiment, the compound is administered orally, subcutaneously, intravenously, or intramuscularly. In a specific embodiment, the compound is administered for a prolonged period of time.

Other objects and advantages of the present disclosure will be apparent to those skilled in the art from the following specific embodiments, examples, and claims.

Definitions

Chemical Definitions

Definitions of specific functional groups and chemical terms are described in more detail below.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$ and $C_5$-$C_6$ alkyl.

It should be understood that when described herein any of the moieties defined forth below may be substituted by a variety of substituents, and that the respective definitions are intended to include such substituted moieties within their scope as set out below. Unless otherwise stated, the term "substituted" is to be defined as set out below.

"$C_1$-$C_6$ alkyl" refers to a radical of a straight-chain or branched saturated hydrocarbon group having from 1 to 6 carbon atoms, and it is also referred to herein as "lower alkyl". In some embodiments, $C_1$-$C_4$ alkyl is particularly preferred. Examples of alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-6}$ alkyl (e.g., —CH$_3$). In certain embodiments, the alkyl group is substituted $C_{1-6}$ alkyl.

"$C_2$-$C_6$ alkenyl" refers to a radical of a straight-chain or branched hydrocarbon group having from 2 to 6 carbon atoms, one or more carbon-carbon double bonds (e.g., 1, 2, or 3 carbon-carbon double bonds). The one or more carbon-carbon double bonds may be internal (such as in 2-butenyl) or terminal (such as in 1-butenyl). In some embodiments, $C_{2-4}$ alkenyl is particularly preferred. Examples of alkenyl groups include, but are not limited to, ethenyl ($C_2$), 1-propenyl ($C_3$), 2-propenyl ($C_3$), 1-propen-2-yl ($C_3$), 1-butenyl ($C_4$), 2-butenyl ($C_4$), butadienyl ($C_4$), pentenyl ($C_5$), pentadienyl ($C_5$), hexenyl ($C_6$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-6}$ alkenyl. In certain embodiments, the alkenyl group is substituted $C_{2-6}$ alkenyl.

"$C_2$-$C_6$ alkynyl" refers to a radical of a straight-chain or branched hydrocarbon group having from 2 to 6 carbon atoms, one or more carbon-carbon triple bonds (e.g., 1, 2, or 3 carbon-carbon triple bonds), and optionally one or more carbon-carbon double bonds (e.g., 1, 2, or 3 carbon-carbon double bonds). In some embodiments, $C_{2-4}$ alkynyl is particularly preferred. In certain embodiments, alkynyl does not contain any double bonds. The one or more carbon-carbon triple bonds may be internal (such as in 2-butynyl) or terminal (such as in 1-butynyl). Examples of the alkynyl groups include, without limitation, ethynyl ($C_2$), 1-propynyl ($C_3$), 2-propynyl ($C_3$), 1-butynyl ($C_4$), 2-butynyl ($C_4$), pentynyl ($C_5$), 3-methylbut-1-ynyl ($C_5$), hexynyl ($C_6$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-6}$ alkynyl. In certain embodiments, the alkynyl group is substituted $C_{2-6}$ alkynyl.

"$C_1$-$C_6$ alkoxy" refers to the group —OR wherein R is a substituted or unsubstituted $C_1$-$C_6$ alkyl group. In some embodiments, $C_1$-$C_4$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"$C_1$-$C_6$ alkylthio" refers to the group —SR wherein R is optionally substituted $C_1$-$C_6$ alkyl. In some embodiments, $C_1$-$C_4$ alkylthio group is particularly preferred. Specifically, the $C_1$-$C_6$ alkylthio group includes, but is not limited to, methylthio, ethylthio, n-propylthio, isopropylthio, n-butylthio, tert-butylthio, sec-butylthio, n-pentylthio, n-hexylthio and 1,2-dimethylbutylthio.

"$C_1$-$C_6$ alkylamino" refers to the group —NHR or —$NR_2$, wherein R is optionally substituted $C_1$-$C_6$ alkyl. In some embodiments, $C_1$-$C_4$ alkylamino group is particularly preferred. Specifically, the $C_1$-$C_6$ alkylamino group includes, but is not limited to, methylamino, ethylamino, n-propylamino, isopropylamino, n-butylamino, t-butylamino, dimethylamino, methylethylamino and diethylamino.

"$C_1$-$C_6$ alkanoyl" refers to the group —(=O)R, wherein R is optionally substituted $C_1$-$C_6$ alkyl. In some embodiments, $C_1$-$C_4$ alkanoyl group is particularly preferred. Exemplary $C_1$-$C_6$ alkanoyl groups include, but are not limited to, —(=O)$CH_3$, —(=O)$CH_2CH_3$, —(=O)$CH_2CH_2CH_3$ and —(=O)CH($CH_3$)$_2$.

"Halo" or "halogen" means fluorine (F), chlorine (Cl), bromine (Br) and iodine (I). In some embodiments, the halo group is F, —Cl or Br. In some embodiments, the halogen group is F or Cl. In some embodiments, the halogen group is F.

Thus, "$C_1$-$C_6$ haloalkyl" and "$C_1$-$C_6$ haloalkoxy" refer to the above "$C_1$-$C_6$ alkyl" and "$C_1$-$C_6$ alkoxy", which are substituted by one or more halo groups. In some embodiments, $C_1$-$C_4$ haloalkyl group is particularly preferred, and more preferably $C_1$-$C_2$ haloalkyl group. In some embodiments, $C_1$-$C_4$ haloalkoxy group is particularly preferred, and more preferably $C_1$-$C_2$ haloalkoxy group. Exemplary haloalkyl groups include, but are not limited to, —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, and the like. Exemplary haloalkoxy groups include, but are not limited to: —$OCH_2F$, —$OCHF_2$, —$OCF_3$, and the like.

"$C_3$-$C_8$ carbocyclyl" or "3- to 8-membered carbocyclyl" refers to a radical of a non-aromatic cyclic hydrocarbon group having from 3 to 8 ring carbon atoms and zero heteroatoms. In some embodiments, $C_5$-$C_8$ carbocyclyl is preferred, which is a radical of a non-aromatic cyclic hydrocarbon group having from 5 to 8 ring carbon atoms and zero heteroatoms. In some embodiments, $C_3$-$C_6$ carbocyclyl is preferred, which is a radical of a non-aromatic cyclic hydrocarbon group having from 3 to 6 ring carbon atoms and zero heteroatoms. In some embodiments, $C_5$ carbocyclyl is preferred, which is a radical of a non-aromatic cyclic hydrocarbon group having 5 ring carbon atoms and zero heteroatoms. Carbocyclyl also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Exemplary carbocyclyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cyclohexadienyl ($C_6$), as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-8}$ carbocyclyl. In certain embodiments, the carbocyclyl group is a substituted $C_{3-8}$ carbocyclyl.

"3- to 8-membered heterocyclyl" refers to a radical of a 3- to 8-membered non-aromatic ring system having ring carbon atoms and 1 to 3 ring heteroatoms, wherein each heteroatom is independently selected from nitrogen, oxygen, sulfur, boron, phosphorus, and silicon, wherein the carbon, nitrogen, sulfur and phosphorus atoms may be present in the oxidation state, such as C(O), S(O), S(O)$_2$, P(O), and the like. In heterocyclyl groups that contain one or more nitrogen atoms, the point of attachment may be a carbon or nitrogen atom, as valency permits. In some embodiments, 4- to 7-membered heterocyclyl is preferred, which is a radical of a 4- to 7-membered non-aromatic ring system having ring carbon atoms and 1 to 3 ring heteroatoms. In some embodiments, 5- to 8-membered heterocyclyl is preferred, which is a radical of a 5- to 8-membered non-aromatic ring system having ring carbon atoms and 1 to 3 ring heteroatoms. In some embodiments, 4- to 6-membered heterocyclyl is preferred, which is a radical of a 4- to 6-membered non-aromatic ring system having ring carbon atoms and 1 to 3 ring heteroatoms. In some embodiments, 5- to 6-membered heterocyclyl is preferred, which is a radical of a 5- to 6-membered non-aromatic ring system having ring carbon atoms and 1 to 3 ring heteroatoms. In some embodiments, 5-membered heterocyclyl is more preferred, which is a radical of a 5-membered non-aromatic ring system having ring carbon atoms and 1 to 3 ring heteroatoms. In some embodiments, the 3- to 8-membered heterocyclyl, 4- to 7-membered heterocyclyl, 5- to 8-membered heterocyclyl, 4- to 6-membered heterocyclyl, 5- to 6-membered heterocyclyl and 5-membered heterocyclyl contain 1 to 3 (more preferably 1 or 2) ring heteroatoms selected from nitrogen, oxygen and sulfur (preferably nitrogen and oxygen). Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-8 membered heterocyclyl. In certain embodiments, the heterocyclyl group is substituted 3-8 membered heterocyclyl. Heterocyclyl also includes ring systems wherein the heterocyclyl ring, as defined above, is fused with one or more carbocyclyl groups wherein the point of attachment is on the carbocyclyl ring, or ring systems wherein the heterocyclyl ring, as defined above, is fused with one or more aryl or heteroaryl groups, wherein the point of attachment is on the heterocyclyl ring; and in such instances, the number of ring members continue to designate the number of ring members in the heterocyclyl ring system. Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxathiolanyl, oxathiolyl (1,2-oxathiolyl, 1,3-oxathiolyl), dithiolanyl, dihydropyrazolyl, dihydroimidazolyl, dihydrothiazolyl, dihydroisothiazolyl, dihydrooxazolyl, dihydroisoxazolyl, dihydrooxadiazolyl and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, tetrahydropyridinyl, and thianyl. Exemplary 6-membered heterocyclyl groups containing two heteroatoms include, without limitation, dihydropyrazinyl, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one or two heteroatoms include, without limitation, azepanyl, diazepanyl, oxepanyl and thiepanyl. Exemplary 8-membered heterocyclyl groups containing one or two heteroatoms include, without limitation, azocanyl, oxecanyl, thiocanyl, octahydrocyclopenta[c]pyrrolyl and octahydropyrrolo[3,4-c]pyrrolyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an $C_6$ aryl ring (also referred to herein as a 6,6-bicyclic heterocyclic ring) include, without limitation, tetrahydroquinolinyl, tetrahydroisoquinolinyl, and the like.

"$C_6$-$C_{14}$ aryl" or "6- to 14-membered aromatic radical" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "$C_6$-$C_{14}$ aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"5- to 10-membered heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur. In some embodiments, 5-membered heteroaryl is preferred, which is a radical of a 5-membered monocyclic 4n+2 aromatic ring system (e.g., having 6 π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment may be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5- to 10-membered heteroaryl. In certain embodiments, the heteroaryl group is substituted 5- to 10-membered heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, perhaloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted by 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from alkyl, perhaloalkyl, alkenyl, alkynyl, carbocyclyl, heterocyclyl, aryl, and heteroaryl, or two R$^{aa}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, perhaloalkyl, alkenyl, alkynyl, carbocyclyl, heterocyclyl, aryl, and heteroaryl, or two R$^{bb}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups;

each instance of R$^{cc}$ is, independently, selected from hydrogen, alkyl, perhaloalkyl, alkenyl, alkynyl, carbocyclyl, heterocyclyl, aryl, and heteroaryl, or two R$^{cc}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, perhaloalkyl, alkenyl, alkynyl, carbocyclyl, heterocyclyl, aryl, heteroaryl, wherein each alkyl, alkenyl, alkynyl, carbocyclyl, heterocyclyl, aryl, and heteroaryl is independently substituted by 0, 1, 2, 3, 4, or 5 R$^{gg}$ groups, or two geminal R$^{dd}$ substituents may be joined to form =O or =S;

each instance of R$^{ee}$ is, independently, selected from alkyl, perhaloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted by 0, 1, 2, 3, 4, or 5 R$^{gg}$ groups;

each instance of R$^{ff}$ is, independently, selected from hydrogen, alkyl, perhaloalkyl, alkenyl, alkynyl, carbocyclyl, heterocyclyl, aryl and heteroaryl, or two R$^{ff}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents may be joined to form =O or =S; wherein X$^-$ is a counterion.

Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$_{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)2, —SO$_2$N(R$^{cc}$)2, —SO$_2$R$^{cc}$, —SO$_2$OR$^{cc}$, —SOR$^{aa}$, —C(=S)N(R$^{cc}$)2, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)2, —P(=O)(NR$^{cc}$)2, alkyl, perhaloalkyl, alkenyl, alkynyl, carbocyclyl, heterocyclyl, aryl, and heteroaryl, or two R$^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups, and wherein R$^{aa}$, R$^{bb}$, R$^{cc}$ and R$^{dd}$ are as defined above.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a therapeutic agent of the present disclosure. For example, a compound disclosed herein may be administered simultaneously or sequentially with another therapeutic agent in separate unit dosage forms, or together with another therapeutic agent in a single unit dosage form.

Specific Embodiments of the Disclosure Compound

The "compound of the present disclosure" used herein refers to the following compounds of formula (I), and their pharmaceutically acceptable salts, crystal forms, prodrugs, metabolites, hydrates, solvates, stereoisomers or isotopic derivatives thereof.

In one embodiment, the present disclosure relates to a compound of formula (I):

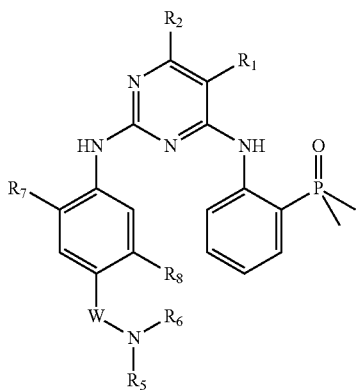

(I)

wherein, $R_1$ and $R_2$ are independently selected from H, halogen, —CN, —NO$_2$, —OH, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; or $R_1$ and $R_2$ together with the atoms to which they are attached may form a fused 5- to 7-membered ring;

Linker W is selected from:

1) $C_1$-$C_6$ alkylene, $C_1$-$C_6$ alkenylene, $C_1$-$C_6$ alkynylene, $C_3$-$C_8$ carbocyclylene, 3- to 10-membered heterocyclylene, $C_6$-$C_{14}$ arylene or 5 to 10-membered heteroarylene; wherein the atom that W connects to the benzene ring must be C; wherein the said group is optionally substituted with one or more $R_3$; or 2) —C(=O)—, —C(=O)O—, or —C(=O)N($R_4$)—;

$R_3$ is selected from H, halogen, —CN, —NO$_2$, oxo, $C_1$-$C_6$ alkyl, $C_1$-$C_6$ haloalkyl or $C_1$-$C_6$ alkoxy;

$R_4$ is selected from H, $C_1$-$C_6$ alkyl or $C_1$-$C_6$ haloalkyl;

$R_5$ and $R_6$ are independently selected from H, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; or $R_5$ and $R_6$ together with the nitrogen atom to which they are attached form optionally substituted 3- to 10-membered heterocyclyl;

$R_7$ is selected from optionally substituted $C_1$-$C_6$ alkoxy, optionally substituted $C_1$-$C_6$ haloalkoxy, optionally substituted $C_2$-$C_6$ alkenyloxy or optionally substituted 3- to 7-membered cycloalkyloxy;

$R_8$ is selected from H, halogen, —R, —CN, —NO$_2$, —OH, —SH, —C(=O)R, —C(=O)OR, —C(=O)NRR, —NR$_2$, —NRC(=O)R, —NRC(=O)OR, —NRC(=O)NRR, —NRS(=O)R, —NRS(=O)NRR, —NRS(=O)$_2$R, —NRS(=O)$_2$NRR, —OR, —OC(=O)R, —OC(=O)NRR, —S(=O)R, —S(=O)OR, —S(=O)NRR, —S(=O)$_2$R, —S(=O)$_2$OR, —S(=O)$_2$NRR, —SC(=O)R, —SC(=O)OR or —SC(=O)NRR, as long as the chemistry permits; wherein R is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, $C_3$-$C_{10}$ carbocyclyl, 3- to 10-membered heterocyclyl, $C_6$-$C_{14}$ aryl or 5 to 10-membered heteroaryl; two adjacent R may be taken together to form optionally substituted $C_3$-$C_{10}$ carbocyclyl, optionally substituted 5- to 8-membered heterocyclyl, optionally substituted $C_6$-$C_{14}$ aryl or optionally substituted 5 to 10 heteroaryl;

or pharmaceutically acceptable salts, crystal forms, prodrugs, metabolites, hydrates, solvates, stereoisomers or isotopic derivatives thereof.

In such embodiment, alternatively, $R_2$ is independently selected from H, halogen, —CN, —NO$_2$, —OH, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; alternatively, $R_1$ is selected from H, halogen, —CN, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; alternatively, $R_1$ is selected from H, F, Cl, Br, methyl, ethyl, isopropyl, —CH$_2$F, —CHF$_2$, methoxy, isopropoxy, cyclopropyl or oxiranyl; yet alternatively, $R_1$ is selected from H, F, Cl, methyl, isopropyl or cyclopropyl; yet alternatively, $R_1$ is selected from Cl.

In such embodiment, alternatively, $R_2$ is independently selected from H, halogen, —CN, —NO$_2$, —OH, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; alternatively, $R_2$ is selected from H, halogen, —CN, —NO$_2$, —OH, optionally substituted $C_1$-$C_6$ alkyl, or optionally substituted $C_1$-$C_6$ alkoxy; alternatively, $R_2$ is selected from H, F, Cl, Br, —CN, —NO$_2$, —OH or methyl; yet alternatively, $R_2$ is H.

In such embodiment, alternatively, $R_1$ and $R_2$ together with the atoms to which they are attached may form a fused 5- to 7-membered ring; alternatively, $R_1$ and $R_2$ together with the carbon atoms to which they are attached may form a fused 5- to 7-membered aromatic ring, which comprises 0 to 2 heteroatoms selected from N, O and S; alternatively, $R_1$ and $R_2$ together with the carbon atoms to which they are attached may form a fused 5-membered aromatic ring, which comprises 0 to 2 heteroatoms selected from N and S; alternatively, R1 and R2 together with the carbon atoms to which they are attached may form a fused pyrrole ring, pyrazole ring, imidazole ring, thiophene ring or furan ring.

In such embodiment, alternatively, linker W is selected from:

1) $C_1$-$C_6$ alkylene, $C_1$-$C_6$ alkenylene, $C_1$-$C_6$ alkynylene, $C_3$-$C_8$ carbocyclylene, 3- to 10-membered heterocyclylene, $C_6$-$C_{14}$ arylene or 5 to 10-membered heteroarylene; wherein the atom that W connects to the benzene ring must be C; wherein the said group is optionally substituted with one or more $R_3$; or 2) —C(=O)—, —C(=O)O—, or —C(=O)N($R_4$)—;

alternatively, W is selected from:

1) $C_1$-$C_6$ alkylene, $C_3$-$C_{10}$ carbocyclylene, or 3- to 10-membered heterocyclylene, wherein the atom that W connects to the benzene ring must be C; wherein the said group is optionally substituted with one or more $R_3$; or 2) —C(=O)—, —C(=O)O—, or —C(=O)N($R_4$)—;

yet alternatively, W is selected from:

1) —CH$_2$—, —CH$_2$CH$_2$—, —C(CH$_3$)H—, —C(CH$_3$)$_2$—, —C(CH$_3$)HCH$_2$—, —C(CH$_3$)$_2$CH$_2$—, —C(CH$_3$)HC(CH$_3$)H—, —C(CH$_3$)$_2$C(CH$_3$)$_2$—,

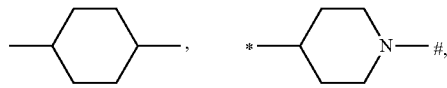

-continued

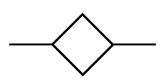 or 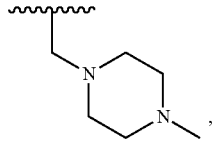

wherein * represents the connection to benzene ring, # represents the connection to nitrogen atom; or

2) —C(=O)—.

In such embodiment, alternatively, $R_5$ and $R_6$ are independently selected from H, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; or $R_5$ and $R_6$ together with the nitrogen atom to which they are attached may form optionally substituted 3- to 10-membered heterocyclyl; alternatively, $R_5$ and $R_6$ is independently selected from H, optionally substituted $C_1$-$C_6$ alkyl, optionally substituted $C_3$-$C_{10}$ carbocyclyl or optionally substituted 3- to 10-membered heterocyclyl; or $R_5$ and $R_6$ together with the nitrogen atom to which they are attached may form optionally substituted 3- to 10-membered heterocyclyl; yet alternatively, $R_5$ and $R_6$ are independently selected from H, methyl or ethyl, or $R_5$ and $R_6$ together with the nitrogen atom to which they are attached may form optionally substituted 3-membered, 4-membered, 5-membered or 6-membered heterocyclyl.

In such embodiment, alternatively, —W—$NR_5R_6$ is selected from:

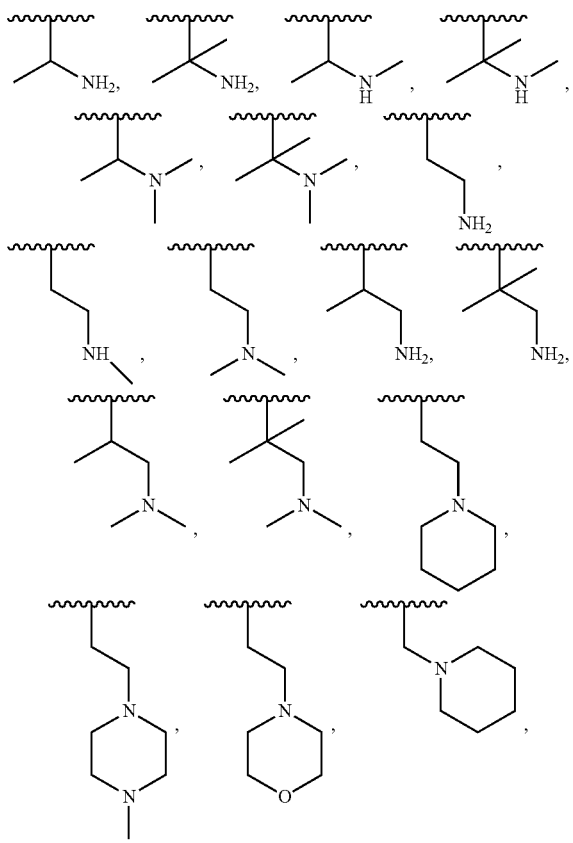

-continued

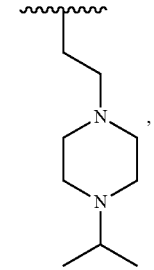
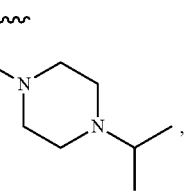
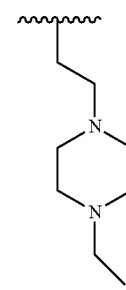
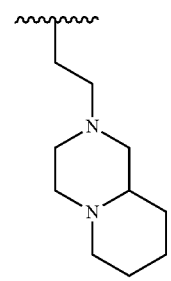
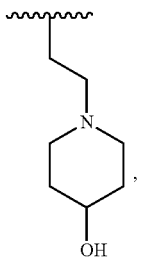
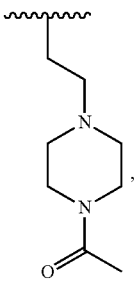
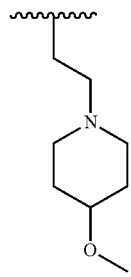
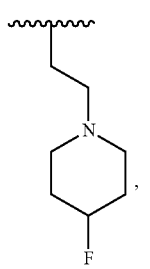
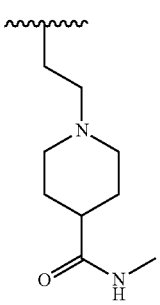
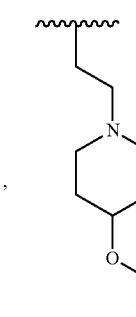
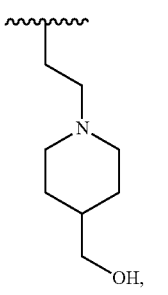
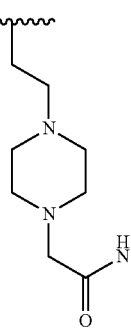
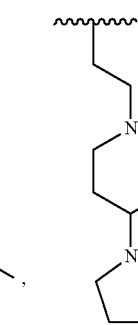

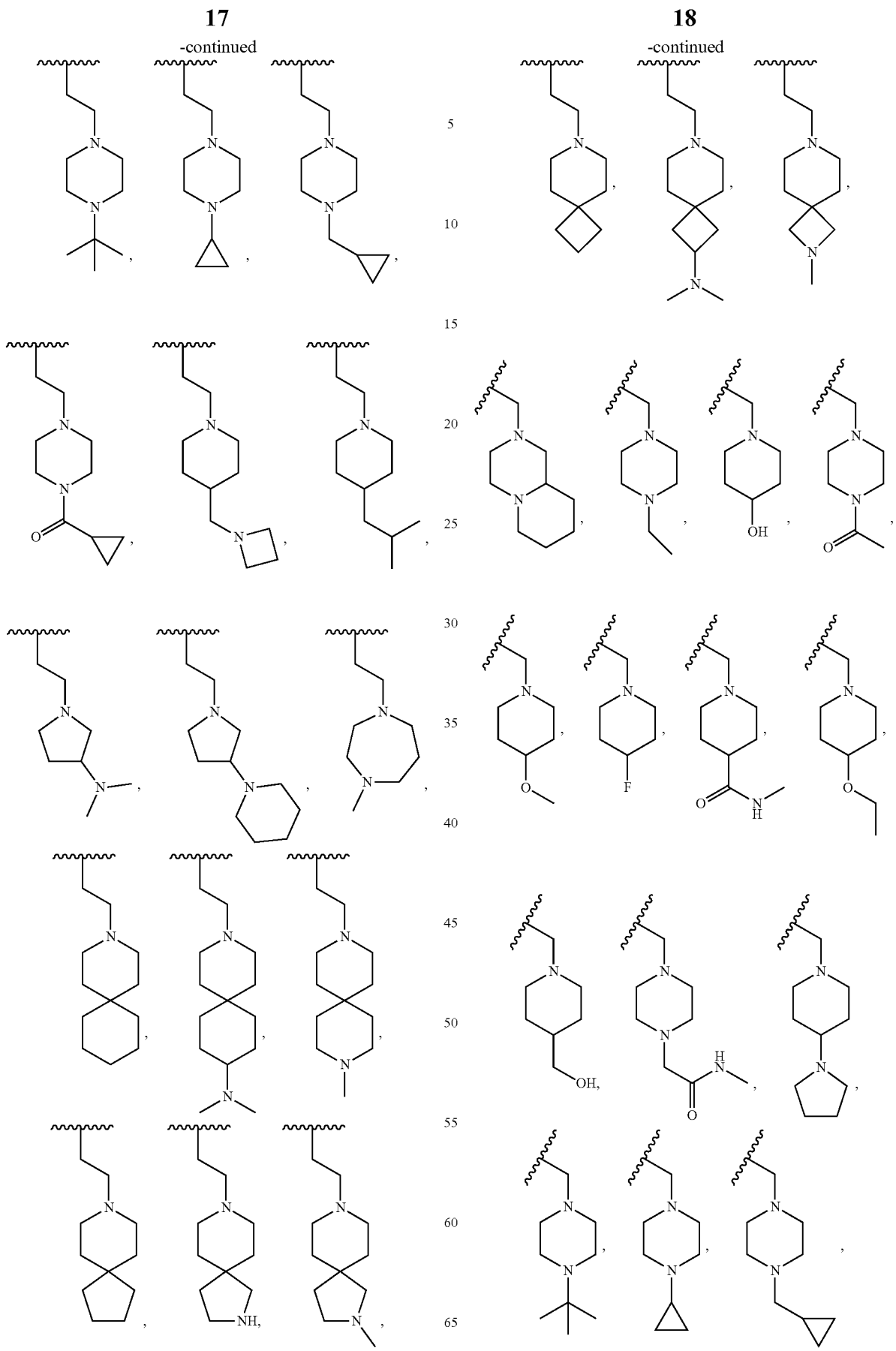

-continued
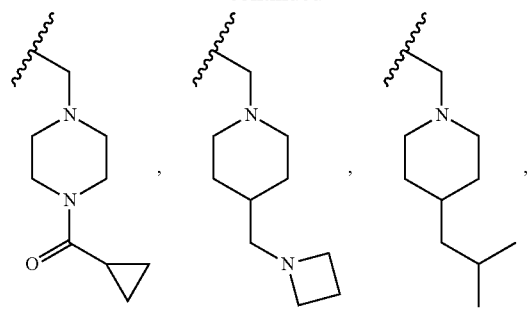
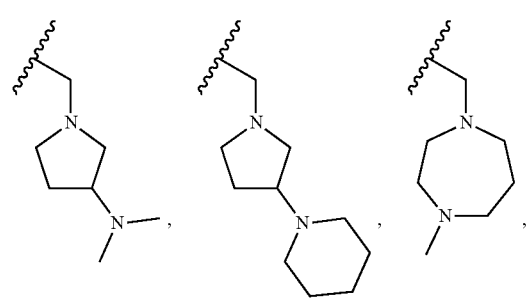
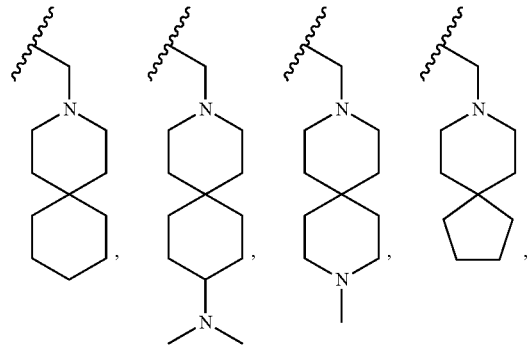
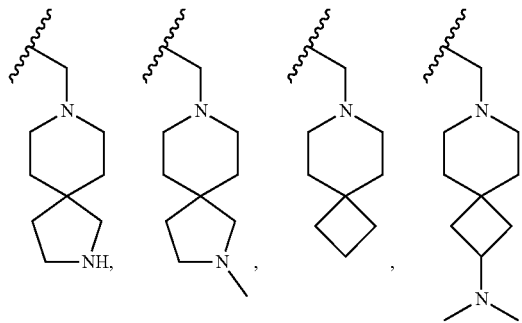
-continued
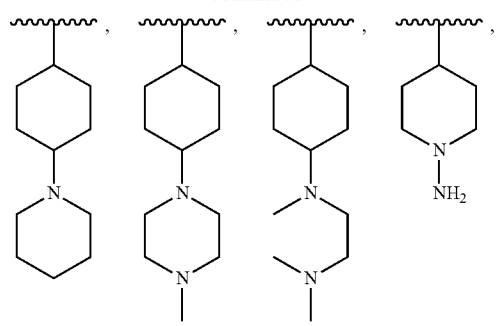
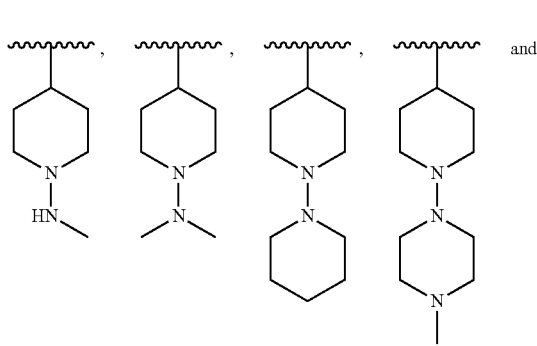
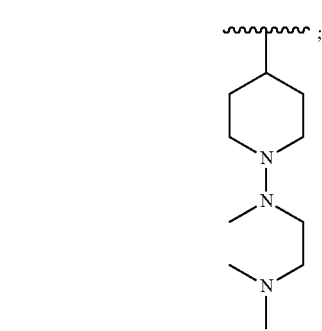
alternatively, —W—NR$_5$R$_6$ is selected from:
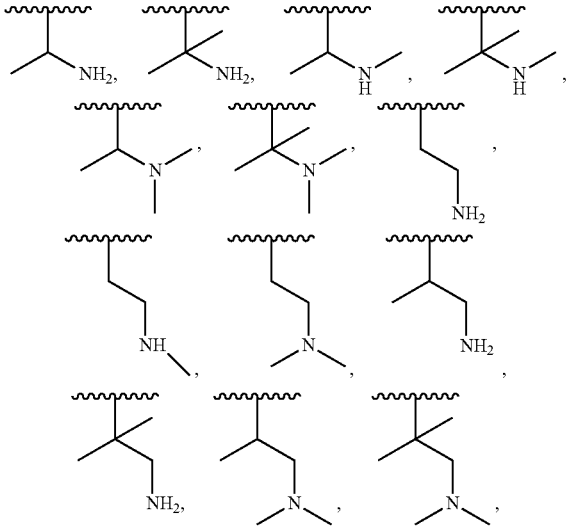

-continued

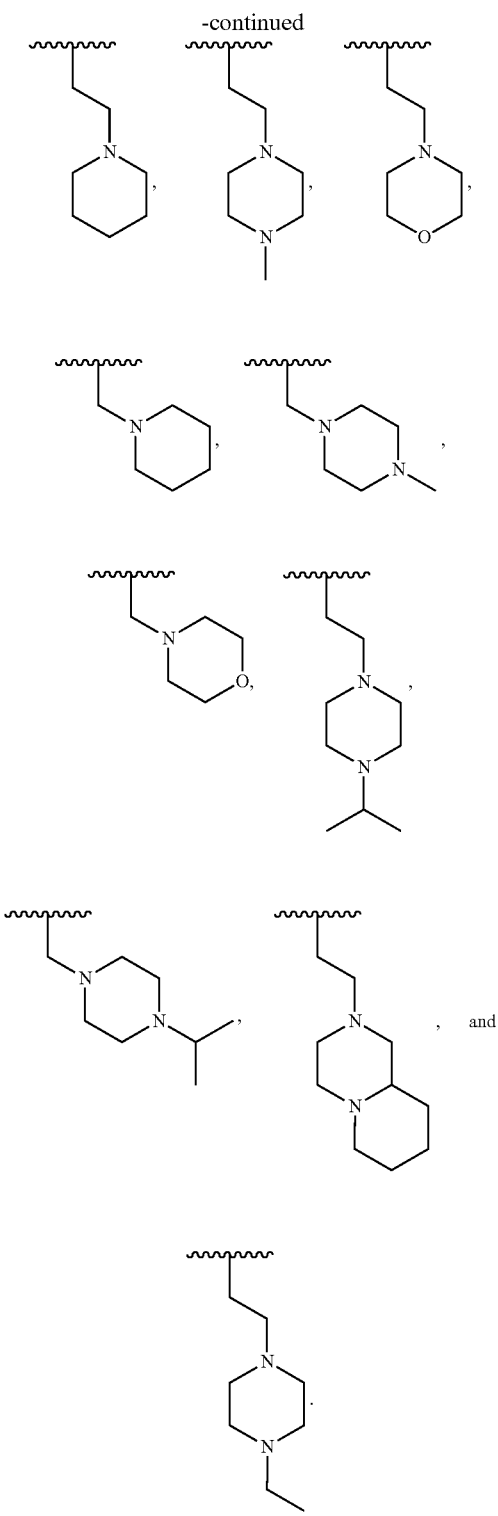

In such embodiment, alternatively, $R_7$ is selected from optionally substituted $C_1$-$C_6$ alkoxy, optionally substituted $C_1$-$C_6$ haloalkoxy, optionally substituted $C_2$-$C_6$ alkenyloxy or optionally substituted 3- to 7-membered cycloalkyloxy; alternatively, $R_7$ is selected from optionally substituted $C_1$-$C_6$ alkoxy, optionally substituted $C_1$-$C_6$ haloalkoxy; alternatively, $R_2$ is selected from —OCH$_3$, —OCH$_2$CH$_3$, —OCH$_2$CH$_2$CH$_3$, —OCH(CH$_3$)$_2$, —OCF$_3$, —OCHF$_2$, —OCH$_2$F or —OCH$_2$CF$_3$; yet alternatively, $R_2$ is selected from —OCH$_3$, —OCH(CH$_3$)$_2$ or —OCH$_2$CF$_3$; most alternatively, $R_2$ is —OCH$_3$.

In such embodiment, alternatively, $R_8$ is selected from H, halogen, —R, —CN, —NO$_2$, —OH, —SH, —C(=O)R, —C(=O)OR, —C(=O)NRR, —NR$_2$, —NRC(=O)R, —NRC(=O)OR, —NRC(=O)NRR, —NRS(=O)R, —NRS(=O)NRR, —NRS(=O)$_2$R, —NRS(=O)$_2$NRR, —OR, —OC(=O)R, —OC(=O)NRR, —S(=O)R, —S(=O)OR, —S(=O)NRR, —S(=O)$_2$R, —S(=O)$_2$OR, —S(=O)$_2$NRR, —SC(=O)R, —SC(=O)OR or —SC(=O)NRR, as long as the chemistry permits; wherein R is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, $C_3$-$C_{10}$ carbocyclyl, 3- to 10-membered heterocyclyl, $C_6$-$C_{14}$ aryl or 5 to 10-membered heteroaryl; two adjacent R may be taken together to form optionally substituted $C_3$-$C_{10}$ carbocyclyl, optionally substituted 5- to 8-membered heterocyclyl, optionally substituted $C_6$-$C_{14}$ aryl or optionally substituted 5 to 10 heteroaryl; $R_8$ is selected from H, R, halogen, —CN, —C(=O)R, —C(=O)OR, —C(=O)NRR, —NR$_2$, —NRC(=O)R, —NRC(=O)OR, —NRC(=O)NRR, —OR, —OC(=O)R, —OC(=O)NRR, as long as the chemistry permits; wherein R is independently H, halogen, $C_1$-$C_6$ alkyl, $C_1$-$C_6$ haloalkyl, $C_1$-$C_6$ alkoxy, $C_1$-$C_6$ alkenyl, $C_1$-$C_6$ alkynyl, $C_3$-$C_{10}$ carbocyclyl or 3- to 10-membered heterocyclyl; two adjacent R may be taken together to form optionally substituted $C_3$-$C_{10}$ carbocyclyl, optionally substituted 5- to 8-membered heterocyclyl; alternatively, $R_8$ is selected from H, F, Cl, Br, methyl, —C(=O)CH$_3$, —C(=O)OCH$_3$, —C(=O)N(CH$_3$)$_2$, —N(CH$_3$)$_2$, —N(CH$_3$)C(=O)(CH=CH$_2$) or —OC(=O)N(CH$_3$)$_2$; yet alternatively, $R_8$ is selected from H or methyl.

In another embodiment, the disclosure relates to a compound of formulae (IIa) to (IIm):

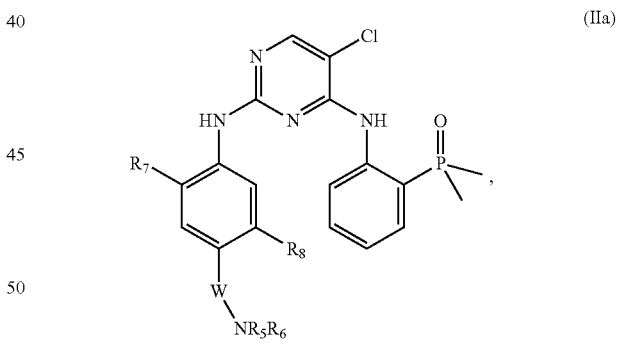

(IIa)

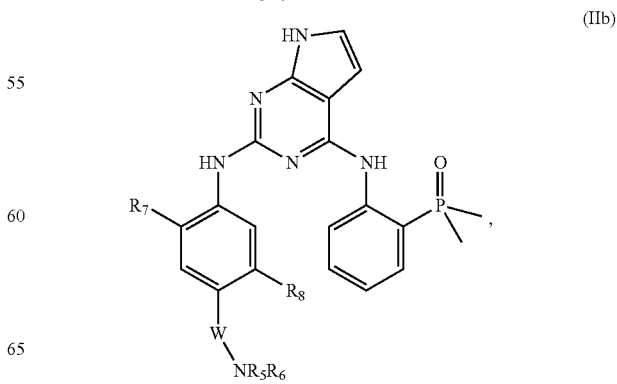

(IIb)

-continued
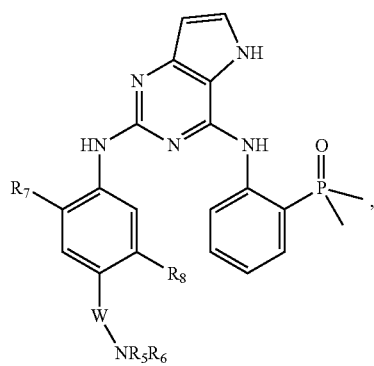
(IIc)
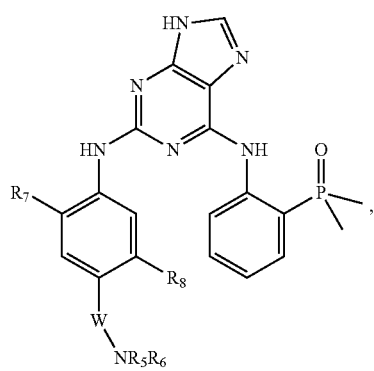
(IId)
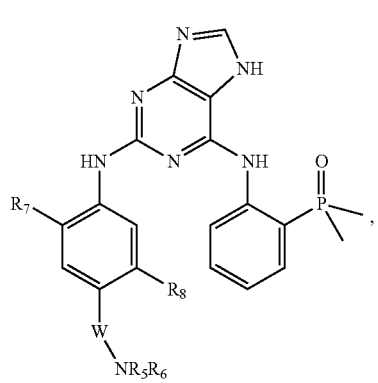
(IIe)
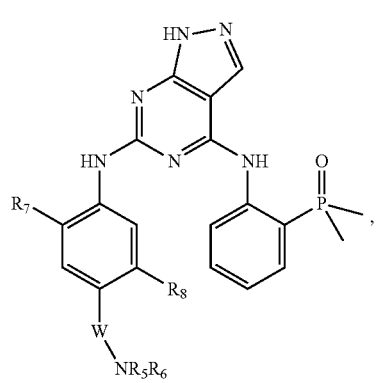
(IIf)
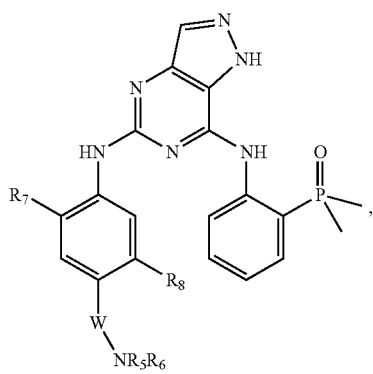
(IIg)
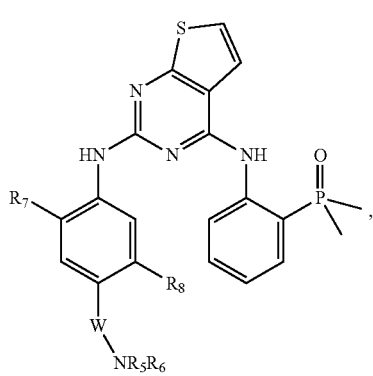
(IIh)
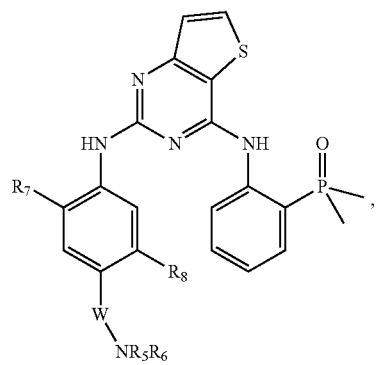
(IIj)
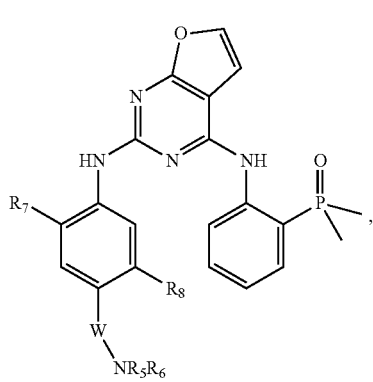
(IIk)

(IIm)
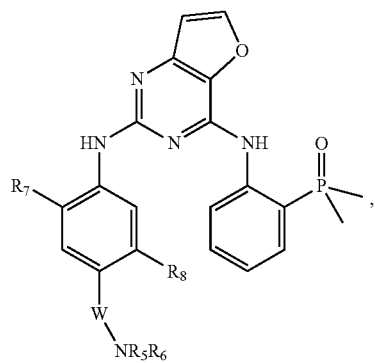
wherein $R_5$, $R_6$, $R_7$, $R_8$ and W are defined as above.
In another preferred embodiment, the disclosure relates to a compound of formulae (IIa) to (IIm):
(IIa)
(IIb)
(IIc)
(IId)
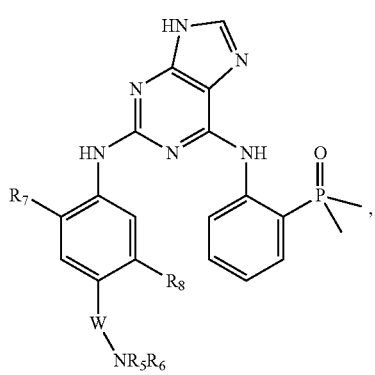
(IIe)
(IIf)
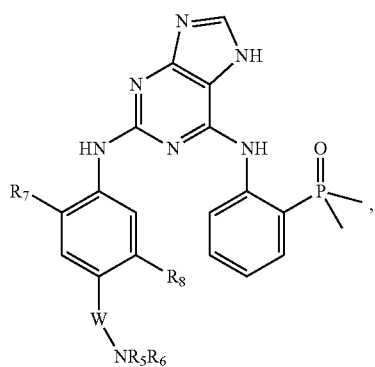
(IIg)
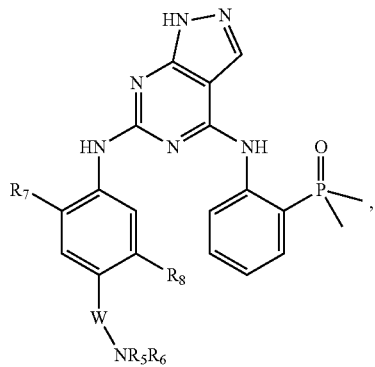
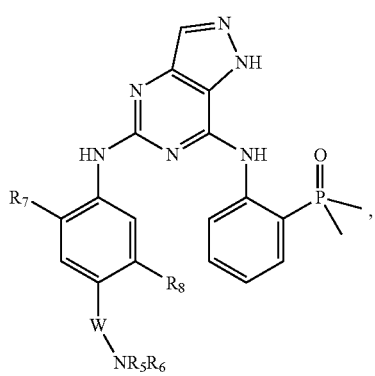

-continued (IIh)
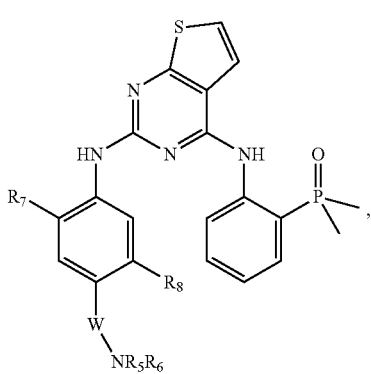

(IIj)
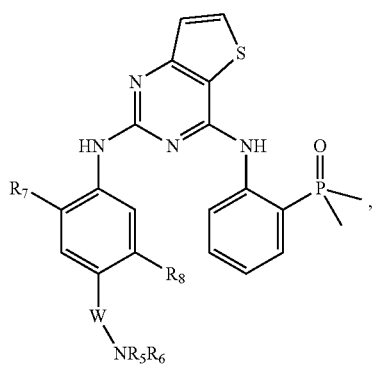

(IIk)
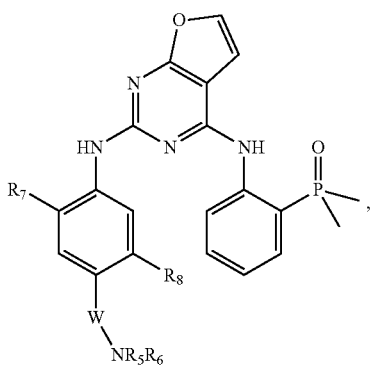

(IIm)
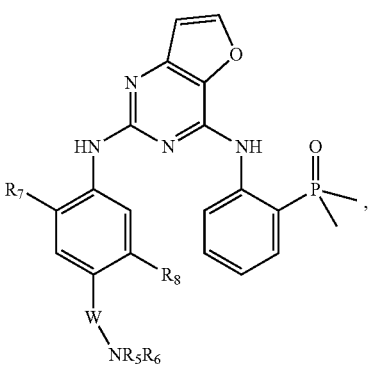

wherein,

W is selected from $C_1$-$C_6$ alkylene, $C_3$-$C_{10}$ carbocyclylene, 3- to 10-membered heterocyclylene, wherein the atom that W connects to the benzene ring must be C; wherein the said group is optionally substituted with one or more $R_3$;

$R_3$ is selected from H, $C_1$-$C_6$ alkyl, $C_1$-$C_6$ haloalkyl or $C_{1-6}$ alkoxy;

$R_5$ and $R_6$ is independently selected from H, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl or optionally substituted 3- to 10-membered heterocyclyl; or $R_5$ and $R_6$ together with the nitrogen atom to which they are attached may form optionally substituted 3- to 10-membered heterocyclyl;

$R_7$ is selected from optionally substituted $C_1$-$C_6$ alkoxy, optionally substituted $C_1$-$C_6$ haloalkoxy or optionally substituted 3- to 7-membered cycloalkyloxy;

$R_8$ is selected from H, halogen or $C_1$-$C_6$ alkyl;

or pharmaceutically acceptable salts, crystal forms, prodrugs, metabolites, hydrates, solvates, stereoisomers or isotopic derivatives thereof.

In some embodiments, W is selected from $C_1$-$C_6$ alkylene, $C_3$-$C_{10}$ carbocyclylene, 3- to 10-membered heterocyclylene, wherein the atom that W connects to the benzene ring must be C; wherein the said group is optionally substituted with one or more $R_3$; wherein, $R_3$ is selected from H or $C_1$-$C_6$ alkyl;

alternatively, W is $C_1$-$C_6$ alkylene, which is optionally substituted with one or more $R_3$; wherein, $R_3$ is selected from H or $C_1$-$C_6$ alkyl; alternatively, W is selected from —$CH_2$—, —$CH_2CH_2$—, —$C(CH_3)H$—, —$C(CH_3)_2$—, —$C(CH_3)HCH_2$—, —$C(CH_3)_2CH_2$—, —$C(CH_3)HC(CH_3)H$— or —$C(CH_3)_2C(CH_3)_2$—;

alternatively, W is $C_3$-$C_{10}$ carbocyclylene, which is optionally substituted with one or more $R_3$; wherein, $R_3$ is selected from H or $C_1$-$C_6$ alkyl; alternatively, W is selected from

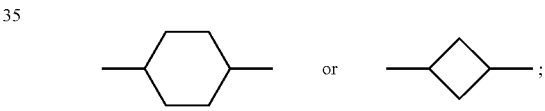

alternatively, W is 3- to 10-membered heterocyclylene, wherein the atom that W connects to the benzene ring must be C; wherein the said group is optionally substituted with one or more $R_3$; wherein, $R_3$ is selected from H or $C_1$-$C_6$ alkyl; alternatively, W is selected from

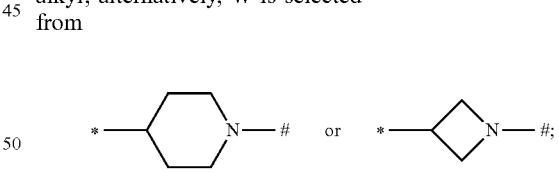

wherein * represents the connection to benzene ring, # represents the connection to N.

In some embodiments, alternatively, $R_5$ and $R_6$ is independently selected from H, optionally substituted $C_1$-$C_6$ alkyl, optionally substituted $C_3$-$C_{10}$ carbocyclyl or optionally substituted 3- to 10-membered heterocyclyl; or $R_5$ and $R_6$ together with the nitrogen atom to which they are attached may form optionally substituted 3- to 10-membered heterocyclyl;

alternatively, $R_5$ and $R_6$ is independently selected from H or optionally substituted $C_1$-$C_6$ alkyl; or $R_5$ and $R_6$ together with the nitrogen atom to which they are attached may form optionally substituted 3- to 10-membered heterocyclyl;

In some embodiments, alternatively, —W—$NR_5R_6$ is selected from:

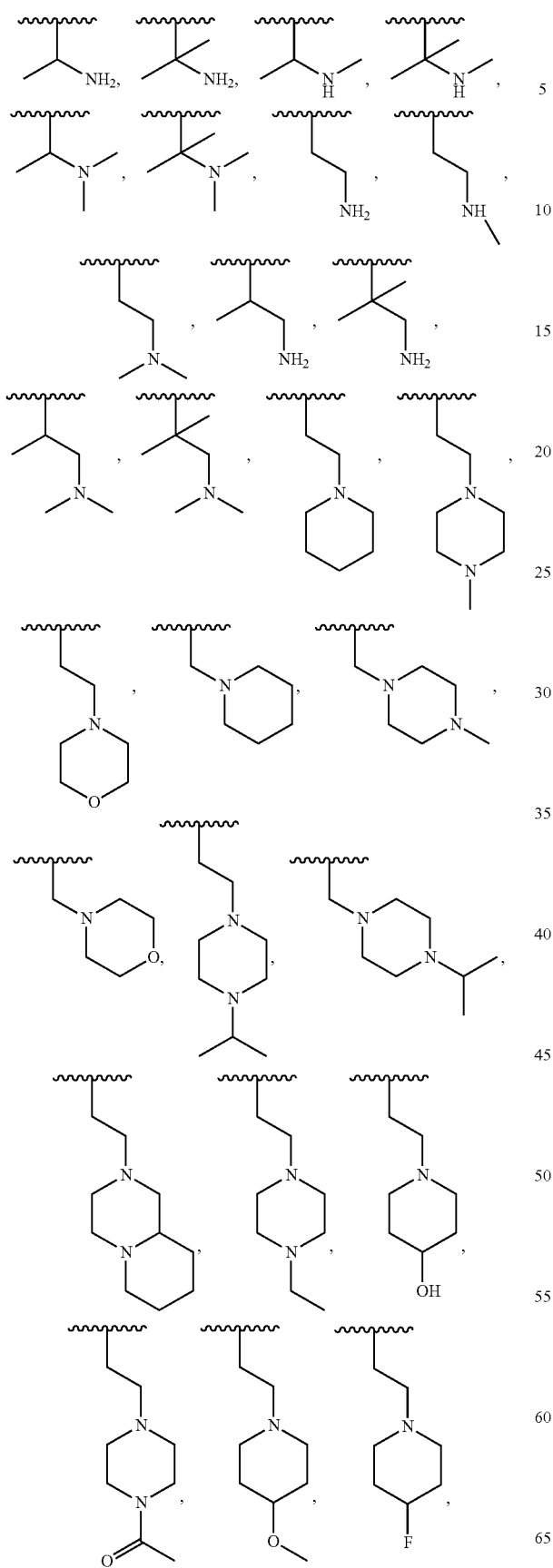
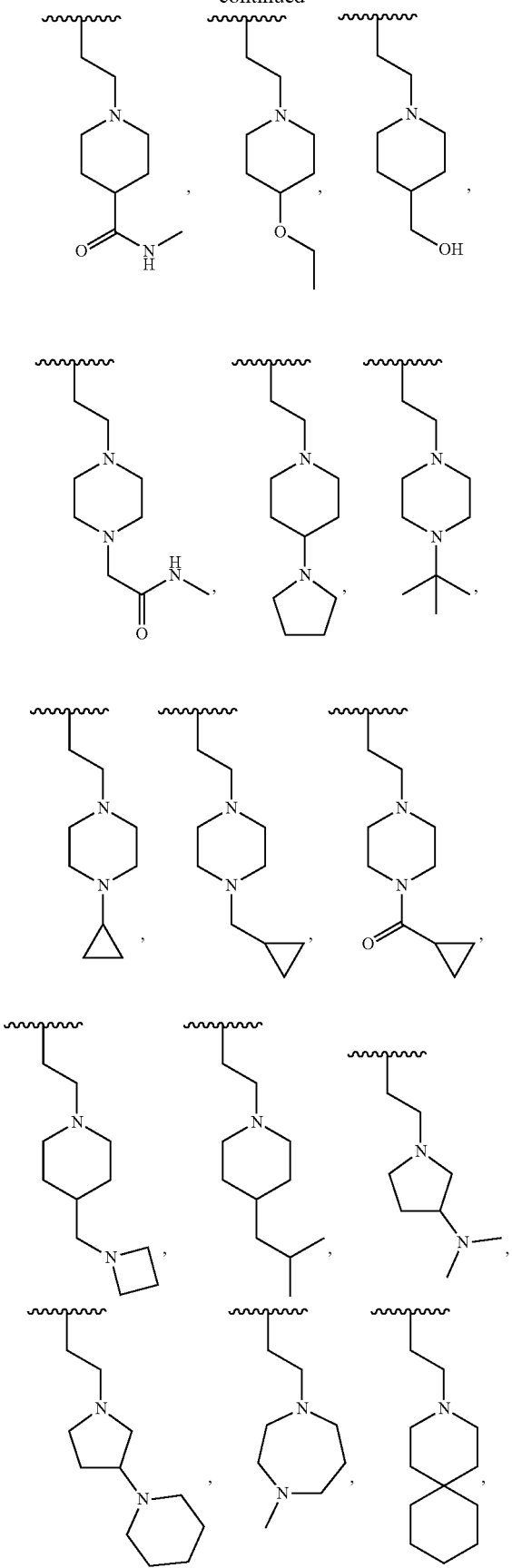

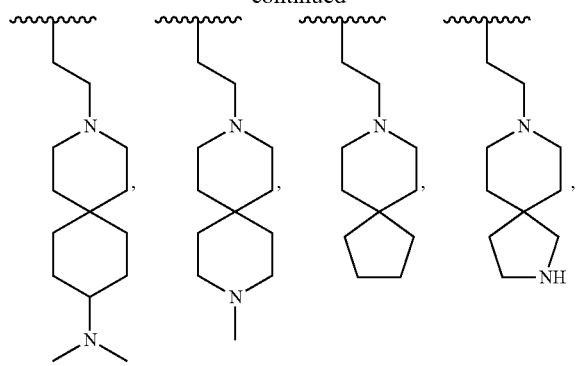
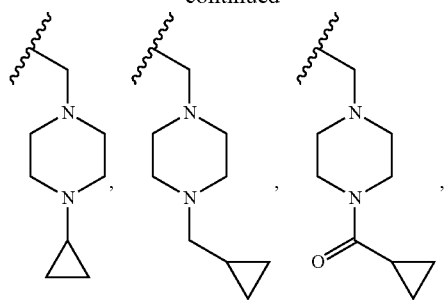
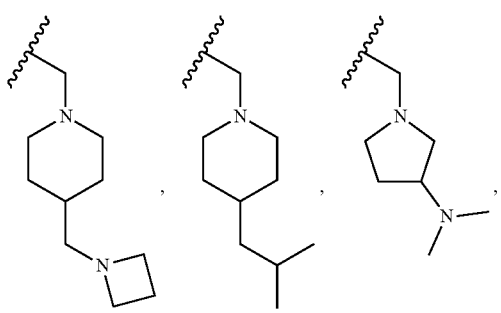
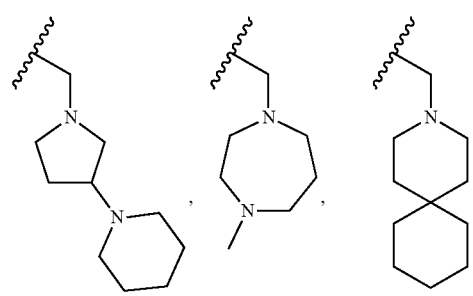
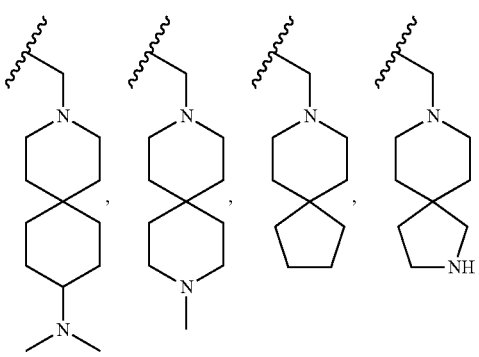
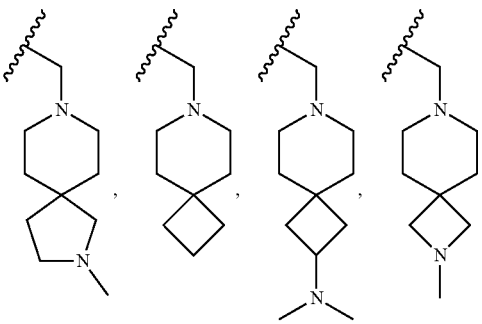

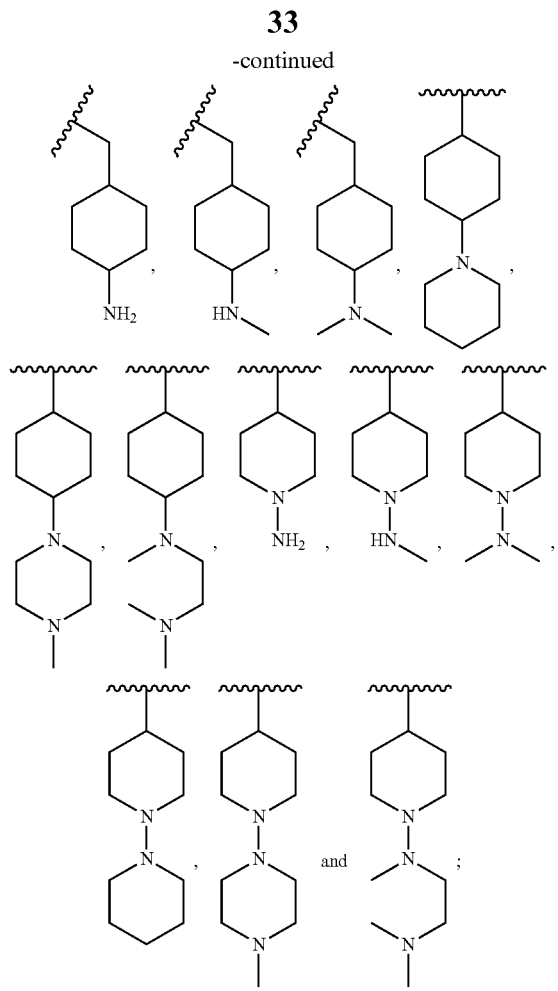

alternatively, —W—NR₅R₆ is selected from:

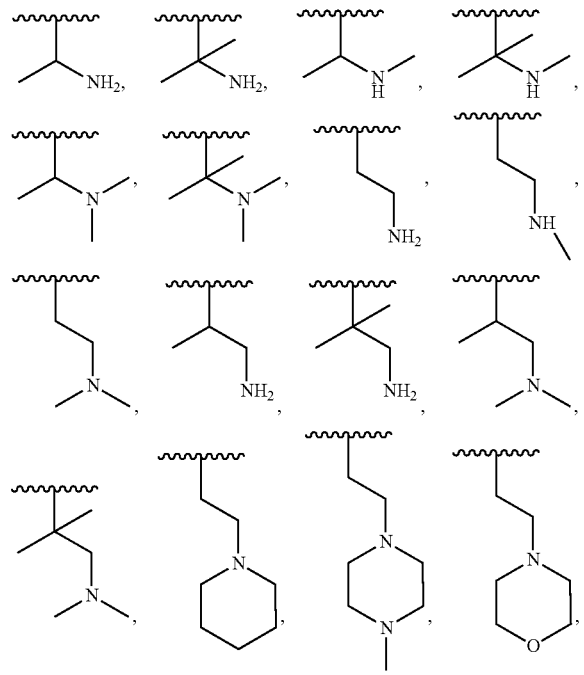

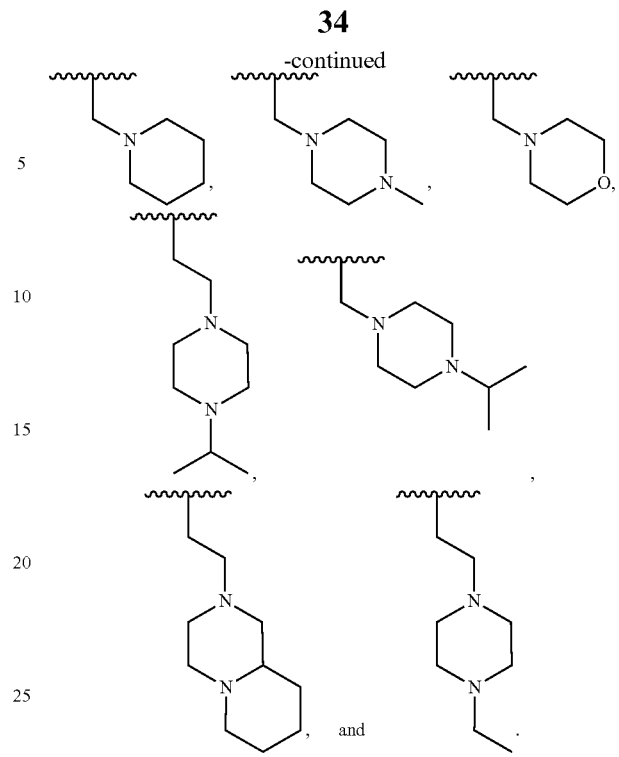

In some embodiments, alternatively, $R_7$ is optionally substituted $C_1$-$C_6$ alkoxy; alternatively, $R_7$ is —OCH₃.

In some embodiments, alternatively, $R_8$ is selected from H or $C_1$-$C_6$ alkyl; alternatively, $R_8$ is selected from H or methyl.

In another preferred embodiment, the present disclosure relates to a compound of formula (IIa):

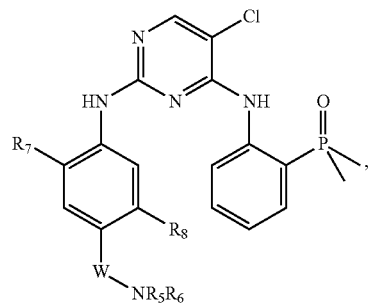

(IIa)

wherein,

W is $C_1$-$C_6$ alkylene; wherein the said group is optionally substituted with one or more $R_3$;

$R_3$ is selected from H or $C_1$-$C_6$ alkyl;

$R_5$ and $R_6$ is independently selected from H or optionally substituted $C_1$-$C_6$ alkyl; or $R_5$ and $R_6$ together with the nitrogen atom to which they are attached may form optionally substituted 5 to 6-membered heterocyclyl;

$R_7$ is optionally substituted $C_1$-$C_6$ alkoxy;

$R_8$ is selected from H or $C_1$-$C_6$ alkyl;

or pharmaceutically acceptable salts, crystal forms, prodrugs, metabolites, hydrates, solvates, stereoisomers or isotopic derivatives thereof.

In some embodiments, alternatively, W is selected from —CH₂—, —CH₂CH₂—, —C(CH₃)H—, —C(CH₃)₂—, —C(CH₃)HCH₂—, —C(CH₃)₂CH₂—, —C(CH₃)HC(CH₃)H— or —C(CH₃)₂C(CH₃)₂—;

In some embodiments, alternatively, R₅ and R₆ is independently selected from H or optionally substituted C₁-C₆ alkyl; alternatively, R₅ and R₆ is independently selected from H or methyl; alternatively, or R₅ and R₆ together with the nitrogen atom to which they are attached may form optionally substituted 5 to 6-membered heterocyclyl; alternatively, or R₅ and R₆ together with the nitrogen atom to which they are attached may form an optionally substituted piperidine ring, piperazine ring or morpholine ring.

In some embodiments, alternatively, —W—NR5R6 is selected from:

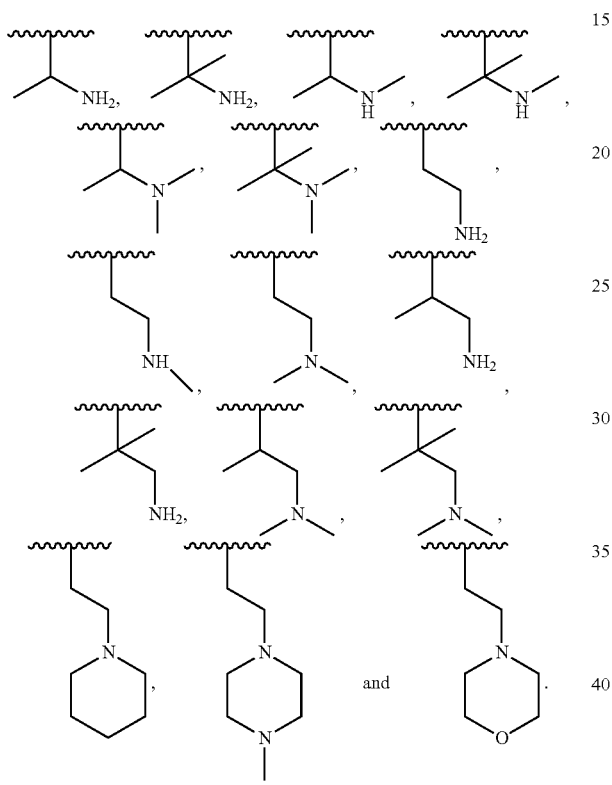

In some embodiments, alternatively, R₇ is optionally substituted C₁-C₆ alkoxy; alternatively, R₇ is —OCH₃.

In some embodiments, alternatively, R₈ is selected from H or C₁-C₆ alkyl; alternatively, R₈ is selected from H or methyl.

In the most preferred embodiment, the compound of the above formulae (I), and (IIa) to (IIm) are as follow:

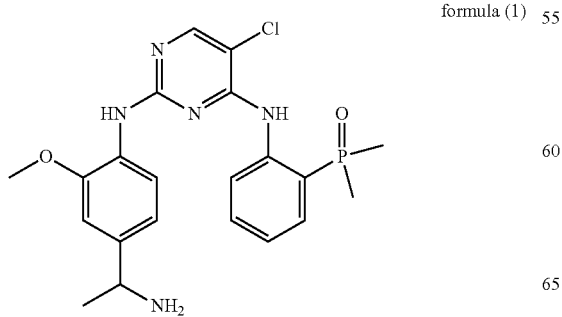

formula (1)

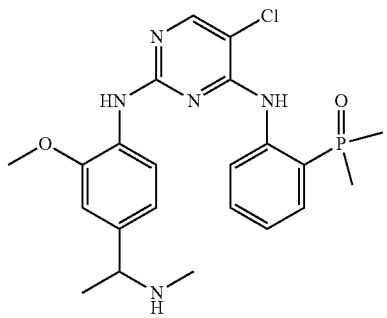

formula (2)

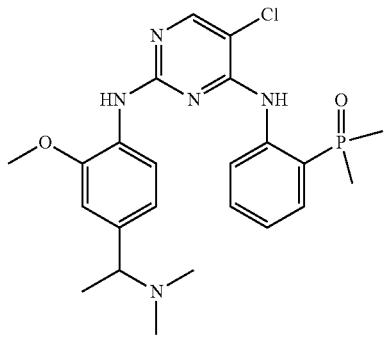

formula (3)

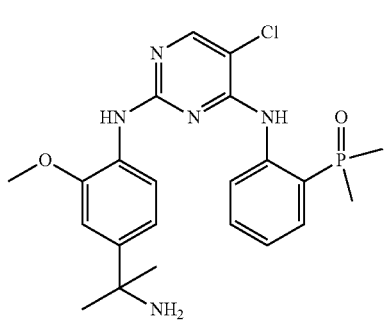

formula (4)

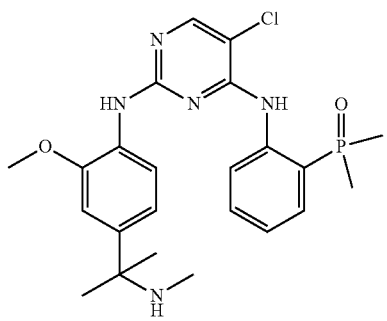

formula (5)

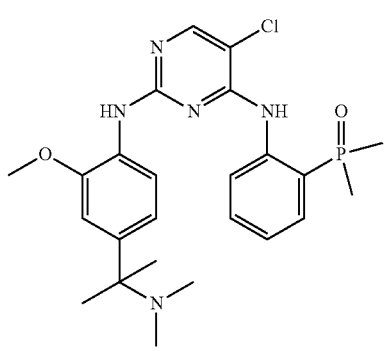

formula (6)

formula (7)
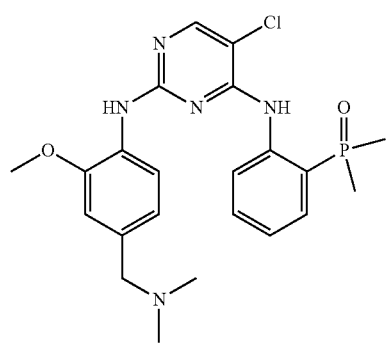
formula (8)
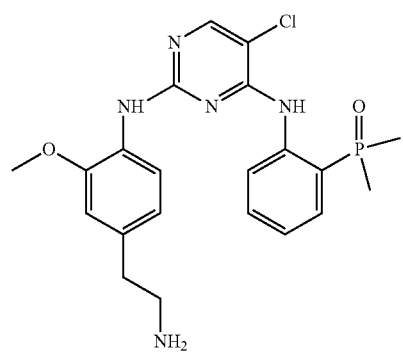
formuula (9)
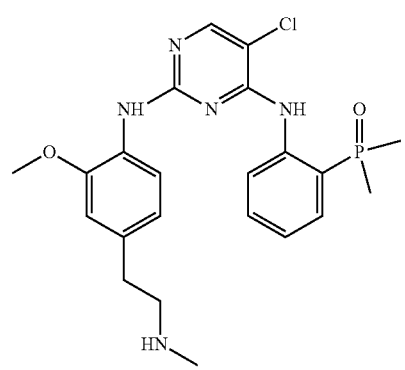
formula (10)
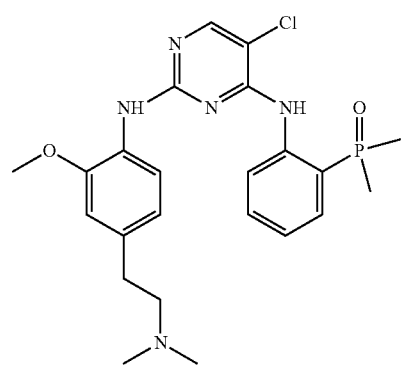
formula (11)
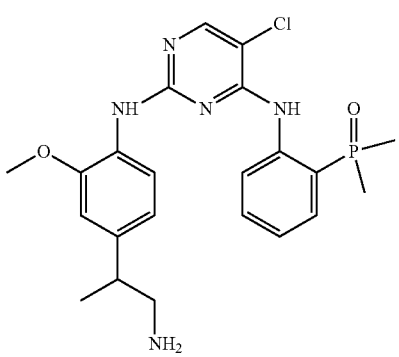
formula (12)
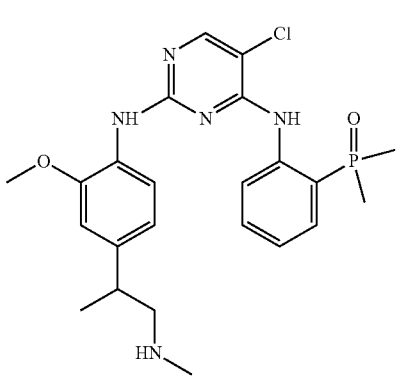
formula (13)
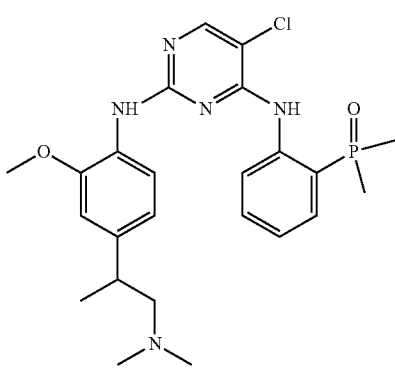
formula (14)
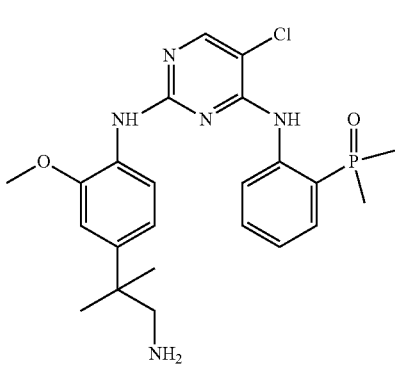

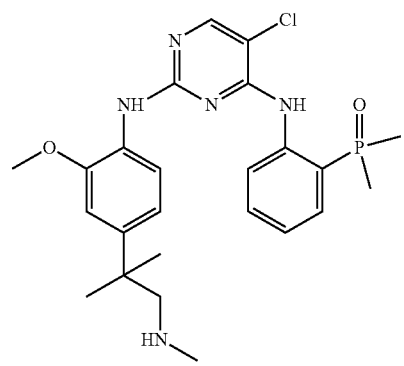
formula (15)
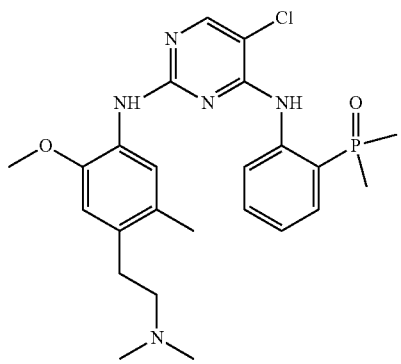
formula (19)
formula (16)
formula (17)
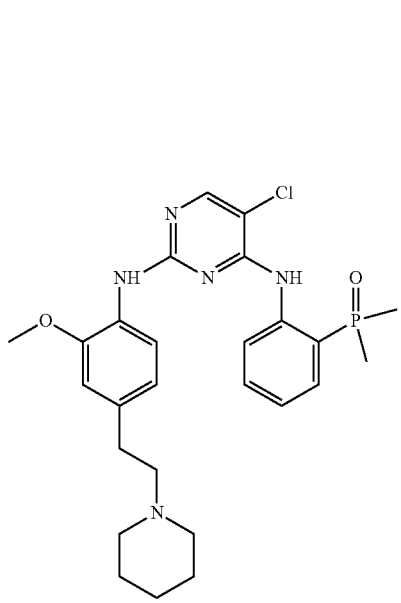
formula (20)
formula (18)
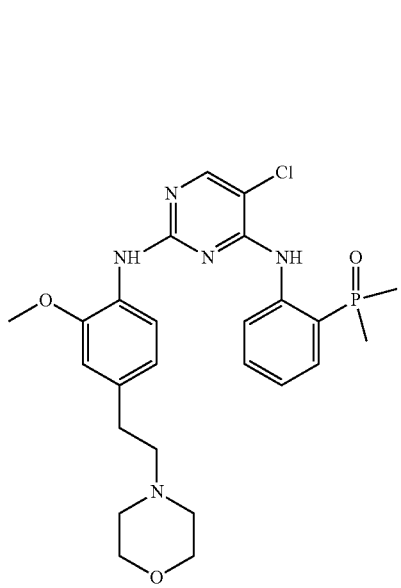
formula (21)

formula (22)

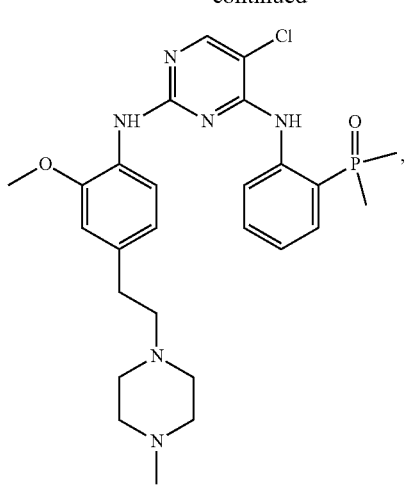

Compounds described herein can comprise one or more asymmetric centers, and thus can exist in various stereoisomeric forms, e.g., enantiomers and/or diastereomers. For example, the compounds described herein may be in the form of an individual enantiomer, diastereomer or geometric isomer (such as cis- and trans-isomer), or may be in the form of a mixture of stereoisomers, including racemic mixtures and mixtures enriched in one or more stereoisomer. Isomers may be isolated from mixtures by methods known to those skilled in the art, including chiral high pressure liquid chromatography (HPLC) and the formation and crystallization of chiral salts; or preferred isomers may be prepared by asymmetric syntheses.

Also disclosed herein are all suitable isotopic derivatives of the compounds disclosed herein. An isotope derivative of a compound disclosed herein is defined as wherein at least one atom is replaced by an atom having the same atomic number but differing in atomic mass from the atomic mass typically found in nature. Examples of isotopes that may be listed as compounds disclosed herein include hydrogen, carbon, nitrogen, oxygen, fluorine, and chlorine isotopes, such as $^2H$, $^3H$, $^{13}C$, $^{14}C$, $^{15}N$, $^{17}O$, $^{18}O$, $^{18}F$, $^{31}P$, $^{32}P$, $^{35}S$ and $^{36}Cl$, respectively. Certain isotopic derivatives of the compounds disclosed herein, such as the radioisotopes of $^3H$ and $^{14}C$, are also among them and are useful in the tissue distribution experiments of drugs and substrates. Tritium, i.e., $^3H$, and carbon-14, i.e., $^{14}C$, are easier to prepare and detect and are the first choice for isotopes. In addition, substitution with isotopes such as deuterium, i.e., $^2H$, has advantages in some therapies due to its good metabolic stability, for example, increased half-life in vivo or reduced dosage, and thus priority may be given in some cases. Isotopic derivatives of the compounds disclosed herein may be prepared by conventional procedures, for example by descriptive methods or by the preparations described in the Examples below, using appropriate isotopic derivatives of the appropriate reagents.

The compound of the present disclosure or a pharmaceutically acceptable salt thereof may be in an amorphous or crystalline form. Furthermore, the compounds of the present disclosure may exist in one or more crystalline forms. Accordingly, the disclosure includes within its scope all amorphous or crystalline forms of the compounds disclosed herein. The term "polymorph" refers to a crystalline form (or a salt, hydrate or solvate thereof) of a compound in a particular crystal packing arrangement. All polymorphs have the same elemental composition. Different crystalline forms typically have different X-ray diffraction patterns, infrared spectra, melting points, density, hardness, crystal shape, photoelectric properties, stability, and solubility. Recrystallization solvents, crystallization rates, storage temperatures, and other factors can result in a crystalline form that predominates. Various polymorphs of the compounds may be prepared by crystallization under different conditions.

Those skilled in the art will appreciate that many organic compounds can form complexes with solvents that react in or precipitate or crystallize from the solvent. These complexes are referred to as "solvates." When the solvent is water, the complex is referred to as a "hydrate." The disclosure encompasses all solvates of the compounds disclosed herein.

In addition, prodrugs are also included within the context of the present disclosure. The term "prodrug" as used herein refers to a compound which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each is incorporated herein by reference.

A prodrug is any covalently bonded carrier which, when administered to a patient, releases the compound of formula (I) in vivo. Prodrugs are typically prepared by modifying functional groups in such a way that the modifications may be cleaved by routine manipulation or in vivo to yield the parent compound. Prodrugs include, for example, compounds disclosed herein wherein a hydroxyl, amine or sulfhydryl group is bonded to any group which, when administered to a patient, may be cleaved to form a hydroxyl, amine or sulfhydryl group. Thus, representative examples of prodrugs include, but are not limited to, acetate, formate and benzoate derivatives of alcohol, mercapto and amine functional groups of the compounds of formula (I). Further, in the case of a carboxylic acid (—COOH), an ester such as a methyl ester, an ethyl ester or the like may be used. The ester itself may be active and/or may hydrolyze under conditions in human bodies. Suitable pharmaceutically acceptable hydrolysable in vivo ester groups include those groups which readily decompose in the human body to release the parent acid or a salt thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (eg, vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The following formulation examples illustrate representative pharmaceutical compositions that may be prepared in accordance with this disclosure. The present disclosure, however, is not limited to the following pharmaceutical compositions.

Exemplary Formulation 1—Tablets: A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets: A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets: A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets: A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets: A compound of the present disclosure may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 6—Tablets: A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets: A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules: A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid: A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection: A compound of the present disclosure may be dissolved or suspended in a buffered sterile saline injectable aqueous medium to a concentration of approximately 5 mg/mL.

Administration

The pharmaceutical composition provided by the present disclosure may be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and yet alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration may be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present disclosure can also be administered in sustained release forms or from sustained release drug delivery systems. A description of representative sustained release materials may be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment Method

The present disclosure provides the administration of a compound of the present disclosure, or a pharmaceutically acceptable salt, stereoisomer, solvate, hydrate, crystalline form, prodrug or isotopic derivative thereof, or the pharmaceutical composition according to the disclosure, to a subject in need of treatment, for use in the treatment of cancer. In some embodiments, the cancer is ALK-driven cancer. In some embodiments, the cancer is non-small cell lung cancer.

A "therapeutically effective amount" is that amount effective for detectable killing or inhibition of the growth or spread of cancer cells; the size or number of tumors; or other measure of the level, stage, progression or severity of the cancer. The exact amount required can vary from subject to subject, depending on the species, age, and general condition of the subject, the severity of the disease, the particular anticancer agent, its mode of administration, combination treatment with other therapies, and the like.

Disclosed herein are compounds having biological properties which make them of interest for treating or modulating disease in which kinases can be involved, symptoms of such disease, or the effect of other physiological events mediated by kinases. For instance, a number of compounds as disclosed herein have been shown to inhibit tyrosine kinase activity of ALK, fak and c-met, among other tyrosine kinases which are believed to mediate the growth, development and/or metastasis of cancer. A number of compounds as disclosed herein have also been found to possess potent in vitro activity against cancer cell lines. Such compounds are thus of interest for the treatment of cancers, including solid tumors as well as lymphomas and including cancers which are resistant to other therapies.

In some embodiments, the cancer is an ALK driven cancer. In some embodiments, the cancer is non-small cell lung cancer (NSCLC). In some embodiments, the cancer is ALK-positive NSCLC. In some embodiments, the cancer is locally advanced or metastatic ALK-positive NSCLC. In some embodiments, the cancer/patient has previously been treated with crizotinib or another tyrosine kinase inhibitor. In some embodiments, the cancer/patient has not previously been treated with an ALK inhibitor.

Such cancers include, but are not limited to, cancers of the breast, non small cell lung cancer (NSCLC), neural tumors such as glioblastomas and neuroblastomas; esophaegeal carcinomas, soft tissue cancers such as rhabdomyosarcomas, among others; various forms of lymphoma such as a non-Hodgkin's lymphoma (NHL) known as anaplastic large-cell lymphoma (ALCL), various forms of leukemia; and including cancers which are ALK or c-met mediated.

Anaplastic Lymphoma Kinase (ALK) is a cell membrane-spannning receptor tyrosine kinase, which belong to the insulin receptor subfamily. ALK receptor tyrosine kinase (RTK) was initially identified due to its involvement in the human non-Hodgkin lymphoma subtype known as anaplastic large-cell lymphoma (ALCL). ALK normally has a restricted distribution in mammalian cells, being found at significant levels only in nervous system during embryonic development, suggesting a possible role for ALK in brain development.

In addition to its role in normal development, the expression of full-length normal ALK has been detected in cell lines derived from various tumors, such as glioblastoma, neuroectodermal tumors and glioblastoma and breast cancer and melanoma lines.

In common with other RTKs, translocations affect the ALK gene, resulting in expression of oncogenic fusion kinases, the most common of which is NPM-ALK. For example, approximately sixty percent of anaplastic large cell lymphomas (ALCL) are associated with a chromosome mutation that generates a fusion protein consisting of nucleophosmin (NMP) and the intracellular domain of ALK. This mutant protein, NPM-ALK, possesses a constitutively active tyrosine kinase domain that is responsible for its oncogenic property through activation of downstream effectors. Experimental data have demonstrated that the aberrant expression of constitutively active ALK is directly implicated in the pathogenesis of ALCL and that inhibition of ALK can markedly impair the growth of ALK positive lymphoma cells. The constitutively activated chimeric ALK has also been demonstrated in about 60% of inflammatory myofibroblastic tumors (IMTs), a slow growing sarcoma that mainly affects children and young adults. Furthermore, recent reports have also described the occurrence of a variant ALK fusion, TPM4-ALK, in cases of squamous cell carcinoma (SCC) of the esophagus. Thus, ALK is one of the few examples of an RTK implicated in oncogenesis in both non-hematopoietic and hematopoietic malignancies. More recently, it has been shown that a small inversion within chromosome 2p results in the formation of a fusion gene comprising portions of the echinoderm microtubule-associated protein-like 4 (EML4) gene and the anaplastic lymphoma kinase (ALK) gene in non-small-cell lung cancer (NSCLC) cells.

In some embodiments, an ALK inhibitor can create durable cures when used as a single therapeutic agent or combined with current chemotherapy for ALCL, IMT, proliferative disorders, glioblastoma and other possible solid tumors cited herein, or, as a single therapeutic agent, could be used in a maintenance role to prevent recurrence in patients in need of such a treatment.

Compounds as disclosed herein can be administered as part of a treatment regimen in which the compound is the sole active pharmaceutical agent, or used in combination with one or more other therapeutic agents as part of a combination therapy. When administered as one component of a combination therapy, the therapeutic agents being administered can he formulated as separate compositions that are administered at the same time or sequentially at different times (e.g., within 72 hours, 48 hours, or 24 hours of one another), or the therapeutic, agents can be formulated together in a single pharmaceutical composition and administered simultaneously.

Thus, the administration of compounds as disclosed herein in a form disclosed herein can be in conjunction with at least one additional therapeutic agent known to those skilled in the art in the prevention or treatment of cancer, such as radiation therapy or cytostatic agents, cytotoxic agents, other anti-cancer agents and other drugs to ameliorate symptoms of the cancer or side effects of any of the drugs. Non-limiting examples of additional therapeutic agents include agents suitable for immunotherapy (such as, for example, PD-1 and PDL-1 inhibitors), antiangiogenesis (such as, for example, bevacizumab), and/or chemotherapy.

If formulated as a fixed dose, such combination products employ compounds as disclosed herein within the accepted dosage ranges. Compounds as disclosed herein can also be administered sequentially with other anticancer or cytotoxic agents when a combination formulation is appropriate. Compounds as disclosed herein can be administered prior to, simultaneously with, or after administration of the other anticancer or cytotoxic agent, Currently, standard treatment of primary tumors consists of surgical excision, when appropriate, followed by either radiation or chemotherapy, and typically administered intravenously. The typical chemotherapy regime consists of either DNA alkylating agents, DNA intercalating agents. CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, anti-hormonal agents, immunological agents, interferon-type agents and a category of miscellaneous agents.

Examples of other therapeutic agents include but not limited to one or more of the following: an anti-cancer alkylating or intercalating agent (e.g., mechlorethamine, chlorambucil, Cyclophosphamide, Melphalan, and Ifosfamide); antimetabolite (e.g., Methotrexate); purine antagonist or pyrimidine antagonist (e.g., 5-Fluorouracil, Cytarabile, and Gemcitabine); spindle poison (e.g., Vinblastine, Vincristine, Vinorelbine and Paclitaxel); podophyllotoxin (e.g., Etoposide, Irinotecan, Topotecan); antibiotic (e.g., Doxorubicin, Bleomycin and Mitomycin); nitrosourea (e.g., Carmustine, Lomustine); inorganic ion (e.g., Cisplatin, Carboplatin, Oxaliplatin or oxiplatin); enzyme (e.g., Asparaginase); hormone (e.g., Tamoxifen, Leuprolide, Flutamide or Megestrol); mTOR inhibitor (e.g., Sirolimus (rapamycin), Temsirolimus (CCI779), Everolimus (RAD001), AP23573 or other compounds disclosed in U.S. Pat. No. 7,091,213); proteasome inhibitor (such as Velcade, other proteasome inhibitors (e.g., an inhibitor of Src, Bcr/Abl, kdr, flt3, aurora-2, glycogen synthase kinase 3 (GSK-3), EGFR kinase (e.g., Iressa, Tarceva, etc.), VEGF-R kinase, PDGF-R kinase, etc); an antibody, soluble receptor or other receptor antagonist against a receptor or hormone implicated in a cancer (including receptors such as EGFR, ErbB2, VEGFR, PDGFR, and IGF-R; and agents such as Herceptin, Avastin, Erbitux, etc.); etc. Examples of other therapeutic agents include among others, Zyloprim, alemtuzmab, altretamine, amifostine, nastrozole, antibodies against prostate-specific membrane antigen (such as MLN-591, MLN591RL and MLN2704), arsenic trioxide, bexarotene, bleomycin, busulfan, capecitabine, Gliadel Wafer, celecoxib, chlorambucil, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, exemestane, fludarabine, 5-FU, fulvestrant, gemcitabine, gemtuzumab-ozogamicin, goserelin acetate, hydroxyurea, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, Rituximab, talc, tamoxifen, temozolamide, teniposide, VM-26, topotecan, toremifene, 2C4 (or other antibody which interferes with HER2-mediated signaling), tretinoin, ATRA, valrubicin, vinorelbine, or pamidronate, zoledronate or other bisphosphonate.

EXAMPLES

The present disclosure will be further described below in combination with specific embodiments. It should be understood that these examples are only used to illustrate the present disclosure and not to limit the scope of the present disclosure. The experimental methods without specific conditions in the following examples generally follow the conventional conditions or the conditions recommended by the manufacturer. Unless otherwise stated, parts and percentages are parts by weight and weight percent.

Generally, in the preparation process, each reaction is usually carried out in an inert solvent at a temperature from room temperature to reflux temperature (such as 0° C. to 100° C., alternatively 0° C. to 80° C.). The reaction time is usually 0.1-60 hours, alternatively 0.5-24 hours.

Example 1 Preparation of (2-((5-chloro-2-((4-((dimethylamino)methyl)-2-methoxyphenyl)amino)pyrimidin-4-yl)amino)phenyl)dimethylphosphine oxide (Compound T-1)

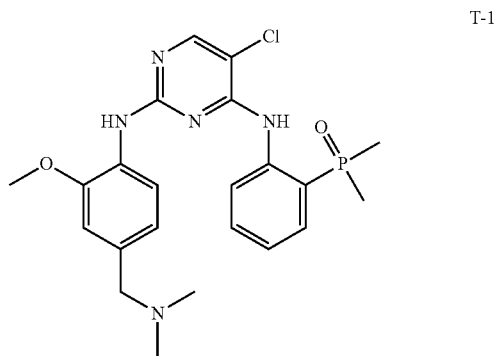

The following route was used for the synthesis

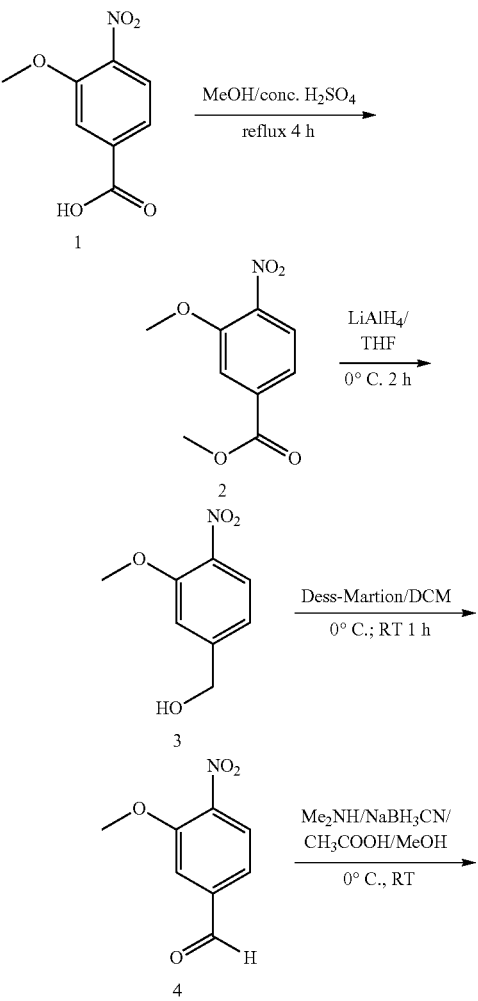

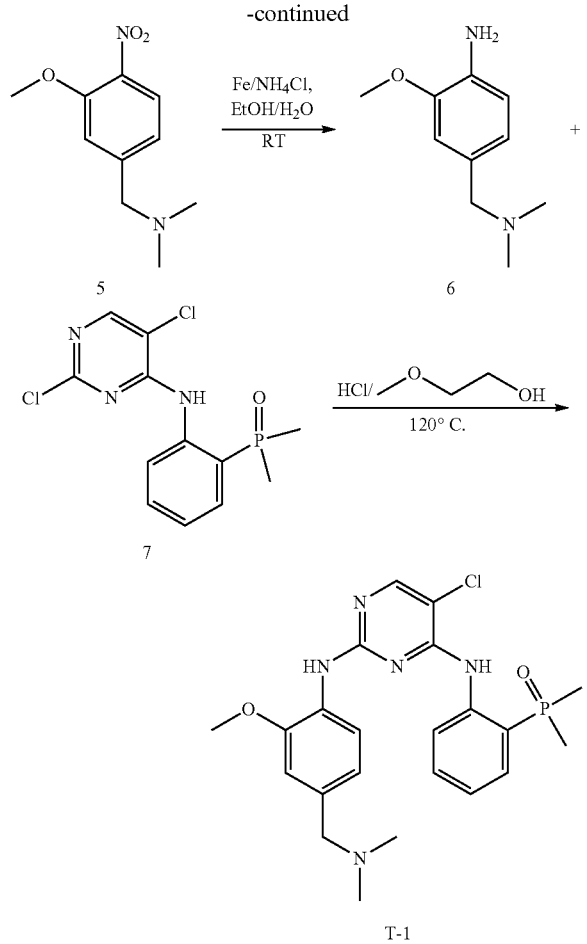

Step 1 Synthesis of Compound 2

Compound 1 (0.6 g, 3.0 mmol) and methanol (15 mL) were added in sequence into a 50 mL single-necked flask equipped with a magnetic stirrer, and the mixture was stirred to form a solution. Concentrated sulfuric acid (1 mL) was slowly added dropwise. After the addition was completed, the temperature was raised to reflux temperature and the reaction was stirred at this temperature under a nitrogen atmosphere for 3 hours. After cooled to room temperature, the reaction was quench by adding water (40 mL), and the resulting solution was extracted with dichloromethane (40 mL×2). Organic phases were combined and washed with saturated brine, dried over anhydrous sodium sulfate, filtered, and concentrated to give 0.52 g of colorless liquid. Yield: 82.1%. LC-MS(APCI): m/z=212.1 (M+1)$^+$.

Step 2 Synthesis of Compound 3

To a 50 mL single-necked flask equipped with a magnetic stirrer compound 2 (0.5 g, 2.37 mmol) and anhydrous THF (15 mL) were added in sequence, and the mixture was stirred to form a solution. After cooled in an ice water bath, lithium aluminum hydride (LiAlH$_4$, 90 mg, 2.37 mmol) was slowly added, and the reaction was stirred at this temperature under a nitrogen atmosphere for 1 hour. Sodium sulfate decahydrate (10 g) was added to quench the reaction, which was diluted with dichloromethane (40 mL) and filtered after stirring for 5 minutes. The filter cake was washed with dichloromethane (10 mL), the resulting solution was dried over anhydrous sodium sulfate, filtered, and concentrated to obtain 0.4 g of a white solid. Yield: 92.2%. LC-MS(APCI): m/z=184.1 (M+1)$^+$.

Step 3 Synthesis of Compound 4

To a 100 mL single-necked flask equipped with a magnetic stirrer compound 3 (400 mg, 2.18 mmol) and dichloromethane (DCM, 10 mL) were added in sequence, and the mixture was stirred to form a solution. Dess-Martin periodinane (904 mg, 2.18 mmol) was added and the reaction mixture was stirred at room temperature for 1 hour under a nitrogen atmosphere. The reaction was quenched by adding water (20 mL), the resulting solid was filtered, and the aqueous phase was extracted with dichloromethane (20 mL×2). The organic phases were combined, washed with water (30 mL×2), dried over anhydrous sodium sulfate, concentrated and passed through a silica gel column to obtain 300 mg of a white solid. Yield: 74.9%. LC-MS (APCI): m/z=182.1 (M+1)$^+$.

Step 4 Synthesis of Compound 5

To a 50 mL single-necked flask equipped with a magnetic stirrer compound 4 (181 mg, 1.0 mmol) and methanol (5 ml) were added in sequence, and the mixture was stirred to form a solution. A solution of dimethylamine in tetrahydrofuran (1 mL, 2.0 mmol, 2M) and glacial acetic acid (1 drop) were added dropwise, and the reaction was stirred at room temperature for 10 minutes under a nitrogen atmosphere, and NaBH$_3$CN (150 mg, 2.5 mmol) was slowly added in dropwise, and the reaction was stirred at room temperature for 1 hour. The reaction was quenched by adding water (5 mL), and extracted with ethyl acetate (15 mL×3). The organic phases were combined, dried over anhydrous sodium sulfate, filtered, and concentrated. The residue was passed through a silica gel column to obtain 126 mg of a white solid. Yield: 60.0%. LC-MS(APCI): m/z=211.1 (M+1)$^+$.

Step 5 Synthesis of Compound 6

To a 50 mL single-necked flask equipped with a magnetic stirrer and a condenser tube, was added compound 5 (126 mg, 0.6 mmol) and ethanol/water (8 mL, 3/1), and the mixture was stirred to form a solution. Reduced iron powder (3.6 mmol, 202 mg) and ammonium chloride (0.6 mmol, 32 mg) was added, the reaction was heated to reflux under a nitrogen atmosphere and reacted for 1 hour. Then the reaction was cooled to room temperature, filtered and the filter cake was washed with ethanol (5 mL). The organic solvent was removed by concentration, and the resulting solution was extracted with dichloromethane (10 mL×2). The organic phases were combined, dried over anhydrous sodium sulfate, filtered, and concentrated to give 80 mg of a brown solid. Yield: 74.1%. LC-MS(APCI): m/z=181.1 (M+1)$^+$.

Step 6 Synthesis of compound T-1

To a 25 mL single-necked flask equipped with a magnetic stirrer and a condenser tube, compound 6 (80 mg, 0.44 mmol), compound 7 (138 mg, 0.44 mmol) and ethylene glycol monomethyl ether (3 mL) were added, and the mixture was stirred to form a solution.

A solution of hydrogen chloride in isopropanol (0.66 mmol, 0.13 mL, 5M) was added dropwise, and the temperature was raised to 120° C. under a nitrogen atmosphere and the reaction was stirred at this temperature overnight. The reaction was cooled to room temperature, water (10 mL) and saturated sodium bicarbonate (5 mL) was added, the solution was extracted with dichloromethane (15 mL×3). The organic phases were combined, washed with saturated brine, dried over anhydrous sodium sulfate, filtered and concentrated. The residue was passed through a silica gel column to give 100 mg of a white solid. Yield: 49.5%. LC-MS (APCI): m/z=460.2 (M+1)$^+$. $^1$H NMR (400 MHz, DMSO-D$_6$) δ ppm: 11.17 (s, 1H), 8.47-8.43 (m, 1H), 8.14 (s, 1H), 8.12 (s, 1H), 7.71 (d, J=8.0 Hz, 1H), 7.58-7.53 (m, 1H), 7.39

(t, J=8.0 Hz, 1H), 7.13 (t, J=8.0 Hz, 1H), 6.97 (s, 1H), 6.81 (d, J=8.0 Hz, 1H), 3.80 (s, 3H), 2.17 (s, 6H), 1.78 (s, 3H), 1.75 (s, 3H).
Example 2 Preparation of (2-((2-((4-(2-aminoethyl)-2-methoxyphenyl)amino)-5-chloropyrimidin-4-yl)amino)phenyl)dimethylphosphine oxide (Compound T-2)
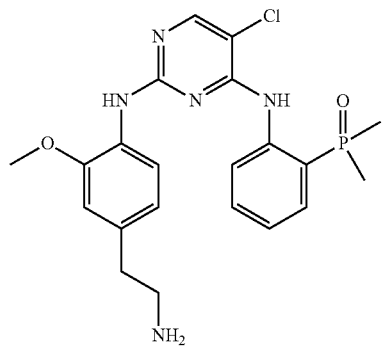
T-2
The following route was used for the synthesis:
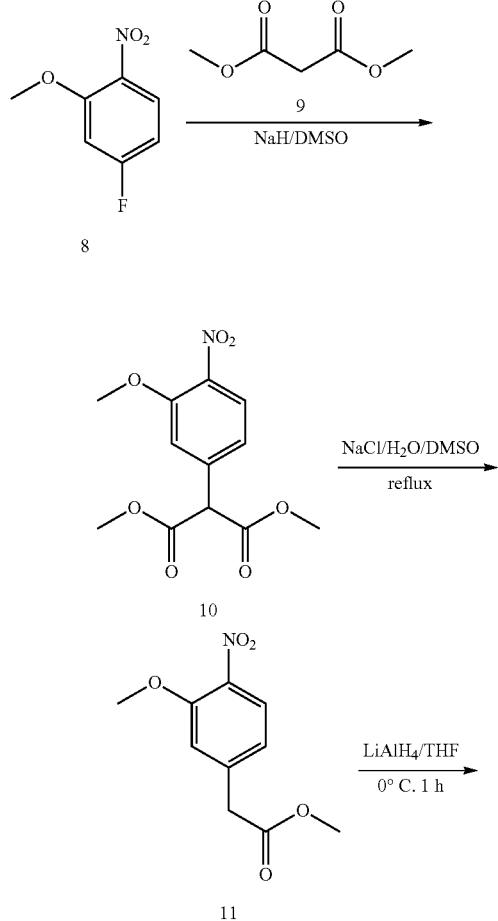
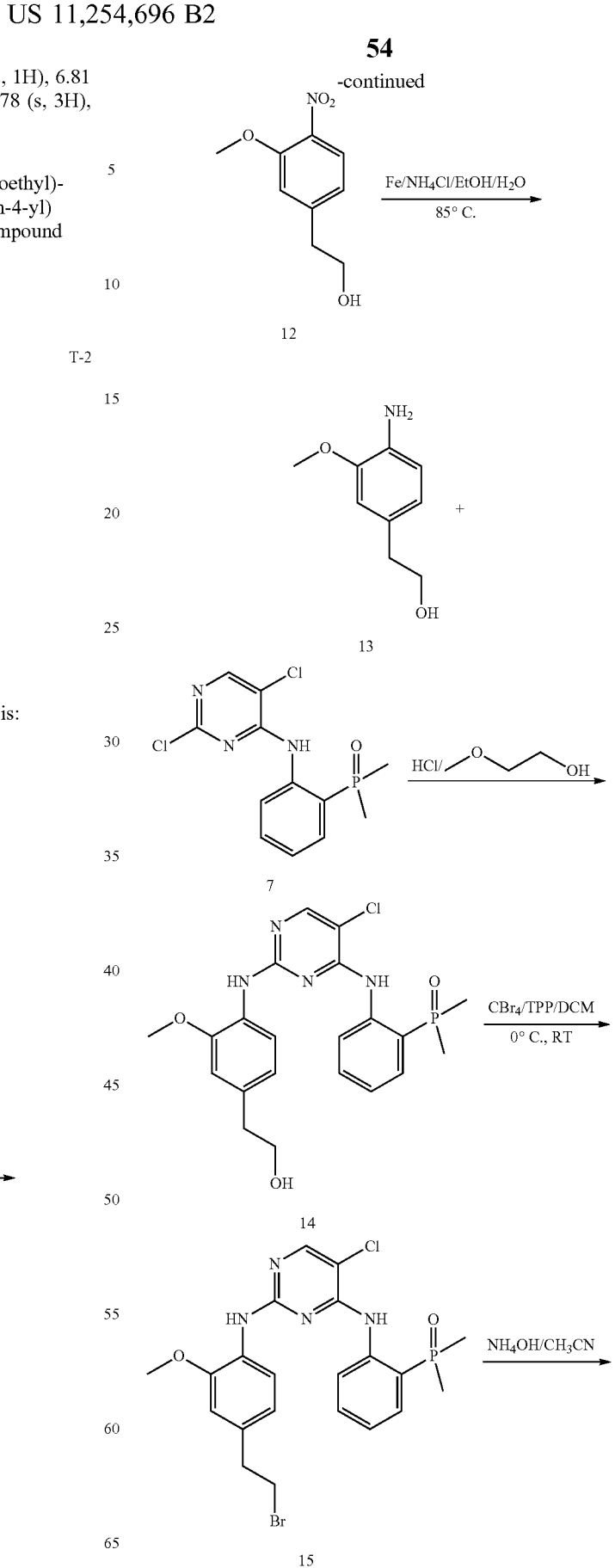

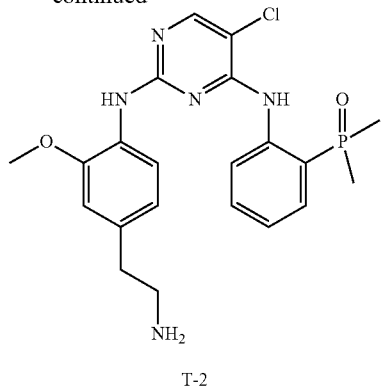

T-2

Step 1 Synthesis of Compound 10

To a 250 mL single-necked flask equipped with a magnetic stirrer compound 8 (5.1 g, 30 mmol) and anhydrous DMSO (40 mL) were added in sequence, the mixture was stirred to form a solution under a nitrogen atmosphere, and after cooled to 0° C., NaH (3.6 g, 90 mmol, 60%) was slowly added, and the solution was stirred at 0° C. for half an hour. A solution of compound 9 (11.6 g, 90 mmol) in DMSO (10 mL) was added dropwise, the ice bath was removed, and the reaction mixture was warmed to 100° C. and the reaction was stirred at this temperature for 3 hours. The reaction was cooled to room temperature before the addition of water (50 mL), and the solution was extracted with ethyl acetate (50 mL×3). The organic phases were combined, washed with water (60 mL×2), dried over anhydrous sodium sulfate, filtered, concentrated, and passed through a silica gel column to give 8.3 g of a white solid.

Yield: 98.1%. LC-MS(APCI): m/z=282.1 (M−1)$^-$.

Step 2 Synthesis of Compound 11

To a 250 mL single-necked flask equipped with a magnetic stirrer was added compound 10 (2.83 g, 10 mmol) and DMSO (50 mL) in sequence, and the mixture was stirred to form a solution. NaCl (1.17 g, 20 mmol) and water (0.18 g, 10 mmol) were added. The reaction mixture was heated to 120° C. and stirred at this temperature for 3 hours. The reaction was cooled to room temperature, added with water (80 mL), extracted with ethyl acetate (50 mL×3). The organic phases were combined, washed with water (60 mL×2), dried over anhydrous sodium sulfate, filtered, concentrated and passed through a silica gel column to obtain 1.9 g of a white solid. Yield: 84.1%. LC-MS(APCI): m/z=224.1 (M−1)$^-$.

Step 3 Synthesis of compound 12

To a 250 mL single-necked flask equipped with a magnetic stirrer compound 11 (1.9 g, 8.4 mmol) and anhydrous THF (50 mL) were added in sequence, and the mixture was stirred to form a solution. The solution was cooled in an ice water bath, and LiAlH$_4$ (320 mg, 8.4 mmol) was slowly added. The reaction was stirred at this temperature under a nitrogen atmosphere for 1 hour. The reaction was quenched by adding sodium sulfate decahydrate (20 g), and stirred for 5 minutes. The solution was diluted with dichloromethane (60 mL), filtered, and the filter cake was washed with dichloromethane (10 mL). The resulting solution was dried over anhydrous sodium sulfate, filtered, and concentrated to obtain 1.3 g of a white solid. Yield: 79.0%. LC-MS(APCI): m/z=198.1 (M+1)$^+$.

Step 4 Synthesis of compound 13

To a 100 mL single-necked flask equipped with a magnetic stirrer and a condenser tube was added compound 12 (1.3 g, 6.6 mmol) and ethanol/water (40 mL, 3/1), and the mixture was stirred to form a solution. Reduced iron powder (39.6 mmol, 2.23 g) and ammonium chloride (6.6 mmol, 350 mg) were added, the reaction was heated to reflux under a nitrogen atmosphere and reacted at this temperature for 1 hour. The reaction was cooled to room temperature, filtered, the filter cake was washed with ethanol (10 mL). The organic solvent was removed by concentration, and the resulting solution was extracted with dichloromethane (30 mL×3). The organic phases were combined, dried over anhydrous sodium sulfate, filtered, and concentrated to give 850 mg of a brown solid. Yield: 77.1%. LC-MS(APCI): m/z=168.1 (M+1)$^+$.

Step 6 Synthesis of compound 14

To a 50 mL single-necked flask equipped with a magnetic stirrer and a condenser tube compound 13 (850 mg, 5.09 mmol), compound 7 (1.6 g, 5.09 mmol) and ethylene glycol monomethyl ether (10 mL) were added, and the mixture was stirred to form a solution. A solution of hydrogen chloride in isopropanol (7.64 mmol, 1.53 mL, 5M) was added dropwise, and the temperature was raised to 120° C. under a nitrogen atmosphere, and the reaction was stirred at this temperature overnight. The reaction was cooled to room temperature, water (30 mL) and saturated sodium bicarbonate (20 mL) were added, and the solution was extracted with dichloromethane (50 mL×3). The organic phases were combined, washed with saturated brine, dried over anhydrous sodium sulfate, filtered, concentrated, the residue was passed through a silica gel column to give 1.2 g of a white solid. Yield: of 52.9%. LC-MS(APCI): m/z=447.2 (M+1)$^+$. $^1$H NMR (400 MHz, DMSO-D$_6$) 5/ppm: 11.16 (s, 1H), 8.46-8.43 (m, 1H), 8.1 l(s, 1H), 8.07 (s, 1H), 7.62 (d, J=8.0 Hz, 1H), 7.58-7.51 (m, 1H), 7.39 (t, J=8.0 Hz, 1H), 7.12 (t, J=8.0 Hz, 1H), 6.90 (s, 1H), 6.73 (d, J=8.0 Hz, 1H), 4.62 (t, J=4.8 Hz, 1H), 3.77 (s, 3H), 3.61 (q, J=4.8 Hz, 2H), 2.71 (t, J=5.6 Hz, 2H), 1.77 (s, 3H), 1.74 (s, 3H).

Step 7 Synthesis of compound 15

To a 100 mL single-necked flask equipped with a magnetic stirrer and a condenser tube compound 14 (1.7 g, 3.8 mmol) and anhydrous dichloromethane (20 mL) were added, and the mixture was stirred to form a solution. CBr$_4$ (4.1 mmol, 1.36 g) was added, the solution was cooled to 0° C. under a nitrogen atmosphere, and triphenylphosphine (TPP, 1.08 g, 4.1 mmol) was added. The ice bath was removed after addition, and the reaction was stirred at room temperature for 1 h. The solvent was distilled off under reduced pressure, and the residue was passed through a silica gel column to obtain 960 mg of a white solid. Yield: 49.5%. LC-MS(APCI): m/z=509.1, 511.1 (M+1)$^+$.

Step 8 Synthesis of Compound T-2

To a 50 mL single-necked flask equipped with a magnetic stirrer Compound 15 (102 mg, 0.2 mmol) and acetonitrile (2 mL) were added, and the mixture was stirred to form a solution. Ammonia (3 mL) was added, and the reaction was stirred at room temperature under a nitrogen atmosphere overnight. The solvent was distilled off under reduced pressure, and the residue was passed through a silica gel column to obtain 60 mg of a white solid. Yield: 67.4%. LC-MS(APCI): m/z=446.1 (M+1)$^+$. $^1$H NMR (400 MHz, DMSO-D$_6$) δ ppm: 11.19 (s, 1H), 8.49-8.46 (m, 1H), 8.15 (s, 1H), 8.10 (s, 1H), 7.96 (br s, 2H), 7.77 (d, J=8.0 Hz, 1H), 7.61-7.55 (m, 1H), 7.45 (t, J=8.0 Hz, 1H), 7.16 (t, J=8.0 Hz, 1H), 6.97 (s, 1H), 6.78 (d, J=8.0 Hz, 1H), 3.84 (s, 3H), 3.06 (t, J=8.0 Hz, 2H), 2.88 (t, J=8.0 Hz, 2H), 1.80 (s, 3H), 1.76 (s, 3H).

Example 3 Preparation of (2-((5-chloro-2-((4-(2-(dimethylamino)ethyl)-2-methoxyphenyl)amino)pyrimidin-4-yl)amino)phenyl)dimethylphosphine oxide (Compound T-3)

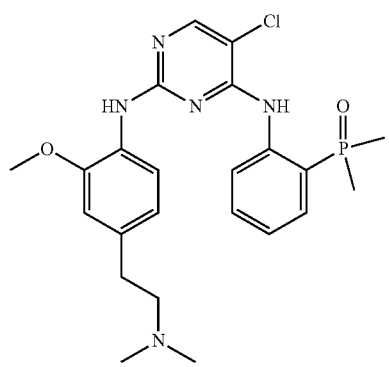

The following route was used for the synthesis:

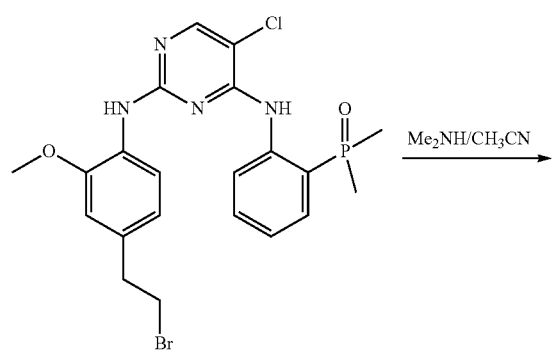

To a 50 mL single-necked flask equipped with a magnetic stirrer compound 15 (102 mg, 0.2 mmol) and acetonitrile (2 mL) were added, and the mixture was stirred to form a solution. A solution of dimethylamine in tetrahydrofuran (5 mL) was added, and the reaction was stirred at room temperature under a nitrogen atmosphere overnight. The solvent was distilled off under reduced pressure, and the residue was passed through a silica gel column to obtain 60 mg of a white solid. Yield: 63.4%. LC-MS(APCI): m/z=474.2 (M+1)+. 1H NMR (400 MHz, DMSO-D6) δ ppm: 11.19 (s, 1H), 8.48-8.45 (m, 1H), 8.14 (s, 1H), 8.12 (s, 1H), 7.71 (d, J=8.0 Hz, 1H), 7.60-7.56 (m, 1H), 7.44 (t, J=8.0 Hz, 1H), 7.15 (t, J=8.0 Hz, 1H), 6.99 (s, 1H), 6.79 (d, J=8.0 Hz, 1H), 3.82 (s, 3H), 3.04-3.00 (m, 2H), 2.95-2.89 (m, 2H), 2.60 (s, 6H), 1.80 (s, 3H), 1.76 (s, 3H).

Example 4 Preparation of (2-((5-chloro-2-((2-methoxy-4-(2-(piperidin-1-yl)ethyl)phenyl)amino)pyrimidin-4-yl)amino)phenyl)dimethylphosphine oxide (Compound T-4)

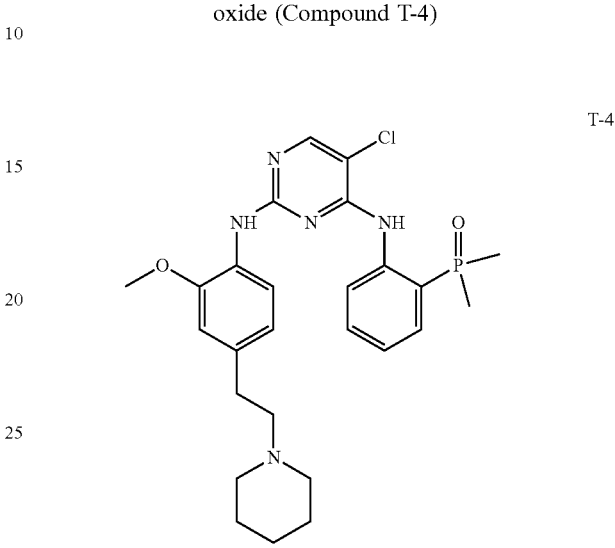

The following route was used for the synthesis:

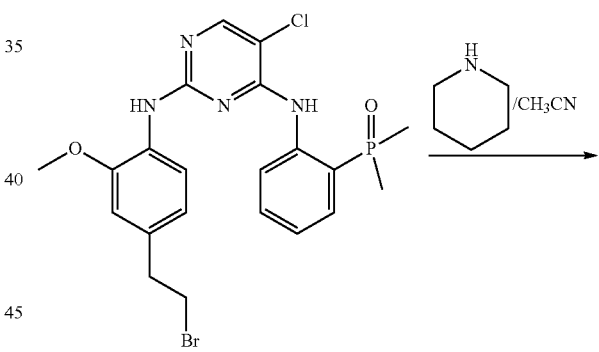

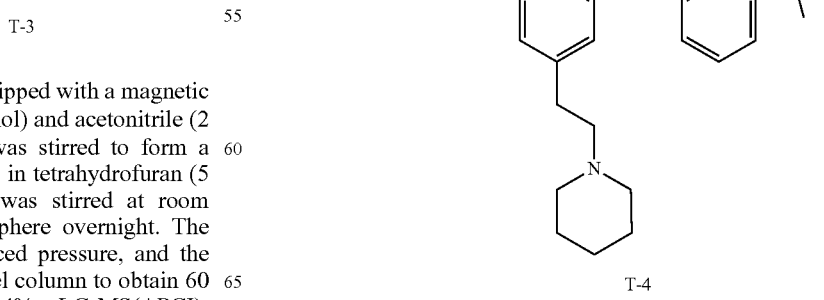

To a 50 mL single-necked flask equipped with a magnetic stirrer compound 15 (102 mg, 0.2 mmol) and acetonitrile (2 mL) were added, and the mixture was stirred to form a solution. Piperidine (51 mg, 0.6 mmol) was added, and the reaction was stirred at room temperature under a nitrogen atmosphere overnight. The solvent was distilled off under reduced pressure, and the residue was passed through a silica gel column to obtain 60 mg of a white solid. Yield: 58.5%. LC-MS(APCI): m/z=514.2 (M+1)$^+$. $^1$H NMR (400 MHz, DMSO-D$_6$) δ ppm: 11.19 (s, 1H), 8.48-8.45 (m, 1H), 8.14 (s, 1H), 8.12 (s, 1H), 7.69 (d, J=8.0 Hz, 1H), 7.60-7.56 (m, 1H), 7.43 (t, J=8.0 Hz, 1H), 7.15 (t, J=8.0 Hz, 1H), 6.97 (s, 1H), 6.78 (d, J=8.0 Hz, 1H), 3.81 (s, 3H), 3.38-3.36 (m, 2H), 2.91-2.62 (m, 6H), 1.80 (s, 3H), 1.76 (s, 3H), 1.69-1.62 (m, 4H), 1.49-1.45 (m, 2H).

Example 5 Preparation of (2-((5-chloro-2-((2-methoxy-4-(2-(4-methylpiperazin-1-yl)ethyl)phenyl)amino)pyrimidin-4-yl)amino)phenyl)dimethylphosphine oxide (Compound T-5)

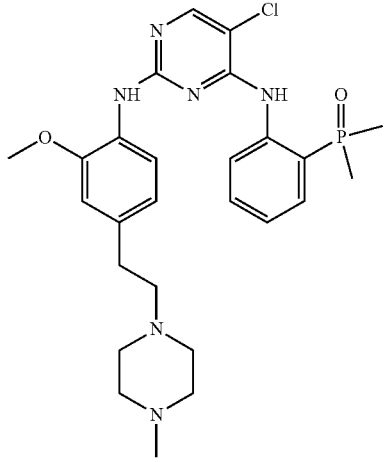

T-5

The following route was used for the synthesis:

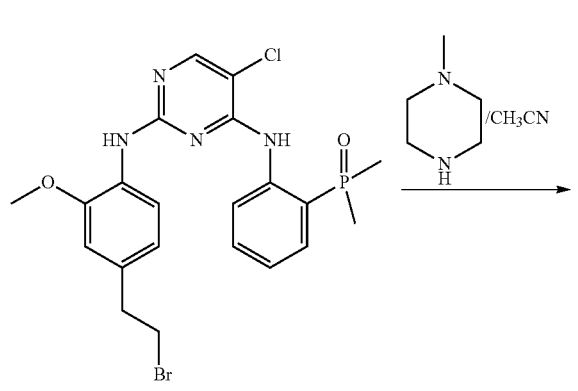

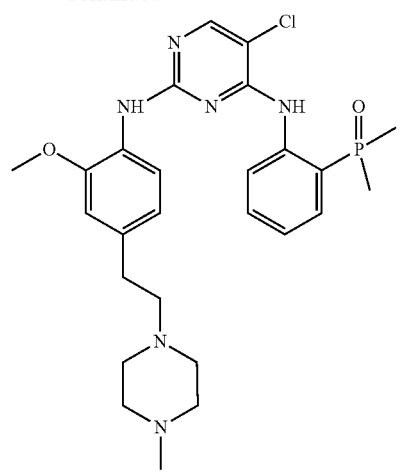

T-5

To a 50 mL single-necked flask equipped with a magnetic stirrer compound 15 (102 mg, 0.2 mmol) and acetonitrile (2 mL) were added, and the mixture was stirred to form a solution. N-methylpiperazine (60 mg, 0.6 mmol) was added, the reaction was stirred at room temperature under a nitrogen atmosphere overnight. The solvent was distilled off under reduced pressure, and the residue was passed through a silica gel column to obtain 60 mg of a white solid. Yield: 56.8%. LC-MS(APCI): m/z=514.2 (M+1)$^+$. $^1$H NMR (400 MHz, DMSO-D$_6$) δ ppm: 11.18 (s, 1H), 8.48-8.45 (m, 1H), 8.13 (s, 1H), 8.10 (s, 1H), 7.64 (d, J=8.0 Hz, 1H), 7.59-7.54 (m, 1H), 7.41 (t, J=8.0 Hz, 1H), 7.14 (t, J=8.0 Hz, 1H), 6.96 (s, 1H), 6.76 (d, J=8.0 Hz, 1H), 3.80 (s, 3H), 3.38-3.30 (m, 4H), 2.74 (t, J=8.0 Hz, 2H), 2.59-2.52 (m, 4H), 2.50-2.47 (m, 2H), 2.26 (s, 3H), 1.79 (s, 3H), 1.76 (s, 3H).

Example 6 Preparation of (2-((5-chloro-2-((2-methoxy-4-(2-morpholinoethyl)phenyl)amino)pyrimidin-4-yl)amino) phenyl)dimethylphosphine oxide (Compound T-6)

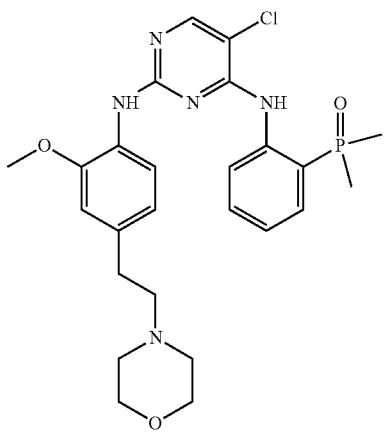

T-6

The following route was used for the synthesis:

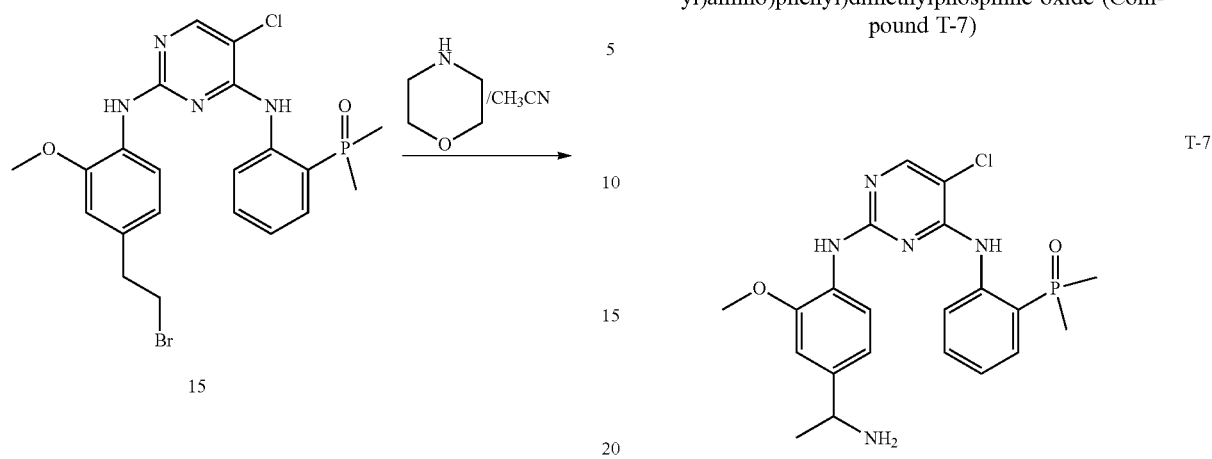

To a 50 mL single-necked flask equipped with a magnetic stirrer compound 15 (102 mg, 0.2 mmol) and acetonitrile (2 mL) were added, and the mixture was stirred to form a solution, morpholine (52 mg, 0.6 mmol) was added, and the reaction was stirred at room temperature under a nitrogen atmosphere overnight. The solvent was distilled off under reduced pressure, and the residue was passed through a silica gel column to obtain 60 mg of a white solid. Yield: 58.2%. LC-MS(APCI): m/z=516.2 (M+1)$^+$. $^1$H NMR (400 MHz, DMSO-D$_6$) δ ppm: 11.18 (s, 1H), 8.48-8.45 (m, 1H), 8.13 (s, 1H), 8.10 (s, 1H), 7.64 (d, J=8.0 Hz, 1H), 7.59-7.54 (m, 1H), 7.41 (t, J=8.0 Hz, 1H), 7.14 (t, J=8.0 Hz, 1H), 6.96 (s, 1H), 6.76 (d, J=8.0 Hz, 1H), 3.80 (s, 3H), 3.60 (t, J=8.4 Hz, 4H), 2.74 (t, J=8.0 Hz, 2H), 2.54 (t, J=8.0 Hz, 2H), 2.45 (t, J=8.0 Hz, 4H), 1.79 (s, 3H), 1.76 (s, 3H).

Example 7 Preparation of (2-((2-((4-(1-aminoethyl)-2-methoxyphen yl)amino)-5-chloropyrimidin-4-yl)amino)phenyl)dimethylphosphine oxide (Compound T-7)

The following route was used for the synthesis:

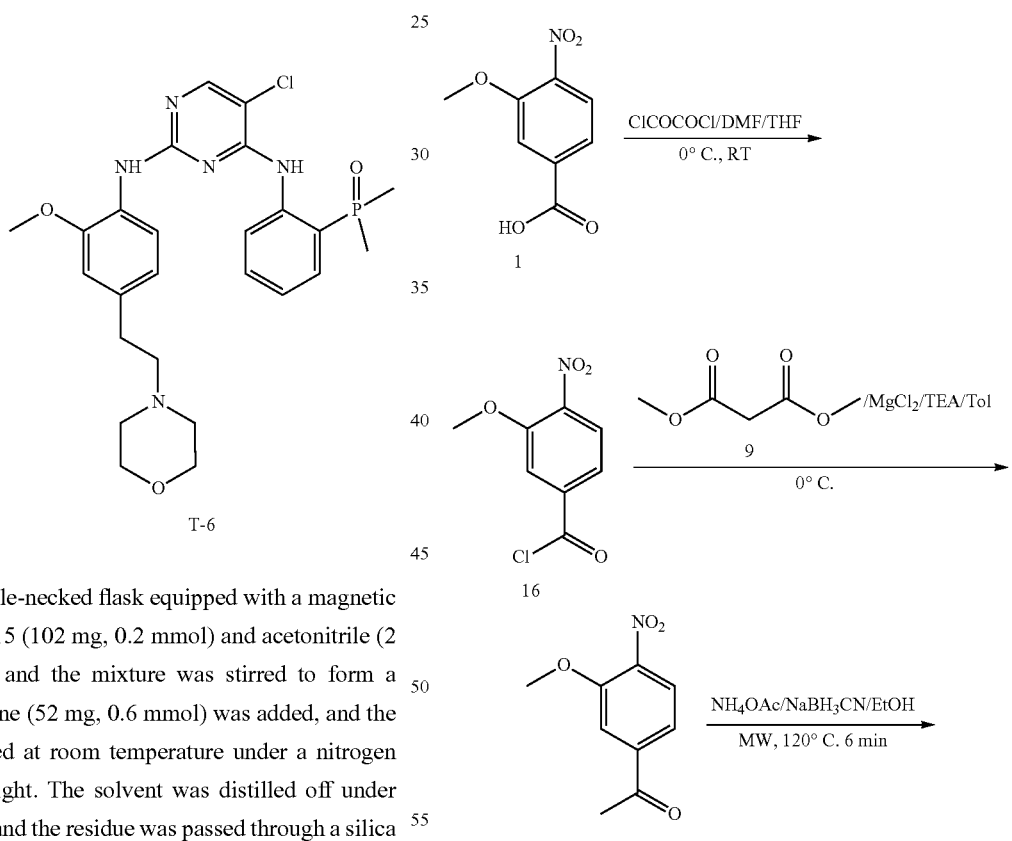

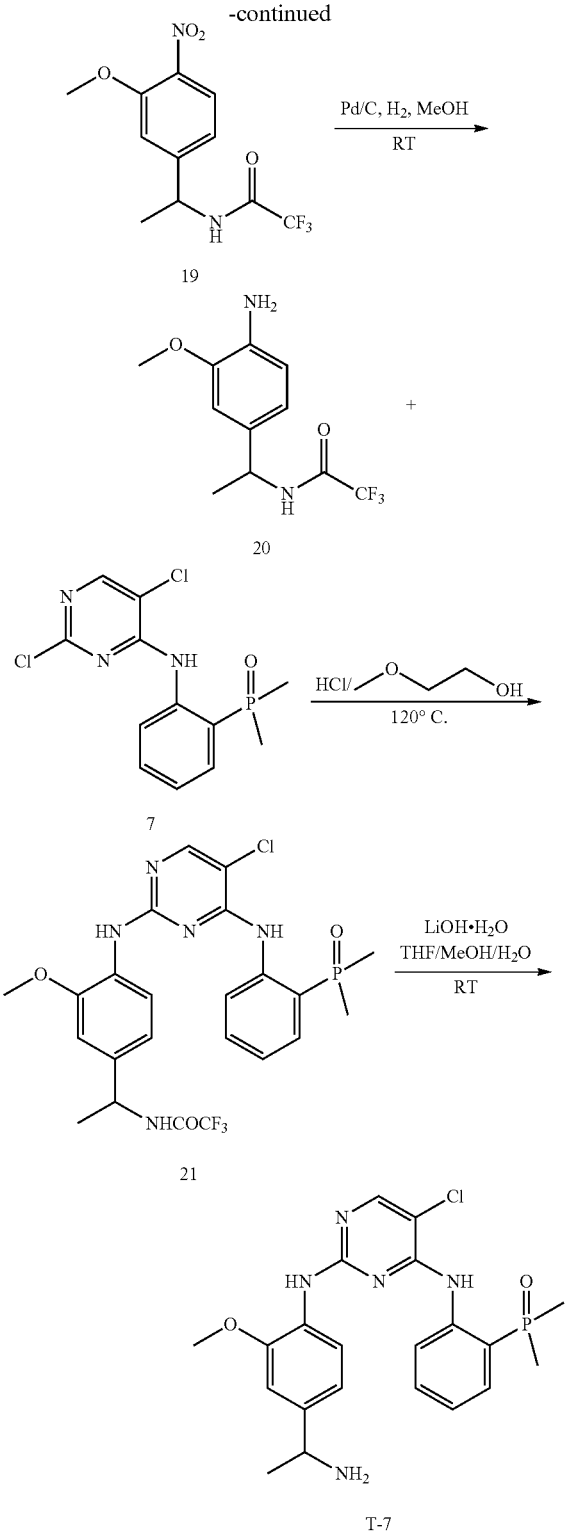

Step 1 Synthesis of compound 17

To a 100 mL three-neck flask equipped with a magnetic stirrer compound 1 (2.75 g, 13.95 mmol) and anhydrous THF (20 mL) were added in sequence, and the mixture was stirred to form a solution. After cooled to 0° C. under a nitrogen atmosphere, anhydrous DMF was added dropwise (3 drops), and then, a solution of oxalyl chloride in dichloromethane (16.74 mmol, 8.37 mL, 2M) was slowly added dropwise. After the addition, the ice bath was removed, and the reaction was stirred at room temperature for 1 hour. The solvent was distilled off under reduced pressure and the residue was dissolved in toluene (40 mL). Under stirring and under nitrogen, $MgCl_2$ (927 mg, 9.74 mmol) and triethylamine (3.38 g, 334.4 mmol) were added with stirring under a nitrogen atmosphere, and then compound 9 (2.21 g, 16.7 mmol) was slowly added, the reaction mixture was stirred at room temperature overnight. The solvent was distilled off under reduced pressure, and the residue was passed through a silica gel column to obtain 1.68 g of a light yellow solid. Yield: 61.7%. LC-MS(APCI): m/z=196.1 (M+1)$^+$.

Step 2 Synthesis of Compound 18

To a 20 mL microwave tube equipped with a magnetic stirrer compound 17 (500 mg, 2.56 mmol) and ethanol (10 mL) were added, and the mixture was stirred to form a solution. Ammonium acetate (1.97 g, 25.62 mmol) and NaBFLCN (322 mg, 5.12 mmol) were added, the reaction mixture was placed in a microwave reactor and heated to a temperature of 120° C., and the reaction was stirred for 10 minutes. The reaction was cooled to room temperature, the solvent was distilled off, and the residue was passed through a silica gel column to obtain 500 mg of colorless oil. Yield: 99.5%. LC-MS(APCI): m/z=197.1 (M+1)$^+$.

Step 3 Synthesis of Compound 19

To a 50 mL single-necked flask equipped with a magnetic stirrer compound 18 (500 mg, 2.55 mmol) and dichloromethane (10 mL) were added, and the mixture was stirred to form a solution. Triethylamine (1.29 g, 12.74 mmol) was added, and trifluoroacetic anhydride (TFAA, 1.07 g, 5.1 mmol) was added dropwise to the solution under ice-water bath, after the addition was finished, the ice bath was removed, and the reaction was stirred at room temperature for 30 minutes under a nitrogen atmosphere. The solvent was distilled off under reduced pressure, and the residue was passed through a silica gel column to obtain 230 mg of a pale yellow solid. Yield: 30.9%. LC-MS(APCI): m/z=293.2 (M+1)$^+$. $^1$H NMR (300 MHz, CDCl$_3$) δ (ppm): 7.88 (d, J=6.3 Hz, 1H), 7.04 (d, J=1.2 Hz, 1H), 6.99 (dd, J=6.6 Hz, J=1.2 Hz, 1H), 5.16 (t, J=5.4 Hz, 1H), 3.99 (s, 3H), 1.63 (t, J=5.4 Hz, 3H).

Step 4 Synthesis of Compound 20

To a 50 mL single-necked flask equipped with a magnetic stirrer compound 19 (230 mg, 0.79 mmol) and methanol (10 mL) were added, and the mixture was stirred to form a solution. Pd/C (50 mg, 60%) was added, then the reaction was vacuumed and purged with hydrogen three times. The reaction was stirred overnight at room temperature under a balloon of hydrogen gas. The catalyst was filtered off, the filter cake was washed with methanol (5 mL), and the solvent was distilled off to obtain 180 mg of a yellow solid. Yield: 87.2% LC-MS(APCI): m/z=263.2 (M+1)$^+$.

Step 5 Synthesis of Compound 21

To a 50 mL single-necked flask equipped with a magnetic stirrer and a condenser tube compound 20 (180 mg, 0.69 mmol), compound 7 (239 mg, 0.75 mmol) and ethylene glycol monomethyl ether (3 mL) were added, and the mixture was stirred to form a solution. A solution of hydrogen chloride in isopropanol (1.03 mmol, 0.21 mL, 5M) was added dropwise, and the temperature was raised to 120° C. under a nitrogen atmosphere and the reaction was stirred at this temperature overnight. The reaction was cooled to room temperature, water (10 mL) and saturated sodium bicarbonate (5 mL) were added, and the solution was extracted with dichloromethane (20 mL×3). The organic phases were combined, washed with saturated brine, dried over anhydrous sodium sulfate, filtered, concentrated, and the residue was passed through a silica gel column to give 0.3 g of a white solid. Yield: 80.6%. LC-MS(APCI): m/z=542.2 (M+1)⁺.

Step 6 Synthesis of Compound T-7

To a 50 mL single-necked flask equipped with a magnetic stirrer compound 21 (300 mg, 0.55 mmol) and THF/MeOH/H$_2$O (2 mL/1 mL/1 mL) were added, and the mixture was stirred to form a solution. Lithium hydroxide monohydrate (LiOH.H$_2$O, 116 mg, 2.77 mmol) was added, and the reaction mixture was stirred overnight at room temperature. Water (10 mL) was added, and the solution was extracted with dichloromethane (15 mL×3). The organic phases were combined, dried over anhydrous sodium sulfate, filtered, and concentrated, and the residue was passed through a silica gel column to obtain 0.2 g of a white solid. Yield: 81.0%. LC-MS(APCI): m/z=446.3 (M+1)⁺. ¹H NMR (300 MHz, DMSO-d$_6$) δ (ppm): 11.19 (s, 1H), 8.47 (dd, J=6.3 Hz, J=3.3 Hz, 1H), 8.15 (s, 2H), 8.03 (br s, 2H), 7.84 (d, J=6.3 Hz, 1H), 7.56 (dd, J=10.2 Hz, J=5.7 Hz, 1H), 7.48 (t, J=5.7 Hz, 1H), 7.26 (s, 1H), 7.15 (t, J=5.4 Hz, 1H), 6.399 (d, J=6.0 Hz, 1H), 4.33 (d, J=5.1 Hz, 1H), 3.84 (s, 3H), 1.76 (d, J=9.9 Hz, 6H), 1.50 (d, J=5.1 Hz, 3H).

Example 8 and Example 9 Preparation of (2-((5-chloro-2-((4-(1-(dimethylamino)ethyl)-2-methoxyphenyl)amino)pyrimidin-4-yl)amino)phenyl)dimethylphosphine oxide (Compound T-8) and (2-((5-chloro-2-((4-(1-(methylamino)ethyl)-2-methoxyphenyl)amino)pyrimidin-4-yl)amino)phenyl)dimethylphosphine oxide (Compound T-9)

The following route was used for the synthesis:

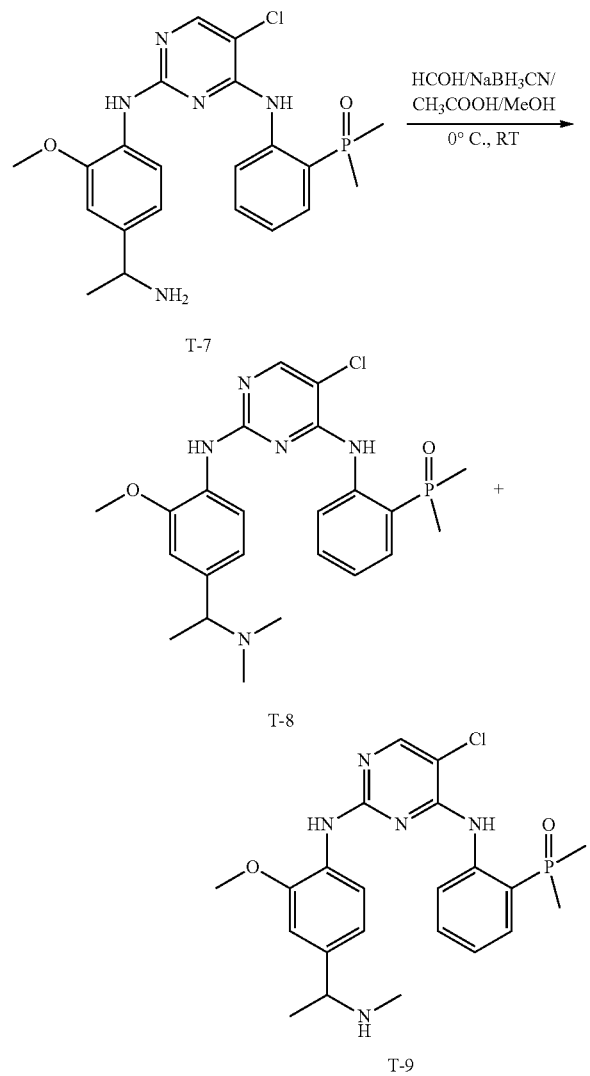

To a 50 mL single-necked flask equipped with a magnetic stirrer compound T-7 (110 mg, 0.25 mmol) and methanol (5 mL), and the mixture was stirred to form a solution. Formaldehyde (14 mg, 0.17 mmol) and glacial acetic acid (1 drop) were added. The reaction was stirred for 10 minutes under a nitrogen atmosphere. The reaction was cooled to 0° C. before NaBH$_3$CN (15 mg, 0.25 mmol) was added, and the reaction mixture was stirred at room temperature for 1 hour. The reaction was quenched by water (10 mL), and extracted with dichloromethane (15 mL×3). The organic phases were combined, dried over anhydrous sodium sulfate, filtered, and concentrated. The residue was passed through a silica gel column to obtain T-8, as 30 mg of a white solid. Yield: 25.7%. LC-MS(APCI): m/z=474.2 (M+1)⁺. ¹H NMR (300 MHz, CDCl$_3$) δ (ppm): 10.87 (s, 1H), 8.58 (dd, J=6.6 Hz, J=3.3 Hz, 1H), 8.41 (d, J=6.3 Hz, 1H), 8.15 (s, 1H), 7.61-7.55 (m, 2H), 7.34-7.31 (m, 2H), 7.18 (t, J=5.4 Hz, 1H), 6.87 (d, J=6.3 Hz, 1H), 4.00 (s, 3H), 3.87 (s, 1H), 2.59 (s, 6H), 1.85 (s, J=9.9 Hz, 6H), 1.68 (s, 3H);

The residue was passed through a silica gel column to obtain T-9 as 17 mg of a white solid. Yield: 15%. LC-MS (APCI): m/z=460.2 (M+1)⁺. ¹H NMR (300 MHz, CDCl$_3$) δ (ppm): 10.84 (s, 1H), 8.56 (dd, J=6.3z, J=3.0z, 1H), 8.42 (d, J=6.3 Hz, 1H), 8.14 (s, 1H), 7.62-7.58 (m, 2H), 7.36-7.27

(m, 2H), 7.19 (dd, J1=5.4 Hz, J2=0.9 Hz, 1H), 6.91 (d, J=6.3 Hz, 1H), 4.08 (d, J=5.1 Hz, 1H), 4.01 (s, 3H), 2.45 (s, 3H), 1.87-1.83 (m, 9H).

Example 10 Preparation of (2-((2-((4-(1-amino-2-methylpropan-2-yl)-2-methoxyphenyl)amino)-5-chloropyrimidin-4-yl)amino)phenyl)dimethylphosphine oxide (Compound T-10)

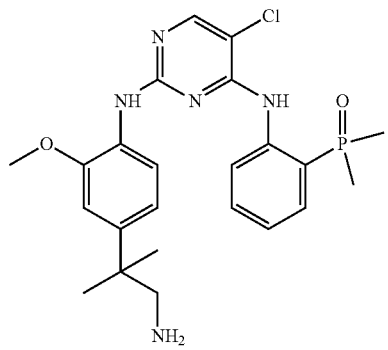

The following route was used for the synthesis:

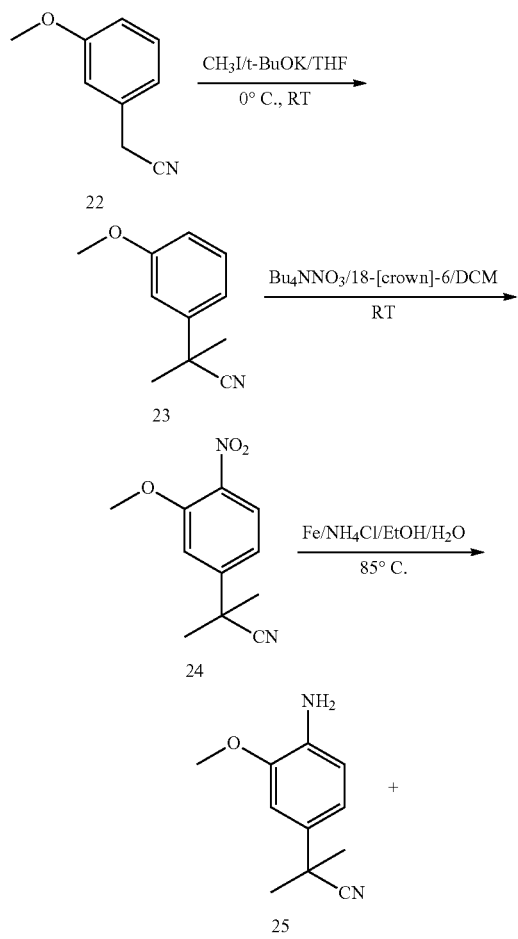

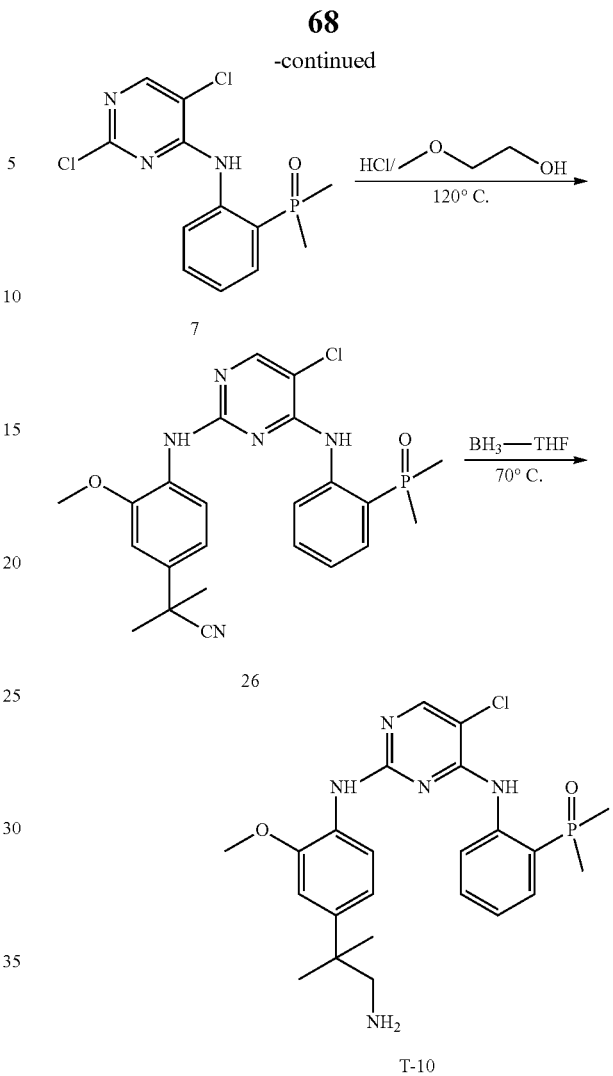

Step 1 Synthesis of Compound 23

To a 50 mL single-necked flask equipped with a magnetic stirrer compound 22 (2 g, 13.6 mmol) and THF (40 mL) were added, and the mixture was stirred to form a solution. After cooled to 0° C., potassium t-butoxide (4.7 g, 40.8 mmol) was added. After stirring for 10 minutes, iodomethane (5.8 g, 40.8 mmol) was added dropwise. After the addition was finished, the ice bath was removed and the reaction was stirred overnight at room temperature under a nitrogen atmosphere. The reaction was quenched by the addition of water (60 mL), and extracted with ethyl acetate (40 mL×3). The organic phases were combined, dried over anhydrous sodium sulfate, filtered, and concentrated. The residue was passed through a silica gel column to obtain 1.84 g of a white solid. Yield: 77.3%. LC-MS(APCI): m/z=176.2 (M+1)$^+$.

Step 2 Synthesis of Compound 24

To a 50 mL single-necked flask equipped with a magnetic stirrer tetrabutylammonium nitrate (6.7 g, 21.94 mmol), 18-crown-6 (845 mg, 3.2 mmol) and dichloromethane (30 mL) were added, and the mixture was stirred to form a solution. After cooled to 0° C., TFAA (13 mL) was added dropwise under a nitrogen atmosphere, and the solution was stirred for 15 minutes. A solution of compound 23 (4.0 g, 22.86 mmol) in dichloromethane (10 mL) was added dropwise, and after the addition, the ice bath was removed, and the reaction was stirred at room temperature for 2 hours, the reaction was quenched by water (30 mL) and saturated aqueous sodium bicarbonate solution (30 mL), and the solution was stirred for 5 minutes. The organic layer was separated, the aqueous phase was extracted with dichloromethane (40 mL×2), the organic phases were combined and dried over anhydrous sodium sulfate, filtered, concentrated, and the residue was passed through a silica gel column to obtain 3.1 g of anhydrous oil. Yield: 61.6%. LC-MS(APCI): m/z=221.1 (M+1)$^+$. $^1$H NMR (400 MHz, CDCl$_3$) δ (ppm): 7.87 (d, J=8.8 Hz, 1H), 7.23 (d, J=2.0 Hz, 1H), 7.09 (dd, J=8.8 Hz, J=2.0 Hz, 1H), 4.00 (s, 3H), 1.76 (s, 6H).

Step 3 Synthesis of Compound 25

To a 100 mL single-necked flask equipped with a magnetic stirrer and a condenser tube compound 24 (3.2 g, 14.9 mmol) and ethanol/water (60 mL, 3/1) were added, and the mixture was stirred to form a solution. Reduced iron powder (70.5 mmol, 3.2 g) and ammonium chloride (14.9 mmol, 790 mg) were added, the reaction was heated to reflux under a nitrogen atmosphere and reacted at this temperature for 1 hour. The reaction was cooled to room temperature, and filtered, and the filter cake was washed with ethanol (10 mL). The resulting solution was concentrated to remove the organic solvent, and extracted with dichloromethane (50 mL×3). The organic phases were combined, dried over anhydrous sodium sulfate, filtered, and concentrated to give 2.6 g of a brown solid. Yield: 91.8%. LC-MS(APCI): m/z=191.1 (M+1)$^+$.

Step 4 Synthesis of compound 26

To a 50 mL single-necked flask equipped with a magnetic stirrer and a condenser tube compound 25 (1.5 g, 7.9 mmol), compound 7 (2.5 g, 7.9 mmol) and ethylene glycol monomethyl ether (15 mL) were added, and the mixture was stirred to form a solution. A solution of hydrogen chloride in isopropanol (11.8 mmol, 2.4 mL, 5M) was added dropwise, and the temperature was raised to 120° C. under a nitrogen atmosphere and the reaction was stirred at this temperature overnight. The reaction was cooled to room temperature, water (30 mL) and saturated sodium bicarbonate (30 mL) were added, and the resulting solution was extracted with dichloromethane (40 mL×3). The organic phases were combined, washed with saturated brine, dried over anhydrous sodium sulfate, filtered, concentrated, and the residue was passed through a silica gel column to give 1.2 g of a white solid. Yield: 32.4%.

LC-MS(APCI): m/z=470.1 (M+1)$^+$.

Step 5 Synthesis of Compound T-10

To a 50 mL single-necked flask equipped with a magnetic stirrer and a condenser tube compound 26 (1.2 g, 2.56 mmol) and THF (10 mL) were added, and the mixture was stirred to form a solution. A borane tetrahydrofuran solution (8 mL, 8.0 mmol, 1M) was added dropwise, under nitrogen atmosphere, the reaction was heat to flux and was stirred at this temperature for 4 hours. The reaction was cooled to room temperature, the solvent was distilled off under reduced pressure, and the residue was passed through a silica gel column to give 460 mg of a white solid. Yield: 38.0%. LC-MS(APCI): m/z=474.2 (M+1)$^+$. $^1$H NMR(400 MHz, CDCl$_3$) δ (ppm): 10.82 (s, 1H), 8.59-8.55 (m, 1H), 8.29 (d, J=8.4 Hz, 1H), 8.08 (s, 1H), 7.58 (t, J=8.4 Hz, 1H), 7.50 (s, 1H), 7.33-7.30 (m, 1H), 7.17-7.14 (m, 1H), 6.88-6.85 (m, 2H), 3.91 (s, 3H), 3.05 (s, 2H), 1.85 (s, 3H), 1.82 (s, 3H), 1.45 (s, 6H).

Example 11 and Example 12 Preparation of (2-((5-chloro-2-((2-methoxy-4-(2-methyl-1-(methylamino) propan-2-yl)phenyl)amino)pyrimidin-4-yl)amino) phenyl)dimethylphosphine oxide (compound T-11) and (2-((5-chloro-2-((4-(1-(dimethylamino)-2-methylpropan-2-yl)-2-methoxyphenyl)amino)pyrimidin-4-yl)amino)phenyl)dimethylphosphine oxide (Compound T-12)

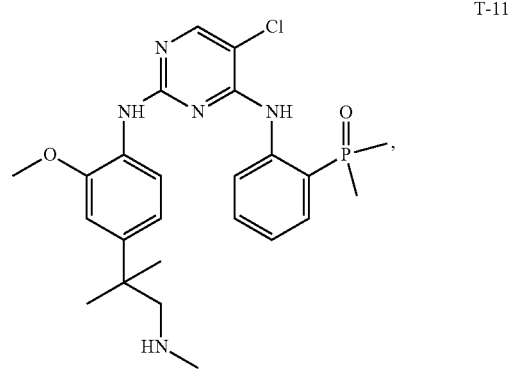

T-11

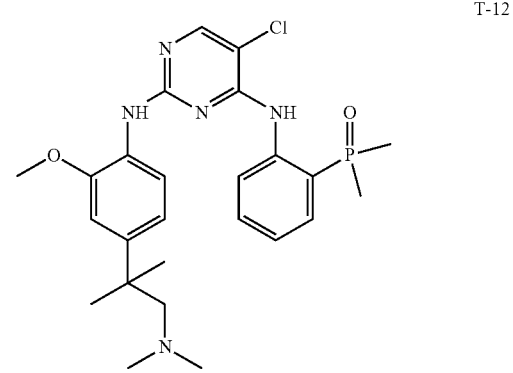

T-12

The following route was used for the synthesis: IDC-51 C3

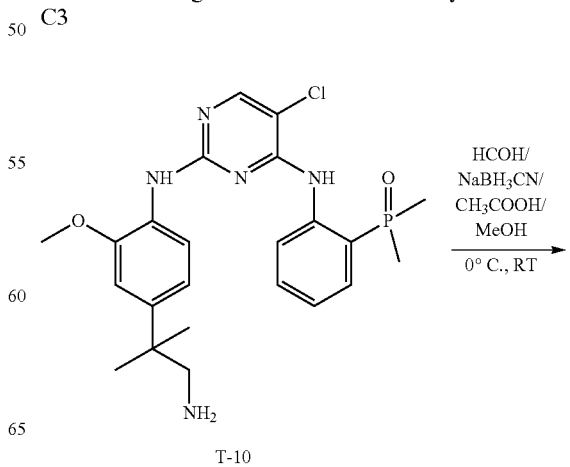

-continued

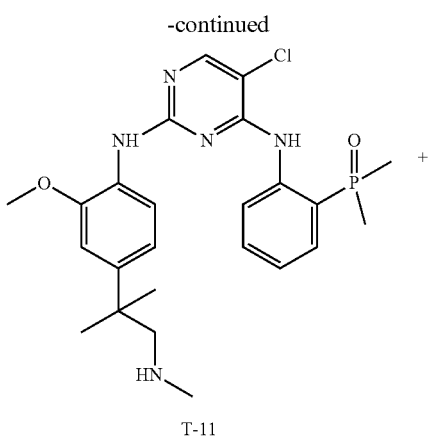

T-11

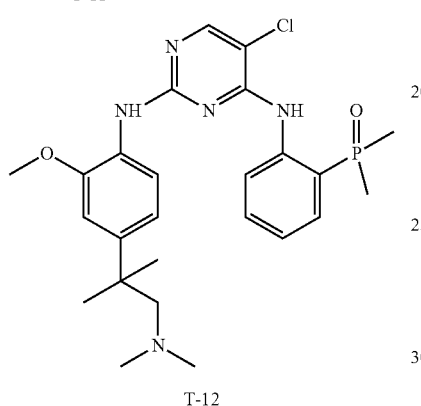

T-12

To a 50 mL single-necked flask equipped with a magnetic stirrer compound T-10 (300 mg, 0.63 mmol) and methanol (10 mL) were added, and the mixture was stirred to form a solution. Formaldehyde (15 mg, 0.5 mmol) and glacial acetic acid (1 drop) were added. The reaction was stirred for 10 minutes under a nitrogen atmosphere. After cooled to 0° C., NaBH$_3$CN (40 mg, 0.63 mmol) was added, and the reaction mixture was stirred at room temperature for 1 hour. The reaction was quenched by adding water (20 mL), and the solution was extracted with dichloromethane (20 mL×3). The organic phases were combined, dried over anhydrous sodium sulfate, filtered, and concentrated. The residue was passed through a silica gel column to give T-11, 50 mg of a white solid. Yield: 16.3%. LC-MS(APCI): m/z=488.2 (M+1)$^+$. $^1$H NMR (400 MHz, CDCl$_3$) δ (ppm): 10.87 (s, 1H), 8.61-8.58 (m, 1H), 8.40 (d, J=8.4 Hz, 1H), 8.14 (s, 1H), 7.59-7.55 (m, 2H), 7.35-7.30 (m, 1H), 7.22-7.17 (m, 1H), 7.03 (d, J=2.0 Hz, 1H), 6.93 (dd, J=8.0 Hz, J=2.0 Hz, 1H), 4.00 (s, 3H), 3.15 (s, 2H), 2.50 (s, 3H), 1.87 (s, 3H), 1.84 (s, 3H), 1.61 (s, 6H);

The residue passing through the silica gel column also gave T-12, 150 mg of a white solid, Yield: 30.0%. LC-MS (APCI): m/z=502.2 (M+1)$^+$. $^1$H NMR (400 MHz, CDCl$_3$) δ (ppm): 10.87 (s, 1H), 8.61-8.58 (m, 1H), 8.40 (d, J=8.4 Hz, 1H), 8.14 (s, 1H), 7.59-7.55 (m, 2H), 7.35-7.30 (m, 1H), 7.22-7.17 (m, 1H), 7.03 (d, J=2.0 Hz, 1H), 6.93 (dd, J=8.0 Hz, J=2.0 Hz, 1H), 4.00 (s, 3H), 3.15 (s, 2H), 2.50 (s, 6H), 1.87 (s, 3H), 1.84 (s, 3H), 1.61 (s, 6H).

Example 13 Preparation of (2-((2-((4-(2-aminopropan-2-yl)-2-methoxyphenyl)amino)-5-chloropyrimidin-4-yl)amino)phenyl)dimethylphosphine oxide (Compound T-13)

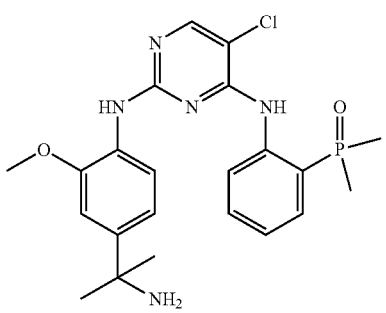

T-13

The following route was used for the synthesis:

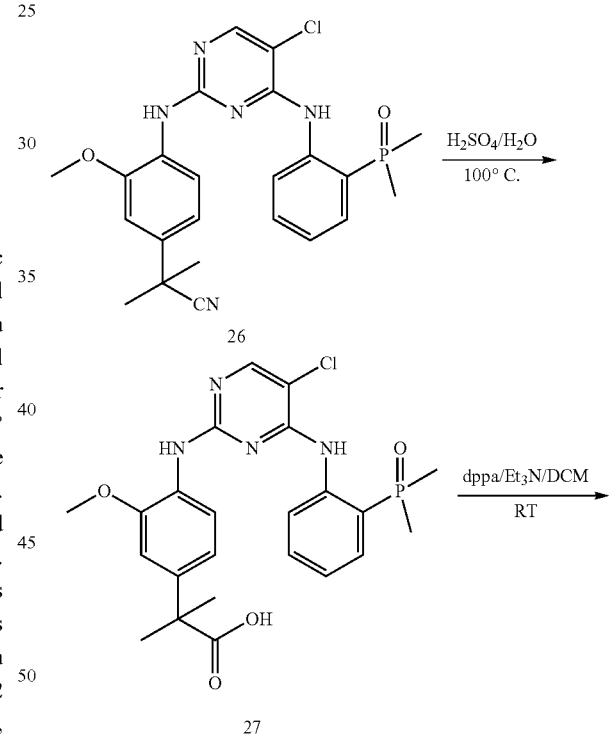

Step 1 Synthesis of Compound 27

To a 50 mL single-necked flask equipped with a magnetic stirrer compound 26 (1.6 g, 3.41 mmol) and water (10 mL) were added, and then concentrated sulfuric acid (10 mL) was added with stirring, and the reaction solution was heated to 100° C. under a nitrogen atmosphere, and was stirred at this temperature overnight. The reaction was cooled to room temperature, the pH thereof was adjusted to about 5 with aqueous NaOH (2M), and the resulting solution was extracted with the dichloromethane (40 mL×3). The organic phases were combined, dried over anhydrous sodium sulfate, filtered, and concentrated. The residue was passed through a silica gel column to obtain 850 mg of a white solid. Yield: 51.1%. LC-MS(APCI): m/z=487.2 (M−1)$^-$.

Step 2 Synthesis of Compound T-13

To a 50 mL single-necked flask equipped with a magnetic stirrer compound 27 (200 mg, 0.41 mmol) and methylene chloride (10 mL) were added, and the mixture was stirred to form a solution. Triethylamine (0.53 mL, 0.53 mmol) was added, and the reaction was stirred under a nitrogen atmosphere for 15 minutes before diphenyl azide phosphate (DPPA, 147 mg, 0.53 mmol) was added, and the reaction was further stirred at room temperature for 3 hours. The solvent was distilled off under reduced pressure, and the residue was dissolved in toluene (10 mL), and the resulted solution was heated to reflux for 2 hours. After cooled to room temperature, hydrochloric acid (20 mL, 6M) was added, and the reaction was refluxed again for 3 hours. The reaction was cooled to room temperature, pH thereof was adjusted to about 10 with aqueous ammonia, and the resulting solution was extracted with ethyl acetate (30 mL×3). The organic phases were combined, dried over anhydrous sodium sulfate, filtered, and concentrated. The residue was passed through a silica gel column to give 110 mg of a white solid. Yield: 58.4%. LC-MS(APCI): m/z=460.2 (M+1)$^+$. $^1$H NMR (400 MHz, DMSO-D$_6$) δ (ppm): 11.20 (s, 1H), 8.50-8.47 (m, 1H), 8.25-8.15 (m, 4H), 7.83 (d, J=8.8 Hz, 1H), 7.60-7.55 (m, 1H), 7.50 (t, J=8.0 Hz, 1H), 7.30 (s, 1H), 7.15 (t, J=8.0 Hz, 1H), 7.03 (dd, J=8.8 Hz. J=2.0 Hz, 1H), 3.87 (s, 3H), 1.79 (s, 3H), 1.75 (s, 3H), 1.63 (s, 6H).

Example 14 and Example 15 Preparation of (2-((5-chloro-2-((4-(2-(dimethylamino)propan-2-yl)-2-methoxyphenyl)amino)pyrimidin-4-yl)amino)phenyl)dimethylphosphine oxide (Compound T-14) and (2-((5-chloro-2-((2-methoxy-4-(2-(methylamino)propan-2-yl)phenyl)amino)pyrimidin-4-yl)amino)phenyl)dimethylphosphine oxide (Compound T-15)

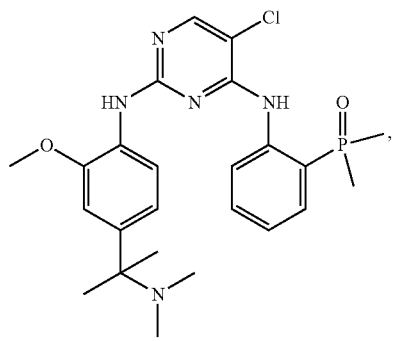

T-14

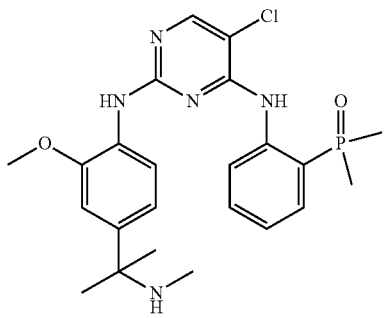

T-15

The following route was used for the synthesis:

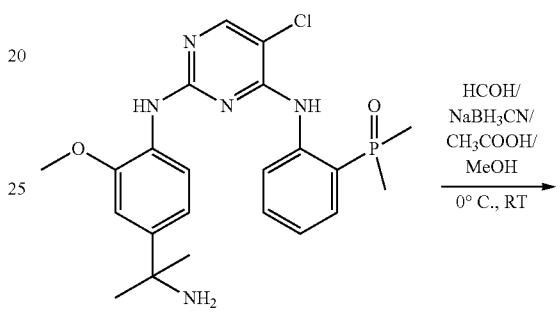

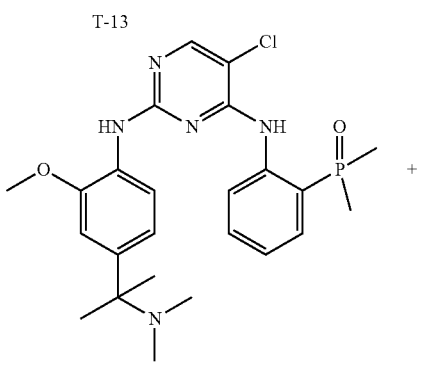

T-14

+

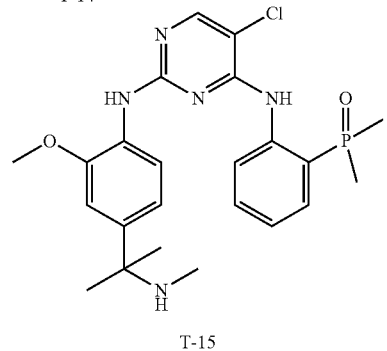

T-15

To a 50 mL single-necked flask equipped with a magnetic stirrer compound T-13 (300 mg, 0.65 mmol) and methanol (10 mL) were added, and the mixture was stirred to form a solution. Formaldehyde (15 mg, 0.5 mmol) and glacial acetic acid (1 drop) were added. The reaction was stirred for 10 minutes under a nitrogen atmosphere. The reaction was cooled to 0° C., to which NaBH$_3$CN (42 mg, 0.65 mmol) was added, and the reaction mixture was stirred at room temperature for 1 hour. The reaction was quenched by adding water (20 mL), and extracted with dichloromethane (20 mL×3). The organic phases were combined, dried over anhydrous sodium sulfate, filtered, and concentrated. The residue was passed through a silica gel column to obtain T-14, 150 mg of a white solid. Yield: 30.0%. LC-MS(APCI): m/z=488.2 (M+1)$^+$. $^1$H NMR (400 MHz, CDCl$_3$) δ (ppm): 10.87 (s, 1H), 8.58-8.57 (m, 1H), 8.42 (d, J=8.4 Hz, 1H), 8.14 (s, 1H), 7.82 (br s, 1H), 7.61 (s, 1H), 7.56 (t, J=8.0 Hz, 1H), 7.31-7.28 (m, 1H), 7.17 (t, J=8.0 Hz, 1H), 6.98 (dd, J=8.4 Hz, J=2.0 Hz, 1H), 4.08 (s, 3H), 2.62 (s, 6H), 1.85 (s, 3H), 1.82 (s, 3H), 1.81 (s, 6H);

The residue passing through the silica gel column also gave T-15, 50 mg of a white solid, Yield: 15.0%. LC-MS (APCI): m/z=474.2 (M+1)$^+$. $^1$H NMR (400 MHz, DMSO-D$_6$) δ (ppm): 11.20 (s, 1H), 9.53 (br s, 1H), 8.47-8.44 (m, 1H), 8.21 (s, 1H), 8.18 (s, 1H), 7.88 (d, J=8.4 Hz, 1H), 7.60-7.55 (m, 1H), 7.51 (t, J=8.0 Hz, 1H), 7.42 (s, 1H), 7.16 (t, J=8.0 Hz, 1H), 7.07 (dd, J=8.8 Hz. J=2.0 Hz, 1H), 3.89 (s, 3H), 2.22 (s, 3H), 1.79 (s, 3H), 1.75 (s, 3H), 1.69 (s, 6H).

Example 16 Preparation of (2-((2-((4-(1-aminopropan-2-yl)-2-methoxyphenyl)amino)-5-chloropyrimidin-4-yl)amino)phenyl)dimethylphosphine oxide (Compound T-16)

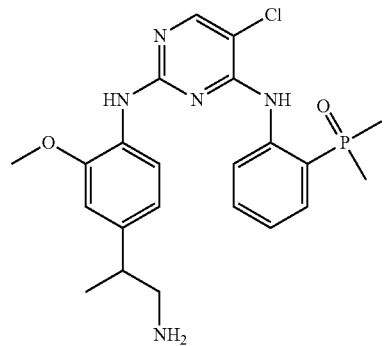

The following route was used for the synthesis:

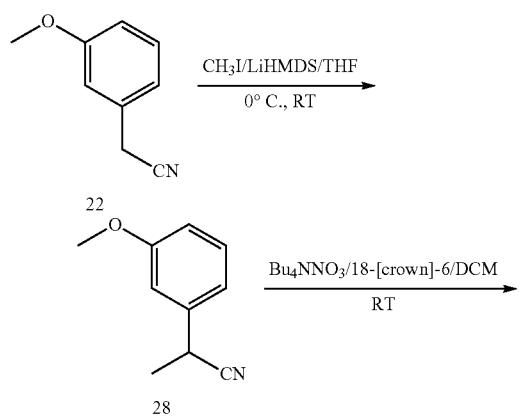

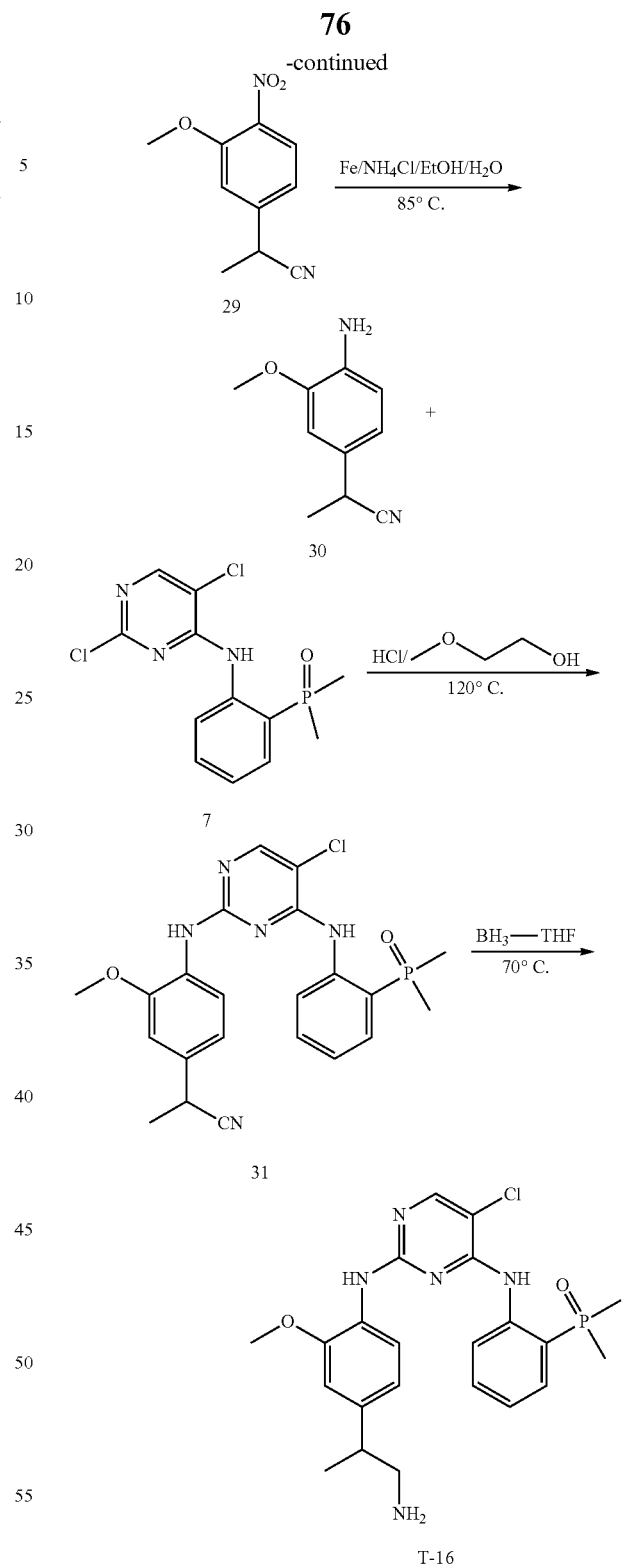

Step 1 Synthesis of Compound 28

To a 50 mL single-necked flask equipped with a magnetic stirrer compound 22 (4 g, 27.2 mmol) and THF (40 mL) were added, and the mixture was stirred to form a solution. After cooled to −10° C., LiHMDS (29.92 mL, 29.92 mmol, 1M) was added dropwise. The solution was stirred for 10 minutes, methyl iodide (4.3 g, 29.92 mmol) was added dropwise. After the addition, the reaction was stirred overnight at room temperature under a nitrogen atmosphere at 0° C. The reaction was quenched by adding water (60 mL), and extracted with ethyl acetate (40 mL×3). The organic phases were combined, dried over anhydrous sodium sulfate, filtered, and concentrated, and the residue was passed through a silica gel column to obtain 3.2 g of a white solid. Yield: 73.5%. LC-MS(APCI): m/z=176.2 (M+1)$^+$. $^1$H NMR (400 MHz, CDCl3) δ (ppm): 7.33-7.28 (m, 1H), 6.96-6.87 (m, 3H), 3.89 (q, J=7.2 Hz, 1H), 3.84 (s, 3H), 1.87 (d, J=7.2 Hz, 3H).

Step 2 Synthesis of Compound 29

To a 50 mL single-necked flask equipped with a magnetic stirrer tetrabutylammonium nitrate (6.7 g, 21.94 mmol), 18-crown-6 (845 mg, 3.2 mmol) and dichloromethane (30 mL) were added, and the mixture was stirred to form a solution. After cooled to 0° C., TFAA (13 mL) was added dropwise under a nitrogen atmosphere, and the solution was stirred for 15 minutes. A solution of compound 28 (3.7 g, 22.86 mmol) in dichloromethane (10 mL) was added dropwise, after the addition was finished, the ice bath was removed. The reaction was stirred at room temperature for 2 hours. The reaction was quenched with water (30 mL) and saturated aqueous sodium bicarbonate solution (30 mL), and the solution was stirred for 5 minutes. The organic layer was separated, and the aqueous phase was extracted with dichloromethane (40 mL×2). The organic phases were combined and dried over anhydrous sodium sulfate, filtered, and concentrated, the residue was passed through a silica gel column to obtain 3.1 g of anhydrous oil. Yield: 68.6%. LC-MS(APCI): m/z=207.1 (M+1)$^+$.

Step 3 Synthesis of Compound 30

To a 100 mL single-necked flask equipped with a magnetic stirrer and a condenser tube compound 29 (3.1 g, 14.9 mmol) and ethanol/water (60 mL, 3/1) were added, and the mixture was stirred to form a solution. Reduced iron powder (70.5 mmol, 3.2 g) and ammonium chloride (14.9 mmol, 790 mg) were added, the reaction was heated to reflux under a nitrogen atmosphere and reacted at this temperature for 1 hour. The reaction was then cooled to room temperature, filtered, the filter cake was washed with ethanol (10 mL), and organic solvent was removed by concentration. The resulting solution was extracted with dichloromethane (50 mL×3). The organic phases were combined, dried over anhydrous sodium sulfate, filtered, and concentrated to give 2.4 g of a brown solid. Yield: 91.5%. LC-MS(APCI): m/z=177.1 (M+1)$^+$.

Step 4 Synthesis of Compound 31

To a 50 mL single-necked flask equipped with a magnetic stirrer and a condenser tube compound 30 (1.4 g, 7.9 mmol), compound 7 (2.5 g, 7.9 mmol) and ethylene glycol monomethyl ether (15 mL) were added, and the mixture was stirred to form a solution. A solution of hydrogen chloride in isopropanol (11.8 mmol, 2.4 mL, 5M) was added dropwise, and the temperature was raised to 120° C. under a nitrogen atmosphere and the reaction was stirred at this temperature overnight. The reaction was then cooled to room temperature, water (30 mL) and saturated sodium bicarbonate (30 mL) were added, and the resulting was extracted with dichloromethane (40 mL×3). The organic phases were combined, washed with saturated brine, dried over anhydrous sodium sulfate, filtered, and concentrated. The residue was passed through a silica gel column to give 1.2 g of a white solid. Yield: 33.4%. LC-MS(APCI): m/z=456.1 (M+1)$^+$.

Step 5 Synthesis of Compound T-16

To a 50 mL single-necked flask equipped with a magnetic stirrer and a condenser tube compound 31 (1.2 g, 2.64 mmol) and THF (10 mL) were added, and the mixture was stirred to form a solution. Aborane tetrahydrofuran solution (8 mL, 8.0 mmol, 1M) was added dropwise, heated to reflux under nitrogen atmosphere and stirred at this temperature for 4 hours. The reaction was cooled to room temperature, the solvent was distilled off under reduced pressure, and the residue was passed through a silica gel column to obtain 460 mg of a white solid. Yield: 37.8%. LC-MS(APCI): m/z=460.2 (M+1)$^+$. $^1$H NMR (400 MHz, CDCl$_3$) δ (ppm): 10.77 (s, 1H), 8.55-8.52 (m, 1H), 8.19 (d, J=8.8 Hz, 1H), 8.02 (s, 1H), 7.53 (t, J=8.0 Hz, 1H), 7.42 (s, 1H), 7.29-7.25 (m, 1H), 7.16-7.14 (m, 1H), 6.79-6.77 (m, 2H), 3.89 (s, 3H), 3.18-3.15 (m, 2H), 3.05-3.02 (m, 1H), 1.84 (d, J=1.6 Hz, 3H), 1.80 (d, J=1.6 Hz, 3H), 1.36 (d, J=6.4 Hz, 3H).

Example 17 and Example 18 Preparation of (2-((5-chloro-2-((4-(1-(dimethylamino)propan-2-yl)-2-methoxyphenyl)amino)pyrimidin-4-yl)amino)phenyl)dimethylphosphine oxide (Compound T-17) and (2-((5-chloro-2-((2-methoxy-4-(1-(methylamino)propan-2-yl)phenyl)amino)pyrimidin-4-yl)amino)phenyl)dimethylphosphine oxide (Compound T-18)

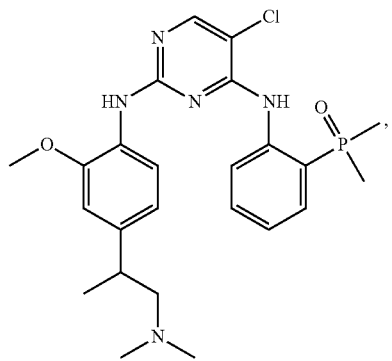

T-17

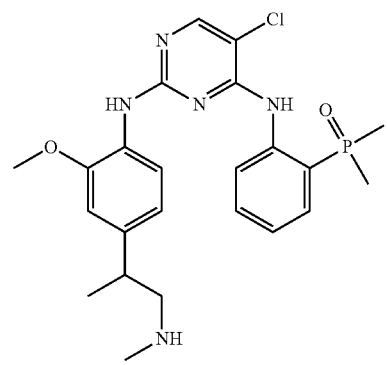

T-18

The following route was used for the synthesis:

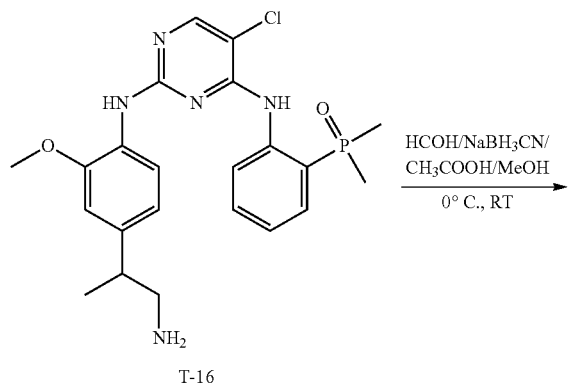

T-16

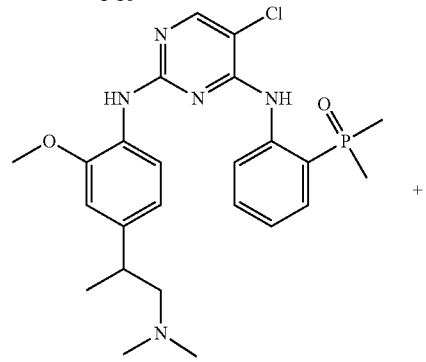

T-17

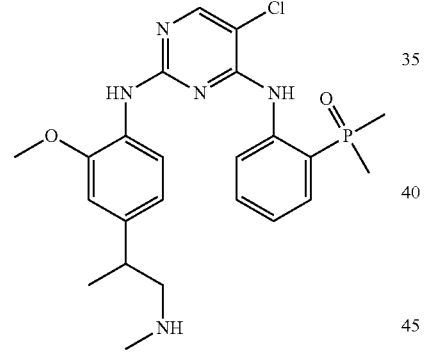

T-18

To a 50 mL single-necked flask equipped with a magnetic stirrer compound T-16 (300 mg, 0.65 mmol) and methanol (10 mL) were added, and the mixture was stirred to form a solution. Formaldehyde (15 mg, 0.5 mmol) and glacial acetic acid (1 drop) were added. The reaction was stirred for 10 minutes under a nitrogen atmosphere. The reaction was then cooled to 0° C., NaBH$_3$CN (42 mg, 0.65 mmol) was added, and the reaction mixture was stirred at room temperature for 1 hour. The reaction was quenched by adding water (20 mL), and the resulting solution was extracted with dichloromethane (20 mL×3). The organic phases were combined, dried over anhydrous sodium sulfate, filtered, and concentrated. The residue was passed through a silica gel column to obtain T-17, 150 mg of a white solid. Yield: 30.0%. LC-MS(APCI): m/z=488.2 (M+1)$^+$. $^1$H NMR (400 MHz, CDCl$_3$) δ (ppm): 10.85 (s, 1H), 8.60-8.58 (m, 1H), 8.34 (d, J=8.4 Hz, 1H), 8.13 (s, 1H), 7.56 (t, J=8.0 Hz, 1H), 7.52 (s, 1H), 7.35-7.29 (m, 1H), 7.21-7.16 (m, 1H), 6.87 (s, 1H), 6.82-6.79 (m, 1H), 3.94 (s, 3H), 3.37-3.32 (m, 1H), 3.10-3.02 (m, 1H), 2.96-2.94 (m, 1H), 2.59 (s, 6H), 1.87 (s, 3H), 1.84 (s, 3H), 1.41 (d, J=6.4 Hz, 3H);

The residue was passing through the silica gel column also gave T-18 as 50 mg of a white solid. Yield: 15.0%. LC-MS(APCI): m/z=474.2 (M+1)$^+$. $^1$H NMR (400 MHz, CDCl$_3$) δ (ppm): 10.85 (s, 1H), 8.60-8.58 (m, 1H), 8.34 (d, J=8.4 Hz, 1H), 8.13 (s, 1H), 7.56 (t, J=8.0 Hz, 1H), 7.52 (s, 1H), 7.35-7.29 (m, 1H), 7.21-7.16 (m, 1H), 6.87 (s, 1H), 6.82-6.79 (m, 1H), 3.94 (s, 3H), 3.37-3.32 (m, 1H), 3.10-3.02 (m, 1H), 2.96-2.94 (m, 1H), 2.59 (s, 3H), 1.87 (s, 3H), 1.84 (s, 3H), 1.41 (d, J=6.4 Hz, 3H).

Example 19 Preparation of (2-((2-((4-(2-amino-ethyl)-2-methoxy-5-methylphenyl)amino)-5-chloro-pyrimidin-4-yl)amino)phenyl)dimethylphosphine oxide (Compound T-19)

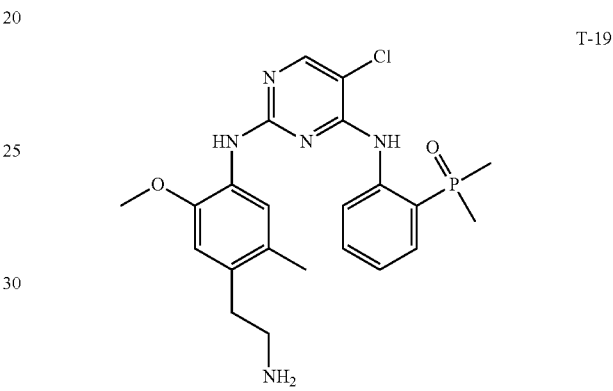

T-19

The following route was used for the synthesis:

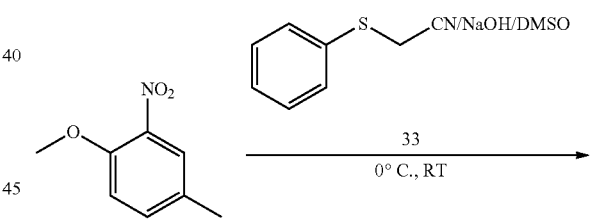

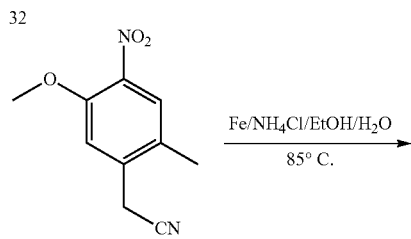

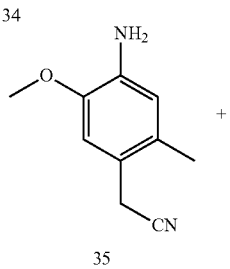

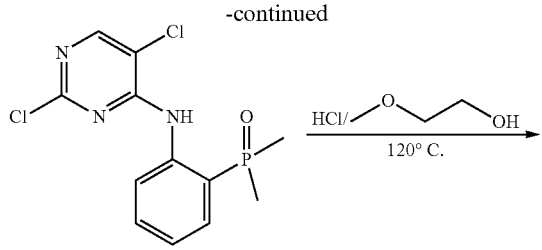

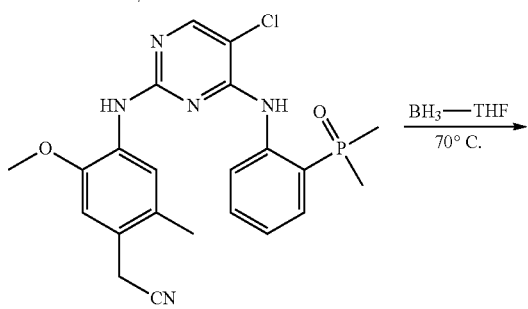

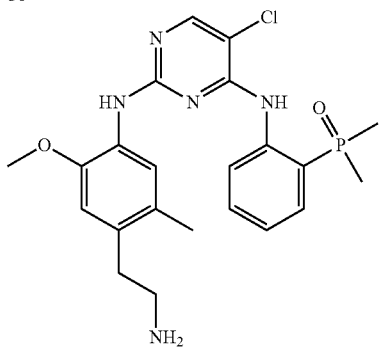

T-19

Step 1 Synthesis of Compound 34

To a 50 mL single-necked flask equipped with a magnetic stirrer NaOH (2.7 g, 67.1 mmol) and DMSO (10 mL) were added, the solution was cooled to 0° C., and compound 32 (1.12 g, 6.71 mmol) and compound 33 (1.0 g, 6.71 mmol) in DMSO (10 mL) was added dropwise, and the reaction mixture was further stirred for 2 hours under nitrogen atmosphere. The reaction was quenched by adding water (50 mL), the resulting solution was extracted with ethyl acetate (40 mL×3), and washed with water (60 mL×2). The organic phases were combined, dried over anhydrous sodium sulfate, filtered, and concentrated. The residue was passed through a silica gel column as 1.3 g of a white solid. Yield: 94.2%. LC-MS(APCI): m/z=207.1 (M+1)⁺.

Step 2 Synthesis of compound 35

To a 100 mL single-necked flask equipped with a magnetic stirrer and a condenser tube compound 34 (3.1 g, 14.9 mmol) and ethanol/water (60 mL, 3/1) were added, and the mixture was stirred to form a solution. Reduced iron powder (70.5 mmol, 3.2 g) and ammonium chloride (14.9 mmol, 790 mg) were added, the reaction was heated to reflux under a nitrogen atmosphere and reacted at this temperature for 1 hour. The reaction was then cooled to room temperature, filtered, and the filter cake was washed with ethanol (10 mL). The organic solvent was removed by concentration, and the resulting solution was extracted with dichloromethane (50 mL×3). The organic phases were combined, dried over anhydrous sodium sulfate, filtered, and concentrated to give 2.4 g of a brown solid. Yield: 91.5%. LC-MS(APCI): m/z=177.1 (M+1)⁺.

Step 3 Synthesis of compound 36

To a 50 mL single-necked flask equipped with a magnetic stirrer and a condenser tube compound 35 (1.4 g, 7.9 mmol), compound 7 (2.5 g, 7.9 mmol) and ethylene glycol monomethyl ether (15 mL) were added, and the mixture was stirred to form a solution. A solution of hydrogen chloride in isopropanol (11.8 mmol, 2.4 mL, 5M) was added dropwise, and the temperature was raised to 120° C. under a nitrogen atmosphere and the reaction was stirred at this temperature overnight. The reaction was then cooled to room temperature, water (30 mL) and saturated sodium bicarbonate (30 mL) were added, and the resulting solution was extracted with dichloromethane (40 mL×3). The organic phases were combined, washed with saturated brine, dried over anhydrous sodium sulfate, filtered, and concentrated, and the residue was passed through a silica gel column to give 1.2 g of a white solid. Yield: 33.4%. LC-MS(APCI): m/z=456.1 (M+1)⁺.

Step 4 Synthesis of compound T-19

To a 50 mL single-necked flask equipped with a magnetic stirrer and a condenser tube compound 31 (1.2 g, 2.64 mmol) and THF (10 mL) were added, and the mixture was stirred to form a solution. Aborane tetrahydrofuran solution (8 mL, 8.0 mmol, 1M) was added dropwise, the reaction was heated to reflux under nitrogen atmosphere and the reaction was stirred and reacted at this temperature for 4 hours. The reaction was then cooled to room temperature, the solvent was distilled off under reduced pressure, and the residue was passed through a silica gel column to obtain 460 mg of a white solid. Yield: 37.8%. LC-MS(APCI): m/z=460.2 (M+1)⁺. ¹H NMR (400 MHz, DMSO-D₆) δ (ppm): 8.47-8.44 (m, 1H), 8.14 (s, 1H), 8.04 (s, 1H), 7.60-7.55 (m, 2H), 7.41 (t, J=8.0 Hz, 1H), 7.16-7.13 (m, 2H), 6.86 (s, 1H), 3.80 (s, 3H), 2.94 (t, J=8.4 Hz, 2H), 2.81 (t, J=8.4 Hz, 2H), 2.17 (s, 3H), 1.79 (s, 3H), 1.76 (s, 3H).

Example 20 and Example 21 Preparation of (2-((5-chloro-2-((4-(2-(dimethylamino)ethyl)-2-methoxy-5-methylphenyl)amino)pyrimidin-4-yl)amino)phenyl)dimethylphosphine oxide (Compound T-20) and (2-((5-chloro-2-((2-methoxy-5-methyl-4-(2-(methylamino)ethyl)phenyl)amino)pyrimidin-4-yl)amino)phenyl)dimethylphosphine oxide (Compound T-21)

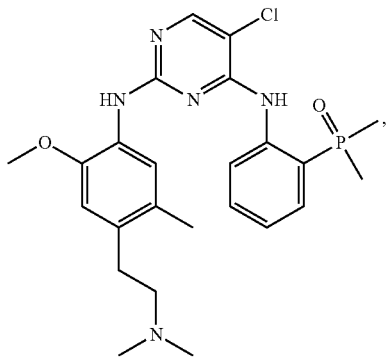

T-20

-continued

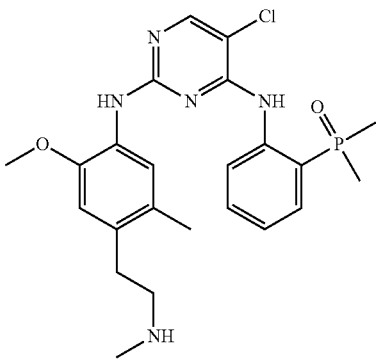

T-21

The following route was used for the synthesis:

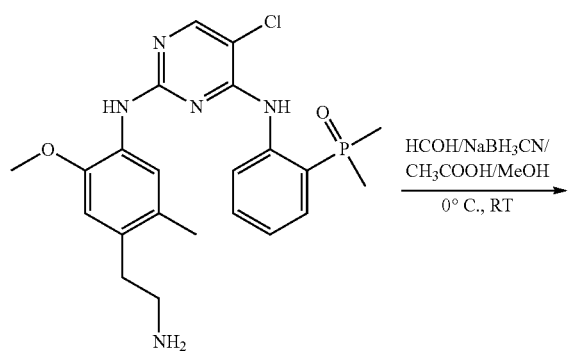

T-19

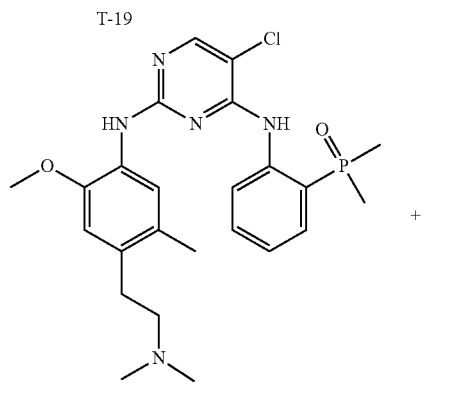

T-20

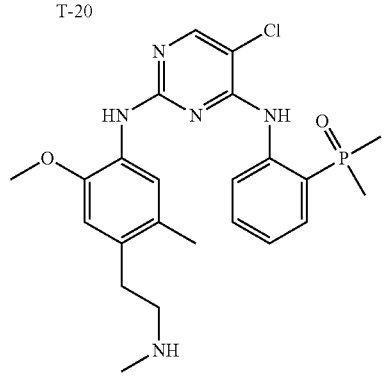

T-21

To a 50 mL single-necked flask equipped with a magnetic stirrer compound T-19 (300 mg, 0.65 mmol) and methanol (10 mL) were added, and the mixture was stirred to form a solution. Formaldehyde (15 mg, 0.5 mmol) and glacial acetic acid (1 drop) were added. The reaction was stirred for 10 minutes under a nitrogen atmosphere. The reaction was cooled to 0° C., NaBH$_3$CN (42 mg, 0.65 mmol) was added, and the reaction mixture was stirred at room temperature for 1 hour. The reaction was quenched by adding water (20 mL), and the resulting solution was extracted with dichloromethane (20 mL×3). The organic phases were combined, dried over anhydrous sodium sulfate, filtered, and concentrated. The residue was passed through a silica gel column to obtain T-20, 150 mg of a white solid. Yield: 30.0%. LC-MS(APCI): m/z=488.2 (M+1)$^+$. $^1$H NMR (400 MHz, CDCl3) δ (ppm): 10.79 (s, 1H), 8.59-8.56 (m, 1H), 8.09-8.08 (m, 2H), 7.48 (t, J=8.0 Hz, 1H), 7.43 (s, 1H), 7.30-7.27 (m, 1H), 7.14-7.10 (m, 1H), 6.68 (s, 1H), 6.82-6.79 (m, 1H), 3.84 (s, 3H), 2.98-2.94 (m, 2H), 2.80-2.73 (m, 2H), 2.58 (s, 6H), 2.20 (s, 3H), 1.83 (s, 3H), 1.81 (s, 3H);

The residue was passing through the silica gel column also gave T-21 as 50 mg of a white solid. Yield: 15.0%. LC-MS(APCI): m/z=474.2 (M+1)$^+$. 10.76 (s, 1H), 8.59-8.56 (m, 1H), 8.09-8.08 (m, 2H), 7.48 (t, J=8.0 Hz, 1H), 7.43 (s, 1H), 7.30-7.27 (m, 1H), 7.14-7.10 (m, 1H), 6.68 (s, 1H), 6.82-6.79 (m, 1H), 3.84 (s, 3H), 2.98-2.94 (m, 2H), 2.80-2.73 (m, 2H), 2.55 (s, 3H), 2.20 (s, 3H), 1.83 (s, 3H), 1.81 (s, 3H).

Example 22 Biological Evaluation of Compounds

The compounds of the present disclosure are evaluated in multiple assays to determine their biological activity. For example, the compounds of the present disclosure may be tested for their ability to inhibit various protein kinases of interest. Some tested compounds showed potent inhibitory activity against ALK kinase.

(1) Evaluation of Kinase Inhibition

Compound preparation: The test compounds were dissolved in DMSO to make 20 mM stock solutions. The compounds were diluted in DMSO to 0.1 mM (a dilution with 100 times the final concentration) before use, and a 3-fold series gradient dilution with 11 concentrations was made. Dilutions with 4 times of the final concentration were prepared by diluting with buffer when dosing.

Kinase assay: after preparing the buffer solution, the enzyme was mixed with pre-diluted compounds with different concentrations, and placed at room temperature for 30 minutes in duplicate. The corresponding substrate and ATP were added thereto and reacted at room temperature for 60 minutes (both a negative and a positive control were set). After the reaction, antibody was added for detection, and after incubation at room temperature for 60 minutes, Evnvision detection was carried out, and data was collected. Data was analyzed and fit according to XLfit5 software. IC$_{50}$ was calculated by the following formula: (IC$_{50}$=[(ABS test−ABS begin)/(ABS control−ABS begin)]×100). Wherein A represents IC$_{50}$≤2 nM, B represents IC$_{50}$ of 2-5 nM, C represents IC$_{50}$ of 5-10 nM.

The compounds of the present disclosure were tested in the above kinase inhibition assay, and were found to have potent activity against ALK and ALK[L1196M]. The results of the representative example compounds are summarized in Table 1 below.

TABLE 1

| Example No. | IC$_{50}$(nM) ALK [WT] | ALK [L1196M] |
|---|---|---|
| 1 | C | C |
| 2 | A | B |
| 3 | A | B |
| 4 | A | B |
| 5 | A | A |
| 6 | B | B |
| 7 | B | B |
| 8 | B | B |
| 9 | B | B |
| 10 | B | B |
| 11 | B | C |
| 12 | B | C |
| 13 | A | A |
| 14 | A | B |
| 15 | A | A |
| 16 | C | C |
| 17 | C | C |
| 18 | | |
| 19 | | |
| 20 | B | B |
| 21 | B | C |

(2) Cytotoxicity Test

The in vitro anti-proliferative activity of the compounds of the present disclosure against three types of cells that are cultured in vitro was tested by CellTiter-Glo method. The experimental results show that the compounds of the present disclosure have potent inhibition on the in vitro proliferation of EML4-ALK and EML4-ALK L1196M mutant cells that cultured in vitro.

Cell lines: BaF3 parental; BaF3 [EML4-ALK] (From WuXi PharmaTech) and BaF3 [EMF4-AFK F1196M] (From WuXi PharmaTech); wherein, BaF3 parental was cultured in RPMI1640 medium containing 10 ng/ml IL-3, 10% fetal bovine serum, 100 U/ml penicillin, and 100 μg/ml streptomycin, BaF3 [EMF4-AFK] and BaF3 [EMF4-AFK F1196M] were cultured in RPMI1640 medium containing 10% fetal bovine serum, 100 U/ml penicillin, and 100 μg/ml streptomycin.

Reagents and materials: RPMI-1640 (GIBCO, Cat. No. A10491-01); fetal bovine serum (GIBCO, Cat. No. 10099141); 0.25% trypsin-EDTA (GIBCO, Cat. No. 25200); penicillin-streptomycin, liquid (GIBCO, Cat. No. 15140-122); DMSO (Sigma, Cat. No. D2650); CellTiter-Glo Test Kit (Promega, Cat. No. G7572), and 96-well plate (Corning, Cat. No. 3365).

Specific Experimental Procedures:

1. The test compounds were dissolved in DMSO to make stock solutions and subjected to a series gradient dilution to give solutions with 10-fold working concentration.

2. The cells in the logarithmic growth phase were diluted with the culture solution to adjust to the specific cell concentration, 90 μi of cell suspension was added to the 96-well plate to make the cell density reach the specified concentration. The plate was incubated in a incubator at 37° C., containing 5% carbon dioxide gas overnight.

3. 10 μl drug solutions were added to each well of the 96-well plate inoculated with cells. 10 concentrations of the compounds were tested starting from the highest concentration of 20 μM with a 3-fold series gradient dilution in duplicate.

4. After continuously cultured for 72 hours, the cells were detected by CellTiter-Glo for the cell viability. The dose-effect curve was made using GraphPad Prism software and IC$_{50}$ was calculated.

The compounds of the present disclosure were tested in the above-mentioned cytotoxicity assay, finding out that the compounds of the present disclosure have potent activity against Ba/F3 AFK and Ba/F3 AFK[F1196M], and superior selectivity over Ba/F3 parental cells. The results of the inhibition effects on the proliferation of cancer cells in vitro by the representative examples compounds of the present disclosure were summarized in Table 2 below, wherein, A represents IC$_{50<25}$ nM, B represents IC$_{50}$ of 25-50 nM, C represents IC$_{50}$ of 50-100 nM, D represents IC$_{50}$ of 100-200 nM, E represents IC$_{50}$ of 200-1000 nM, and F represents IC$_{50}$≥1000 nM.

TABLE 2

| Example No. | IC$_{50}$(nM) parental (Ba/F3) | ALK (Ba/F3) | ALK[L1196M] (Ba/F3) | Selectivity parental/ ALK | parental/ ALK[L1196M] |
|---|---|---|---|---|---|
| 1 | F | C | D | <50 | <50 |
| 2 | F | D | E | <50 | <50 |
| 3 | F | B | D | 50 to 100 | <50 |
| 4 | F | A | C | 200 to 500 | <50 |
| 5 | F | A | B | 200 to 500 | 100 to 200 |
| 6 | F | A | D | 200 to 500 | <50 |
| 7 | F | C | E | <50 | <50 |
| 8 | F | B | D | 100 to 200 | <50 |
| 9 | F | C | E | 50 to 100 | <50 |
| 10 | F | B | D | 100 to 200 | <50 |
| 11 | F | B | C | 100 to 200 | 50 to 100 |
| 12 | F | B | C | 100 to 200 | <50 |
| 13 | F | B | D | <50 | <50 |
| 14 | F | A | C | 100 to 200 | <50 |
| 15 | F | C | D | <50 | <50 |
| 16 | F | E | E | 50 to 100 | <50 |
| 17 | F | B | D | 100 to 200 | 50 to 100 |
| 20 | F | B | B | 50 to 100 | 50 to 100 |
| 21 | F | D | E | <50 | <50 |

(3) Metabolic Stability Evaluation

Experiments in microsomes: Human liver microsomes: 0.5 mg/mL, Xenotech; Rat liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solution: Powder of the example compounds was accurately weighed and dissolved in DMSO to 5 mM. Preparation of phosphate buffer (100 mM, pH7.4): A pre-formulated 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH7.4. A NADPH regeneration system solution (containing 6.5 mM NADP, 16.5 mM G-6-P, 3 U/mL G-6-PD, 3.3 mM magnesium chloride) was prepared and placed on wet ice prior to use. Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL human liver microsomes were added, and mixed to obtain a liver microsome dilution solution with a protein concentration of 0.625 mg/mL. 25057.5 μL of phosphate buffer (pH 7.4) was taken into a 50 mL centrifuge tube, to which 812.5 μL SD rat liver microsomes were added, and mixed to obtain a liver microsome dilution solution with a protein concentration of 0.625 mg/mL.

Incubation of the samples: The stock solution of the respective compound was respectively diluted to 0.25 mM with an aqueous solution containing 70% acetonitrile, and used as a working solution, ready for use. 398 μL of the dilution solution of human liver microsomes or rat liver microsome were added to a 96-well incubation plate (N=2), respectively, and 2 μL of 0.25 mM working solution was added and mixed.

Metabolic stability assay: 300 μL of pre-chilled stop solution was added to each well of a 96-well deep well plate and placed on ice as a stop plate. The 96 well incubation plate and NADPH regeneration system were placed in a 37° C. water bath box, shaken at 100 rpm and pre-incubated for 5 min. 80 μL of incubation solution was taken out from each well of the incubation plate and added to the stop plate, mixed, and replenished with 20 μL of NADPH regeneration system solution as a 0-min sample. 80 μL of NADPH regeneration system solution was added to each well of the incubation plate to start the reaction and start counting. The corresponding compound had a reaction concentration of 1 μM and the protein concentration was 0.5 mg/mL. Separately, 100 μL of the reaction solution was taken at 10, 30, and 90 min reaction, respectively, added to a stop plate, and vortexed for 3 minutes to terminate the reaction. The stop plate was centrifuged at 5000×g at 4° C. for 4 min. 100 μL of the supernatant was added to a 96-well plate to which 100 μL of distilled water was previously added, mixed, and analyzed by LC-MS/MS.

Data analysis: The peak areas of the corresponding compound and internal standard were detected by LC-MS/MS system, and the ratio of the peak area of the compound to the internal standard was calculated. The slope was measured by plotting the natural logarithm of the percent of compound remaining versus time, and $t_{1/2}$ and $CL_{int}$ were calculated according to the formula, where V/M is equal to 1/protein concentration.

$$t_{1/2} = -\frac{0.693}{\text{slope}}, \quad CL_{int} = \frac{0.693}{t_{1/2}} \cdot \frac{V}{M}, \quad t_{1/2}(\text{min}); CL_{int}(\mu L/\text{min}/\text{mg}).$$

The compounds of the present disclosure were evaluated for their metabolic stability in human and rat liver microsomes. The half-life and the intrinsic liver clearance rate as indicators of metabolic stability are shown in Table 3 below. The compound of the present disclosure can significantly improve the metabolic stability.

TABLE 3

| Example No. | Human liver microsome experiment | | Rat liver microsome experiment | |
|---|---|---|---|---|
| | $t_{1/2}$ (min) | $CL_{int}$ (uL/min/mg) | $t_{1/2}$ (min) | $CL_{int}$ (uL/min/mg) |
| 1 | 131.2 | 10.6 | 31.9 | 43.4 |
| 2 | 159.6 | 8.7 | 164.6 | 8.4 |
| 3 | 90.1 | 15.4 | 27.5 | 50.4 |
| 4 | 51.9 | 26.7 | 39.9 | 34.7 |
| 5 | 80.0 | 17.3 | 38.6 | 35.9 |
| 6 | 47.6 | 29.1 | 16.3 | 85.1 |
| 7 | 243.9 | 5.7 | 340.3 | 4.1 |
| 8 | 56.3 | 24.6 | 48.2 | 28.8 |
| 9 | 123.1 | 11.3 | 139.6 | 9.9 |
| 10 | 55.0 | 25.2 | 92.0 | 15.1 |
| 11 | 58.2 | 23.8 | 193.7 | 7.2 |
| 12 | 18.9 | 73.5 | 16.0 | 86.8 |
| 13 | 118.8 | 11.7 | 152.3 | 9.1 |
| 14 | 46.4 | 29.9 | 41.5 | 33.4 |
| 15 | 66.9 | 20.7 | 78.8 | 17.6 |
| 16 | 64.6 | 21.5 | 118.4 | 11.7 |
| 17 | 74.3 | 18.6 | 46.7 | 29.7 |
| 20 | 258.8 | 5.4 | 42.9 | 32.3 |
| 21 | 50.0 | 27.7 | 192.7 | 7.2 |

(4) Pharmacokinetic Experiment in Rats 6 male Sprague-Dawley rats (7-8 weeks old, and weighing approximately 210 g) were divided into 2 groups with 3 rats in each group. The rats were intravenously or orally administered a single dose of compound (10 mg/kg orally) to compare pharmacokinetic differences.

The rats were raised on standard food and water. Fasting was started 16 hours before the test. The drug was dissolved with PEG400 and dimethyl sulfoxide. The blood samples were collected from eyelids at the time points of 0.083 hours, 0.25 hours, 0.5 hours, 1 hour, 2 hours, 4 hours, 6 hours, 8 hours, 12 hours, and 24 hours after administration.

Rats were briefly anesthetized after inhalation of diethyl ether and 300 μL of blood sample was collected from the eyelids into test tubes. There was 30 μL of 1% heparin salt solution in the test tube. Tubes were dried at 60° C. overnight before use. After the blood sample was collected at the last time point, the rats were sacrificed after ether anesthesia.

Immediately after the collection of the blood sample, the test tube was gently inverted at least 5 times to ensure sufficient mixing and then placed on ice. The blood sample was centrifuged at 5000 rpm at 4° C. for 5 minutes to separate the plasma from the red blood cells. 100 μL of plasma was aspirated into a clean plastic centrifuge tube with a pipette, marking with the name of the compound and time point. Plasma was stored at −80° C. prior to analysis. The concentration of the compound of the present disclosure in plasma was determined by LC-MS/MS. The pharmacokinetic parameters were calculated based on the blood concentration of each animal at different time points.

Experiments showed that the compounds of the present disclosure have better pharmacokinetic properties in animals, and therefore have better pharmacodynamics and treatment effects.

The above is a further detailed description of the present disclosure in conjunction with specific embodiments, and it cannot be assumed that the specific implementation of the present disclosure is limited to these descriptions. For ordinary artisan in the technical field to which the present disclosure belongs, without deviating from the concept of the present disclosure, various simple deductions or replacements may be made, which should be regarded as falling within the protection scope of the present disclosure.

The invention claimed is:

1. A compound of formula (I):

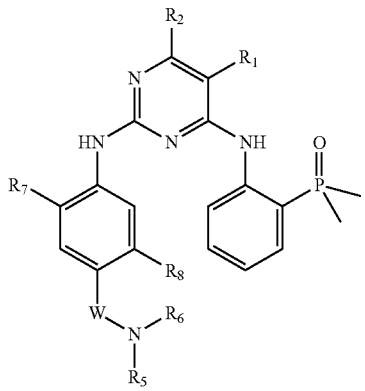

wherein,

R₁ and R₂ are independently selected from H, halogen, —CN, —NO₂, —OH, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl, and optionally substituted 3- to 10-membered heterocyclyl;

linker W is $C_1$-$C_6$ alkylene which is optionally substituted with one or more R₃;

R₃ is selected from H, halogen, —CN, $C_1$-$C_6$ alkyl, and $C_1$-$C_6$ haloalkyl;

R₅ and R₆ are independently selected from H, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl and optionally substituted 3- to 10-membered heterocyclyl;

R₇ is selected from optionally substituted $C_1$-$C_6$ alkoxy, optionally substituted $C_1$-$C_6$ haloalkoxy, optionally substituted $C_2$-$C_6$ alkenyloxy, and optionally substituted 3- to 7-membered cycloalkyloxy; and R₈ is selected from H, halogen, and $C_1$-$C_6$ alkyl;

or a pharmaceutically acceptable salt, a crystal form, a prodrug, a metabolite, a hydrate, a solvate, a stereoisomer, or an isotopic derivative thereof.

2. The compound according to claim 1, wherein

R₁ is selected from H, halogen, —CN, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl, and optionally substituted 3- to 10-membered heterocyclyl; and R₂ is selected from H, halogen, —CN, —NO₂, —OH, optionally substituted $C_1$-$C_6$ alkyl, and optionally substituted $C_1$-$C_6$ alkoxy;

or a pharmaceutically acceptable salt, a crystal form, a prodrug, a metabolite, a hydrate, a solvate, a stereoisomer, or an isotopic derivative thereof.

3. The compound according to claim 2, which is of the following formula:

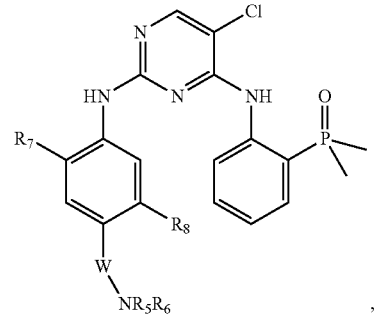

wherein,

W is $C_1$-$C_6$ alkylene which is optionally substituted with one or more R₃;

R₃ is selected from H, $C_1$-$C_6$ alkyl, and $C_1$-$C_6$ haloalkyl;

R₅ and R₆ are independently selected from H, optionally substituted $C_1$-$C_6$ alkyl, optionally substituted $C_1$-$C_6$ haloalkyl, optionally substituted $C_1$-$C_6$ alkoxy, optionally substituted $C_3$-$C_{10}$ carbocyclyl, and optionally substituted 3- to 10-membered heterocyclyl;

R₇ is selected from optionally substituted $C_1$-$C_6$ alkoxy, optionally substituted $C_1$-$C_6$ haloalkoxy, and optionally substituted 3- to 7-membered cycloalkyloxy; and R₈ is selected from H, halogen, and $C_1$-$C_6$ alkyl;

or a pharmaceutically acceptable salt, a crystal form, a prodrug, a metabolite, a hydrate, a solvate, a stereoisomer, or an isotopic derivative thereof.

4. The compound according to claim 1, wherein W is selected from —CH₂—, —CH₂CH₂—, —C(CH₃)H—, —C(CH₃)₂—, —C(CH₃)HCH₂—, —C(CH₃)₂CH₂—, —C(CH₃)HC(CH₃)H—, and —C(CH₃)₂C(CH₃)₂;

or a pharmaceutically acceptable salt, a crystal form, a prodrug, a metabolite, a hydrate, a solvate, a stereoisomer, or an isotopic derivative thereof.

5. The compound according to claim 1, wherein

R₅ and R₆ are independently selected from H, and optionally substituted $C_1$-$C_6$ alkyl;

or a pharmaceutically acceptable salt, a crystal form, a prodrug, a metabolite, a hydrate, a solvate, a stereoisomer, or an isotopic derivative thereof.

6. The compound according to claim 1, wherein

—W—NR₅R₆ is selected from:

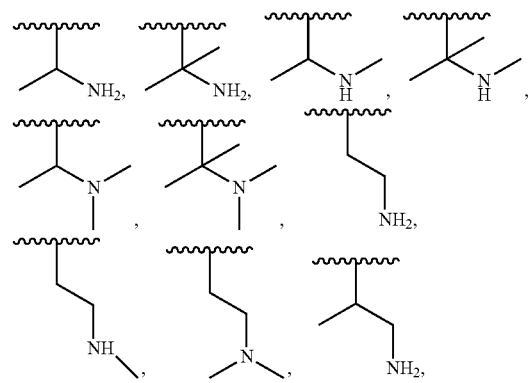

-continued

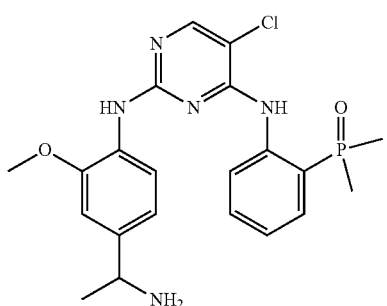

or a pharmaceutically acceptable salt, a crystal form, a prodrug, a metabolite, a hydrate, a solvate, a stereoisomer, or an isotopic derivative thereof.

7. The compound according to claim 1, wherein $R_7$ is selected from —$OCH_3$, —$OCH_2CH_3$, —$OCH_2CH_2CH_3$, —$OCH(CH_3)_2$, —$OCF_3$, —$OCHF_2$, —$OCH_2F$, and —$OCH_2CF_3$;
or a pharmaceutically acceptable salt, a crystal form, a prodrug, a metabolite, a hydrate, a solvate, a stereoisomer, or an isotopic derivative thereof.

8. The compound according to claim 1, wherein $R_8$ is selected from H and $C_1$-$C_6$ alkyl;
or a pharmaceutically acceptable salt, a crystal form, a prodrug, a metabolite, a hydrate, a solvate, a stereoisomer, or an isotopic derivative thereof.

9. The compound according to claim 1, wherein the compound is selected from:

formula (1)

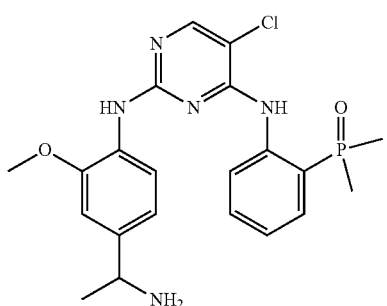

formula (2)

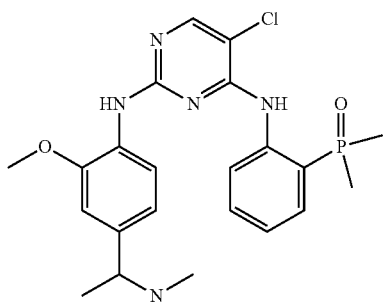

formula (3)

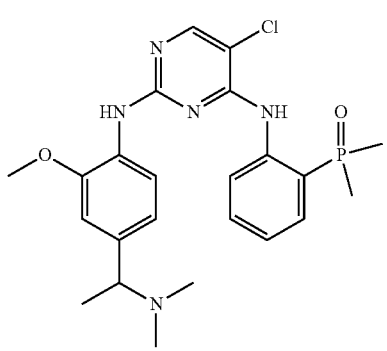

formula (4)

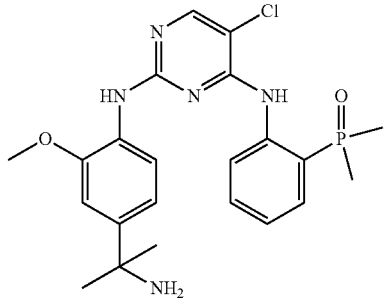

formula (5)

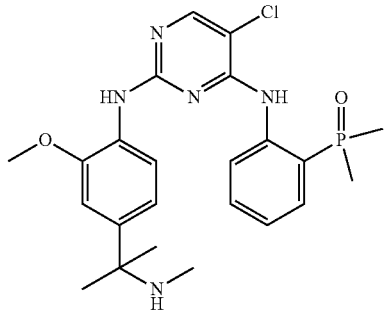

formula (6)

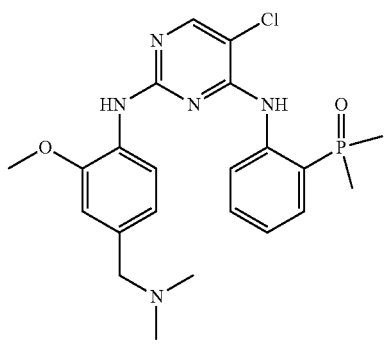

formula (7)

formula (8)
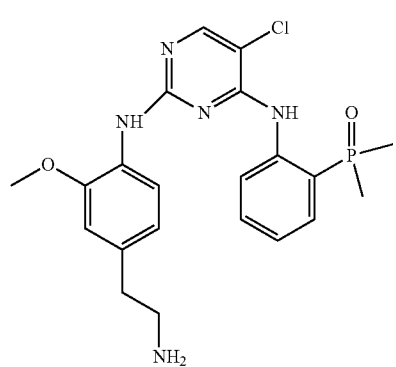
formula (9)
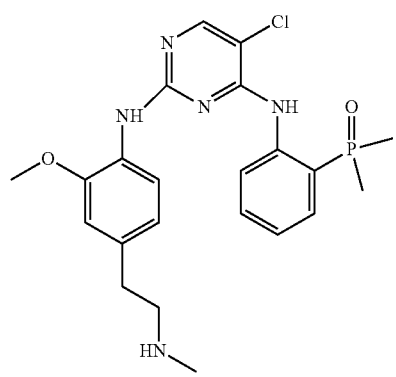
formula (10)
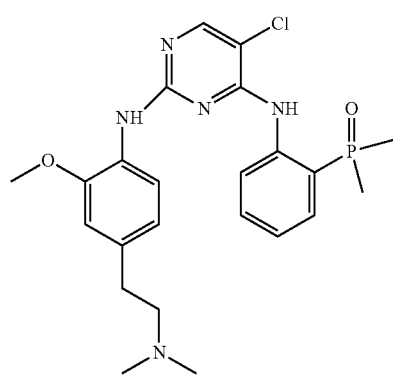
formula (11)
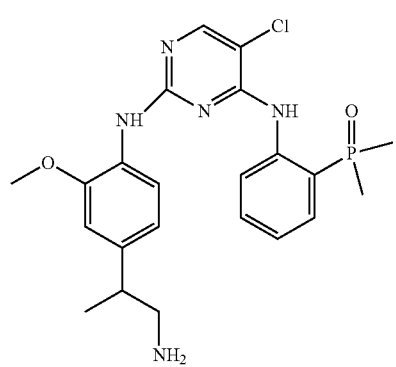
formula (12)
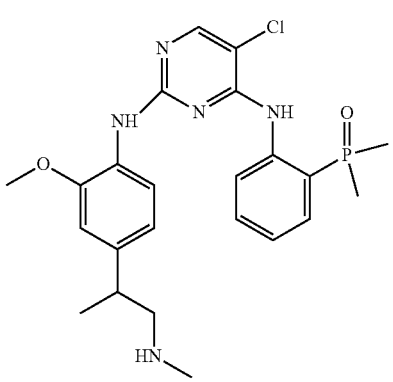
formula (13)
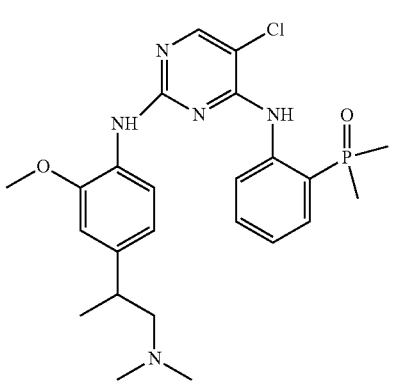
formula (14)
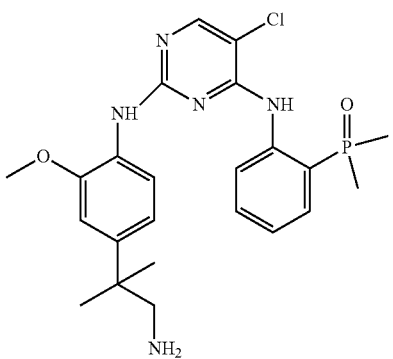
formula (15)
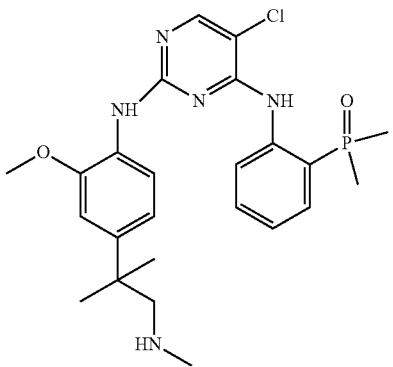

-continued

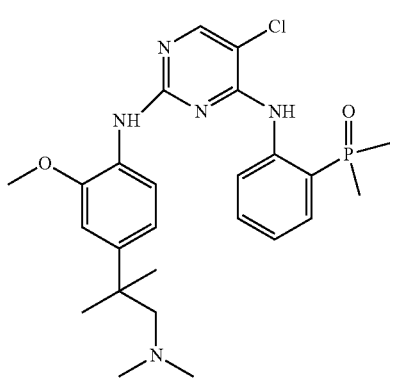

formula (16)

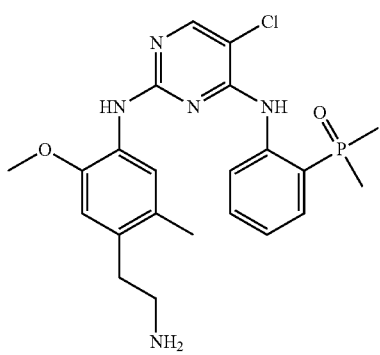

formula (17)

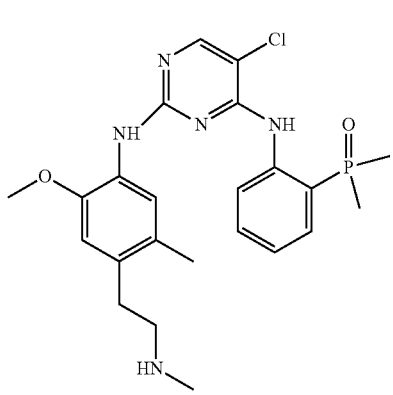

formula (18)

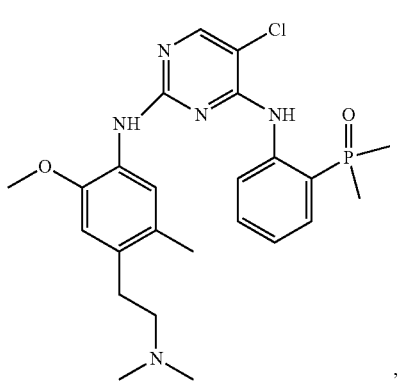

and formula (19)

, or a pharmaceutically acceptable salt, a crystal form, a prodrug, a metabolite, a hydrate, a solvate, a stereoisomer or an isotopic derivative thereof.

10. A pharmaceutical composition containing the compound according to claim 1, or a pharmaceutically acceptable salt, a crystal form, a prodrug, a metabolite, a hydrate, a solvate, a stereoisomer, or an isotopic derivative thereof, and pharmaceutically acceptable excipient(s).

11. The compound according to claim 1, wherein $R_1$ is Cl;
or a pharmaceutically acceptable salt, a crystal form, a prodrug, a metabolite, a hydrate, a solvate, a stereoisomer, or an isotopic derivative thereof.

12. The compound according to claim 1, wherein $R_2$ is H;
or a pharmaceutically acceptable salt, a crystal form, a prodrug, a metabolite, a hydrate, a solvate, a stereoisomer, or an isotopic derivative thereof.

13. The compound according to claim 1, wherein $R_7$ is —$OCH_3$;
or a pharmaceutically acceptable salt, a crystal form, a prodrug, a metabolite, a hydrate, a solvate, a stereoisomer, or an isotopic derivative thereof.

14. The compound according to claim 1, wherein $R_8$ is selected from H and methyl;
or a pharmaceutically acceptable salt, a crystal form, a prodrug, a metabolite, a hydrate, a solvate, a stereoisomer, or an isotopic derivative thereof.

15. A compound, wherein the compound is selected from:

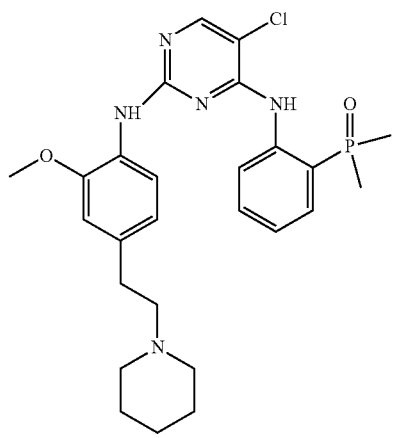

formula (20)

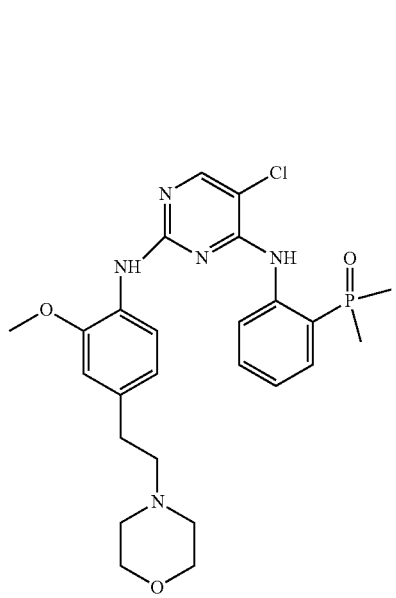

formula (21)

and

-continued
formula (22)
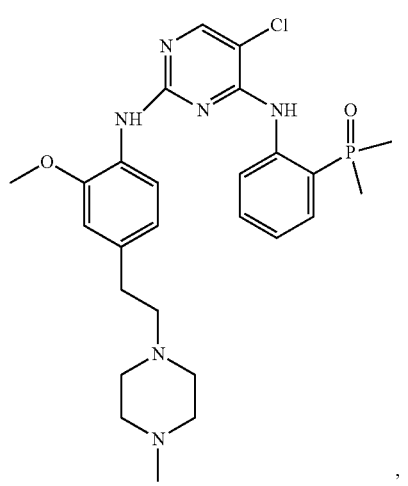
,
or a pharmaceutically acceptable salt, a crystal form, a prodrug, a metabolite, a hydrate, a solvate, a stereoisomer, or an isotopic derivative thereof.
* * * * *